(12) United States Patent
Estrada et al.

(10) Patent No.: US 11,028,080 B2
(45) Date of Patent: Jun. 8, 2021

(54) SUBSTITUTED PYRIMIDINES AS LRKK2 INHIBITORS

(71) Applicant: Denali Therapeutics Inc., South San Francisco, CA (US)

(72) Inventors: Anthony A. Estrada, San Mateo, CA (US); Jianwen A. Feng, San Mateo, CA (US); Joseph P. Lyssikatos, South San Francisco, CA (US); Zachary K. Sweeney, Redwood City, CA (US); Javier de Vicente Fidalgo, Foster City, CA (US)

(73) Assignee: DENALI THERAPEUTICS INC., South San Francisco, CA (US)

( * ) Notice: Subject to any disclaimer, the term of this patent is extended or adjusted under 35 U.S.C. 154(b) by 0 days.

(21) Appl. No.: 16/083,438

(22) PCT Filed: Mar. 10, 2017

(86) PCT No.: PCT/US2017/021964
§ 371 (c)(1),
(2) Date: Sep. 7, 2018

(87) PCT Pub. No.: WO2017/156493
PCT Pub. Date: Sep. 14, 2017

(65) Prior Publication Data
US 2019/0084975 A1  Mar. 21, 2019

Related U.S. Application Data

(60) Provisional application No. 62/411,142, filed on Oct. 21, 2016, provisional application No. 62/351,044, filed on Jun. 16, 2016, provisional application No. 62/307,343, filed on Mar. 11, 2016.

(51) Int. Cl.
| | | |
|---|---|---|
| *A61K 31/506* | (2006.01) | |
| *C07D 239/42* | (2006.01) | |
| *C07D 417/12* | (2006.01) | |
| *C07D 417/14* | (2006.01) | |
| *C07D 403/14* | (2006.01) | |
| *C07D 403/12* | (2006.01) | |
| *C07D 498/08* | (2006.01) | |

(52) U.S. Cl.
CPC ......... *C07D 417/12* (2013.01); *C07D 403/12* (2013.01); *C07D 403/14* (2013.01); *C07D 417/14* (2013.01); *C07D 498/08* (2013.01)

(58) Field of Classification Search
CPC ........................... A61K 31/506; C07D 239/42
USPC .......................................... 514/275; 544/331
See application file for complete search history.

(56) References Cited

U.S. PATENT DOCUMENTS

| | | | |
|---|---|---|---|
| 7,144,911 B2 | 12/2006 | Flynn et al. | |
| 8,815,882 B2 | 8/2014 | Baker-Glenn et al. | |
| 9,676,792 B2 | 6/2017 | Gray et al. | |
| 9,932,325 B2 | 4/2018 | Estrada et al. | |
| 2009/0105266 A1 | 4/2009 | Glatthar et al. | |
| 2012/0149662 A1 | 6/2012 | Babu et al. | |
| 2013/0079324 A1 | 3/2013 | Cheng et al. | |
| 2013/0267513 A1 | 10/2013 | Chan et al. | |
| 2015/0051238 A1 | 2/2015 | Baker-Glenn et al. | |
| 2017/0362206 A1 | 12/2017 | Estrada et al. | |
| 2018/0208582 A1 | 7/2018 | Estrada et al. | |
| 2018/0327391 A1 | 11/2018 | Estrada et al. | |
| 2020/0157081 A1 | 5/2020 | Estrada et al. | |

FOREIGN PATENT DOCUMENTS

| | | |
|---|---|---|
| CN | 105461694 | 4/2016 |
| TW | 201704227 | 2/2017 |
| WO | WO 2000/039108 | 7/2000 |
| WO | WO 2003/076658 | 9/2003 |
| WO | WO 2004/060306 | 7/2004 |
| WO | WO 2005/086656 | 9/2005 |
| WO | WO 2006/014290 | 2/2006 |
| WO | WO 2007/009524 | 1/2007 |
| WO | WO 2007/117995 | 10/2007 |
| WO | WO 2007/149798 | 12/2007 |
| WO | WO 2008/118822 | 10/2008 |

(Continued)

OTHER PUBLICATIONS

Wolff, Manfred E., Ed. Burger's Medicinal Chemistry and Drug Discovery—Fifth Edition, vol. 1: Principles and Practice, New York: John Wiley & Sons, 1994, 975-977.*
Jordan, V. C. Nature Reviews: Drug Discovery, 2, 2003, 205.*
Hackam, et al. JAMA, 296(14), 2006, 1731-1732.*
International Search Report and Written Opinion for PCT/US2017/21964 dated May 26, 2017, 15 pages.
U.S. Appl. No. 16/616,241, filed Nov. 22, 2019, Estrada et al.
Chan et al., "Discovery of a Highly Selective, Brain-Penetrant Aminopyrazole LRRK2 Inhibitor", ACS Medicinal Chemistry Letters, 2013, 4(1), 85-90.

(Continued)

*Primary Examiner* — Douglas M Willis
(74) *Attorney, Agent, or Firm* — Rothwell, Figg, Ernst & Manbeck, P.C.

(57) ABSTRACT

The present disclosure relates generally to compounds of formula (I)

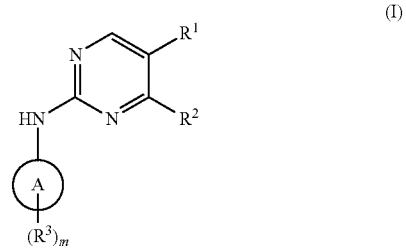

or a pharmaceutically acceptable salt, prodrug, deuterated analog, tautomer, stereoisomer, or mixture of stereoisomers thereof and their use as LRRK2 inhibitors.

53 Claims, No Drawings

(56) References Cited

FOREIGN PATENT DOCUMENTS

| WO | WO 2008/128968 | 10/2008 |
|---|---|---|
| WO | WO 2008/137619 | 11/2008 |
| WO | WO 2008/147626 | 12/2008 |
| WO | WO 2009/032694 | 3/2009 |
| WO | WO 2009/127642 | 10/2009 |
| WO | WO 2010/101973 | 9/2010 |
| WO | WO 2010/111406 | 9/2010 |
| WO | WO 2011/060295 | 5/2011 |
| WO | WO 2011/151360 | 12/2011 |
| WO | WO 2011/156698 | 12/2011 |
| WO | WO 2012/058193 | 5/2012 |
| WO | WO 2012/062783 | 5/2012 |
| WO | WO 2012/075046 | 6/2012 |
| WO | WO 2012/174338 | 12/2012 |
| WO | WO 2013/014162 | 1/2013 |
| WO | WO 2013/042006 | 3/2013 |
| WO | WO 2013/079493 | 6/2013 |
| WO | WO 2013/079494 | 6/2013 |
| WO | WO 2013/079495 | 6/2013 |
| WO | WO 2013/079496 | 6/2013 |
| WO | WO 2013/079505 | 6/2013 |
| WO | WO 2013/126283 | 8/2013 |
| WO | WO 2013/130976 | 9/2013 |
| WO | WO 2013/164321 | 11/2013 |
| WO | WO 2013/164323 | 11/2013 |
| WO | WO 2014/116772 | 7/2014 |
| WO | WO 2014/130241 | 8/2014 |
| WO | WO 2014/135245 | 9/2014 |
| WO | WO 2014/150981 | 9/2014 |
| WO | WO 2014/170248 | 10/2014 |
| WO | WO 2014/181137 | 11/2014 |
| WO | WO 2014/181287 | 11/2014 |
| WO | WO 2015/113452 | 8/2015 |
| WO | WO 2015/131005 | 9/2015 |
| WO | WO 2015/148867 | 10/2015 |
| WO | WO 2015/148869 | 10/2015 |
| WO | WO 16/033100 | * 3/2016 |
| WO | WO 2016/090285 | 6/2016 |
| WO | WO 2016/149311 | 9/2016 |
| WO | WO 2016/201370 | 12/2016 |
| WO | WO 2017/046675 | 3/2017 |
| WO | WO 2017/087282 | 5/2017 |
| WO | WO 2017/087905 | 5/2017 |
| WO | WO 2017/089390 | 6/2017 |
| WO | WO 2017/100703 | 6/2017 |
| WO | WO 2017/106771 | 6/2017 |
| WO | WO 2017/156493 | 9/2017 |
| WO | WO-2017218843 | 12/2017 |
| WO | WO 2018/217946 | 11/2018 |

OTHER PUBLICATIONS

Estrada et al., "Discovery of Highly Potent, Selective, and Brain-Penetrant Aminopyrazole Leucine-Rich Repeat Kinase 2 (LRRK2) Small Molecule Inhibitors", Journal of Medicinal Chemistry, 2014, 57(3), 921-936.

Tan, et al. Development of Selective Covalent Janus Kinase 3 Inhibitors. J Med Chem. Aug. 27, 2015;58(16):6589-606.

International Preliminary Report on Patentability for International Application No. PCT/US2017/021964 dated Sep. 11, 2018. 8 pages.

* cited by examiner

SUBSTITUTED PYRIMIDINES AS LRKK2 INHIBITORS

CROSS-REFERENCE TO RELATED APPLICATIONS

This application is a U.S. National Stage Application under 35 U.S.C. § 371 of International Application No. PCT/US2017/021964, filed Mar. 10, 2017, which application claims the benefit under 35 U.S.C. 119(e) to U.S. Provisional Application Nos. 62/307,343, filed Mar. 11, 2016; 62/351,044, filed Jun. 16, 2016; and 62/411,142, filed Oct. 21, 2016, where the contents of each is incorporated herein by reference in its entirety.

FIELD

The present disclosure relates generally to novel heteroaryl-substituted pyrimidines and their use as therapeutic agents, for example, as inhibitors of LRRK2.

BACKGROUND

Neurodegenerative diseases, such as Parkinson's disease, amyotrophic lateral sclerosis (ALS), Alzheimer's disease, Lewy body dementia, and Huntington's disease affect millions of people. Parkinson's disease is a chronic, progressive motor system disorder characterized by selective degeneration and cell death of dopaminergic neurons in the substantial nigra region of the brain. This leaves patients with impaired ability to direct and control their movements. The cause of the disease was generally considered to be sporatic and unknown, but significant advancements in understanding have been made in the last 15 years.

The genetic basis for the disease and associated pathogenic mechanisms have led exploration of the gene encoding leucine-rich repeat kinase 2 (LRRK2) protein and its association with hereditary Parkinson's disease (Paisan-Ruiz et al., Neuron, Vol. 44(4), 2004, 601-607). LRRK2 is a member of the ROCO protein family and shares 5 conserved domains with all other family members. Many mis-sense mutations to the LRRK2 gene have been linked with autosomal dominant Parkinson's disease in familial studies (Trinh and Farrar, Nature Reviews in Neurology, Vol. 9, 2013, 445-454; Paisan-Ruiz et al., J. Parkinson's Disease, Vol. 3, 2013, 85-103). The most common pathogenic mutation, G2019S, occurs in the highly conserved kinase domain of LRRK2 (See Gilks et al., Lancet, Vol 365, 2005, 415-416). In vitro studies indicate Parkinson's disease-associated mutation leads to increased LRRK2 activity and a decreased rate of GTP hydrolysis (Guo et al., Experimental Cell Research, Vol. 313(16), 2007, 3658-3670). This evidence suggests the kinase and GTPase activities of LRRK2 are important for pathogenesis and the LRRK2 kinase domain may regulate overall LRRK2 function (See Cookson, Nat. Rev. Neurosci., Vol. 11, 2010, 791-797).

While progress has been made in this field, there remains a need for improved inhibitors of the LRRK2 receptor which are useful for treatment of various neurodegenerative diseases, such as Parkinson's disease, Alzheimer's disease and amyotrophic lateral sclerosis.

SUMMARY

Provided herein are compounds that are useful as inhibitors of LRRK2, including compounds with good pharmacologic properties. The disclosure also provides compositions, including pharmaceutical compositions, kits that include the compounds, and methods of using (or administering) and making the compounds. The disclosure further provides compounds or compositions thereof for use in a method of treating a disease, disorder, or condition that is mediated, at least in part, by LRRK2. Moreover, the disclosure provides uses of the compounds or compositions thereof in the manufacture of a medicament for the treatment of a disease, disorder, or condition that is mediated, at least in part, by LRRK2.

In one embodiment, provided is a compound of formula (I):

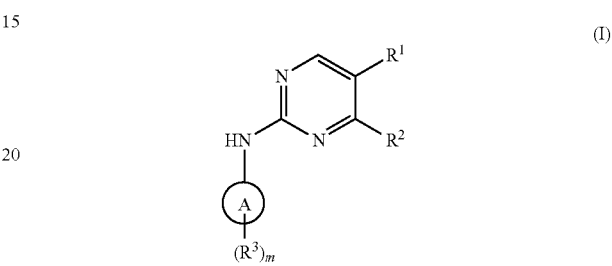

or a pharmaceutically acceptable salt, prodrug, deuterated analog, stereoisomer, or a mixture of stereoisomers thereof, wherein:

$R^1$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^4$;

$R^2$ is optionally substituted cycloalkyl, cycloalkoxy, heteroaryl, optionally substituted $C_{1-6}$ alkoxy, —S—$C_{1-6}$ alkyl, —S(O)$_{1-2}$—$C_{1-6}$ alkyl or —N($R^5$)($R^6$);

m is 1, 2, 3, or 4;

each $R^3$ is independently H, halo, cyano, $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, alkylheteroarylcycloalkyl, amido, amidoalkyl, —N($R^{16}$)$_2$, or —C(O)$R^7$, wherein each $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, and alkylheteroarylcycloalkyl is optionally substituted; or two $R^3$ together with the atom to which they are attached form a cycloalkyl or heterocyclyl, wherein each cycloalkyl and heterocyclyl is optionally substituted;

$R^4$ is $C_{1-6}$ alkyl, $C_{1-6}$ alkoxy, —N($R^{17}$)$_2$, or heterocyclyl, wherein each $C_{1-6}$ alkyl, $C_{1-6}$ alkoxy and heterocyclyl is optionally substituted;

$R^5$ and $R^6$ are each independently H, $C_{1-6}$ alkyl, $C_{1-6}$ haloalkyl, cycloalkyl; or $R^5$ and $R^6$ together with the atom to which they are attached form an optionally substituted heterocyclyl;

$R^7$ is $C_{1-6}$ alkyl, $C_{1-6}$ haloalkyl, $C_{1-6}$ alkoxy, or heterocyclyl, wherein each $C_{1-6}$ alkyl, $C_{1-6}$ haloalkyl, $C_{1-6}$ alkoxy, and heterocyclyl is independently optionally substituted with one or more substituents selected from halo, cyano, hydroxy, $C_{1-6}$ alkoxy, and $C_{1-6}$ alkylsulfonyl; each $R^{16}$ is independently H or optionally substituted $C_{1-6}$ alkyl;

each $R^{17}$ is independently H or optionally substituted $C_{1-6}$ alkyl; and ring A is a 5-membered heteroaryl, provided that ring A is not pyrazolyl, and provided that when $R^5$ or $R^6$ is cycloalkyl, then ring A is not isothiazolyl or thiophenyl.

In certain embodiments, when $R^5$ or $R^6$ is cycloalkyl, then ring A is thiazolyl. In another embodiment, provided is a pharmaceutical composition comprising a compound of formula (I), or a pharmaceutically acceptable salt, prodrug, stereoisomer, or a mixture of stereoisomers thereof, and a pharmaceutically acceptable carrier, diluent, or excipient.

In another embodiment, provided is a method for treating a disease or condition mediated, at least in part, by LRRK2, the method comprising administering an effective amount of the pharmaceutical composition comprising a compound of formula (I), or a pharmaceutically acceptable salt, prodrug, stereoisomer, or a mixture of stereoisomers thereof, and a pharmaceutically acceptable carrier, diluent, or excipient, to a subject in need thereof.

In another embodiment, provided is a compound for use in therapy. In some embodiments, the compound is provided for use in the treatment of a neurodegenerative disease, cancer, or an inflammatory disease.

In another embodiment, provided is a method for preparing a compound of formula (I):

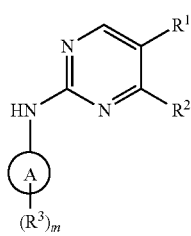

(I)

comprising coupling a compound of formula (Y):

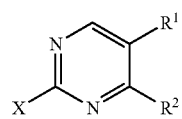

(Y)

wherein X is a leaving group,
with a compound of formula (Z):

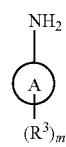

(Z)

under conditions to provide the compound of formula (I), wherein $R^1$, $R^2$, $R^3$, ring A and m are as defined for compound of formula (I).

DETAILED DESCRIPTION

The following description sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount 5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy and 1,2-dimethylbutoxy.

"Alkoxyalkyl" refers to the group "alkyl-O-alkyl".

"Alkylthio" refers to the group "alkyl-S—".

"Alkylsulfinyl" refers to the group "alkyl-S(O)—".

"Alkylsulfonyl" refers to the group "alkyl-S(O)$_2$—".

"Alkylsulfonylalkyl" refers to -alkyl-S(O)$_2$-alkyl.

"Acyl" refers to a group —C(O)R$^y$, wherein R$^y$ is hydrogen, alkyl, alkenyl, alkynyl, cycloalkyl, heterocyclyl, aryl, heteroalkyl, or heteroaryl; each of which may be optionally substituted, as defined herein. Examples of acyl include formyl, acetyl, cyclohexylcarbonyl, cyclohexylmethyl-carbonyl and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein, or R$^y$ and R$^z$ are taken together to form a cycloalkyl or heterocyclyl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Aminoalkyl" refers to the group "-alkyl-NR$^y$R$^z$," wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Amidoalkyl" refers to the group "-alkyl-C(O)NR$^y$R$^z$," wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Amidino" refers to —C(NR$^y$)(NR$^z{}_2$), wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to the group "aryl-alkyl-".

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Carboxyl ester" or "ester" refer to both —OC(O)R$^x$ and —C(O)OR$^x$, wherein R$^x$ is alkyl, alkenyl, alkynyl, cycloalkyl, heterocyclyl, aryl, heteroalkyl, or heteroaryl; each of which may be optionally substituted, as defined herein.

"Cyanoalkyl" refers to refers to an alkyl group as defined above, wherein one to three hydrogen atoms are replaced by a cyano group.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e. the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkoxy" refers to "—O-cycloalkyl."

"Cycloalkylalkyl" refers to the group "cycloalkyl-alkyl-."

"Cycloalkylalkoxy" refers to "—O-alkyl-cycloalkyl."

"Guanidino" refers to —NR$^y$C(=NR$^z$)(NR$^y$R$^z$, wherein each R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein. "Hydrazino" refers to —NHNH$_2$.

"Imino" refers to a group —C(NR$^y$)R$^z$, wherein R$^y$ and R$^z$ are ach independently hydrogen, alkyl, alkenyl, alkynyl, cycloalkyl, heterocyclyl, aryl, heteroalkyl, or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, cycloalkyl, heterocyclyl, aryl, heteroalkyl, or heteroaryl; each of which may be optionally substituted, as defined herein.

"Halogen" or "halo" refers to atoms occupying group VIIA of the periodic table, such as fluoro, chloro, bromo, or iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more hydrogen atoms are replaced by a halogen.

"Hydroxyalkyl" refers to an alkyl group as defined above, wherein one or more hydrogen atoms are replaced by a hydroxy group.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2, or 3 carbon atoms may be independently replaced with the same or different heteroatomic group. Heteroatomic groups include, but are not limited to, —$NR^y$—, —O—, —S—, —S(O)—, —$S(O)_2$—, and the like, wherein $R^y$ is hydrogen, alkyl, alkenyl, alkynyl, cycloalkyl, heterocyclyl, aryl, heteroalkyl, or heteroaryl; each of which may be optionally substituted, as defined herein. Examples of heteroalkyl groups include ethers (e.g., —$CH_2OCH_3$, —$CH(CH_3)OCH_3$, —$CH_{2C}H2CH_3$, —$CH_2CH_2OCH_2CH_2OCH_3$, etc.), thioethers (e.g., —$CH_2SCH_3$, —$CH(CH_3)SCH_3$, —$CH_2CH_2SCH_3$, —$CH_2CH_2SCH_2CH_2SCH_3$, etc.), sulfones (e.g., —$CH_2S(O)_2CH_3$, —$CH(CH_3)S(O)_2CH_3$, —$CH_2CH_2S(O)_2CH_3$, —$CH_2CH_2S(O)_2CH_2CH_2OCH_3$, etc.), and amines (e.g., —$CH_2NR^yCH_3$, —$CH(CH_3)NR^yCH_3$, —$CH_2CH_2NR^yCH_3$, —$CH_2CH_2NR^yCH_2CH_2NR^yCH_3$, etc., where $R^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heteroarylcycloalkyl" refers to the group "heteroaryl-cycloalkyl-".

"Alkylheteroarylalkyl" refers to the group "heteroaryl-alkyl-" wherein the heteroaryl moiety is substituted with at least one $C_{1-6}$ alkyl.

"Alkylheteroarylcycloalkyl" refers to the group "heteroaryl-cycloalkyl-" wherein the heteroaryl moiety is substituted with at least one $C_{1-6}$ alkyl.

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more oxo (=O) or N-oxide (—O$^-$) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e. thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-".

The term "leaving group" refers to an atom or a group of atoms that is displaced in a chemical reaction as stable species taking with it the bonding electrons. The non-limiting examples of a leaving group include, halo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tert-butyl-benzene)sulfonyloxy, benzenesulfonyloxy, (4-methoxy-benzene)sulfonyloxy, and the like.

"Oxo" refers to the group (=O) or (O).

"Oxime" refers to the group —CR$^y$(=NOH) wherein R$^y$ is hydrogen, alkyl, alkenyl, alkynyl, cycloalkyl, heterocyclyl, aryl, heteroalkyl, or heteroaryl; each of which may be optionally substituted, as defined herein.

"Sulfonyl" refers to the group —S(O)$_2$R$^y$, where R$^y$ is hydrogen, alkyl, alkenyl, alkynyl, cycloalkyl, heterocyclyl, aryl, heteroalkyl, or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —S(O)R$^y$, where R$^y$ is hydrogen, alkyl, alkenyl, alkynyl, cycloalkyl, heterocyclyl, aryl, heteroalkyl, or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —SO$_2$NR$^y$R$^z$ and —NR$^y$SO$_2$R$^z$, where R$^y$ and R$^z$ are each independently hydrogen, alkyl, alkenyl, alkynyl, cycloalkyl, heterocyclyl, aryl, heteroalkyl, or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si(R$^y$)$_3$ wherein each R$^y$ is independently hydrogen, alkyl, alkenyl, alkynyl, heteroalkyl, cycloalkyl, aryl, heteroaryl, or heterocyclyl.

In one embodiment, "substituted" includes any of the above groups (e.g., alkyl, alkenyl, alkynyl, alkylene, alkoxy, haloalkyl, haloalkoxy, cycloalkyl, aryl, heterocyclyl, heteroaryl, and/or heteroalkyl) in which one or more hydrogen atoms are replaced with —NR$^g$R$^h$, —NR$^g$C(=O)R$^h$, —NR$^g$C(=O)NR$^g$R$^h$, —NR$^g$C(=O)OR$^h$, —NR$^g$SO$_2$R$^h$, —OC(=O)NR$^g$R$^h$, —OR$^g$, —SR$^g$, —SOR$^g$, —SO$_2$R$^g$, —OSO$_2$R$^g$, —SO$_2$OR$^g$, =NSO$_2$R$^g$, and —SO$_2$NR$^g$R$^h$. "Substituted" also means any of the above groups in which one or more hydrogen atoms are replaced with —C(=O)R$^g$, —C(=O)OR), —C(=O)NR$^g$R$^h$, —CH$_2$SO$_2$R$^g$, —CH$_2$SO$_2$NR$^g$R$^h$. In the foregoing, R$^g$ and R$^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl group. In addition, each of the foregoing substituents may also be optionally substituted with one or more of the above substituents.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxy, halo, alkoxy, acyl, oxo, amino, cycloalkyl, heterocyclyl, aryl and heteroaryl. In other embodiments, the one or more substituents may be further substituted with halo, alkyl, haloalkyl, hydroxy, alkoxy, cycloalkyl, heterocyclyl, aryl, or heteroaryl, each of which is substituted. In other embodiments, the substituents may be further substituted with halo, alkyl, haloalkyl, alkoxy, hydroxy, cycloalkyl, heterocyclyl, aryl, or heteroaryl, each of which is unsubstituted.

Any compound or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I and $^{125}$I, respectively. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^{3}H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, stereoisomers and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., $HN(alkyl)_2$), trialkyl amines (i.e., $N(alkyl)_3$), substituted alkyl amines (i.e., $NH_2$ (substituted alkyl)), di(substituted alkyl) amines (i.e., $HN$(substituted alkyl)$_2$), tri(substituted alkyl) amines (i.e., $N$(substituted alkyl)$_3$), alkenyl amines (i.e., $NH_2$(alkenyl)), dialkenyl amines (i.e., $HN(alkenyl)_2$), trialkenyl amines (i.e., $N(alkenyl)_3$), substituted alkenyl amines (i.e., $NH_2$ (substituted alkenyl)), di(substituted alkenyl) amines (i.e., $HN$(substituted alkenyl)$_2$), tri(substituted alkenyl) amines (i.e., $N$(substituted alkenyl)$_3$, mono-, di- or tri-cycloalkyl amines (i.e., $NH_2$(cycloalkyl), $HN(cycloalkyl)_2$, $N$(cycloalkyl)$_3$), mono-, di- or tri-arylamines (i.e., $NH_2$(aryl), $HN(aryl)_2$, $N(aryl)_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)-for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another.

"Diastereomers" are stereoisomers that have at least two asymmetric atoms, but which are not mirror-images of each other.

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As used herein, "pharmaceutically acceptable carrier" or "pharmaceutically acceptable excipient" or "excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

2. List of Abbreviations and Acronyms

| Abbreviation | Meaning |
| --- | --- |
| Ac$_2$O | Acetic anhydride |
| ATP | Adenosine triphosphate |
| br. s. | Broad singlet |

-continued

| Abbreviation | Meaning |
| --- | --- |
| n-BuOH | n-Butanol |
| DCM | Dichloromethane |
| DMF | Dimethylformamide |
| DMSO | Dimethylsulfoxide |
| DTT | Dithiothreitol |
| EDTA | Ethylenediamine tetraacetate |
| EGTA | Ethylene glycol tetraacetic acid |
| EtOH | Ethanol |
| EtOAC/EA | Ethyl acetate |
| h | Hour |
| HPE | Hundred percent effect |
| HPLC | High pressure liquid chromatography |
| J | Coupling constant (MHz) |
| LCMS | Liquid chromatography-mass spectrometry |
| m | Multiplet |
| MeI | Methyl iodide |
| MHz | Megahertz |
| m/z | Mass-to-charge ratio |
| [M + H]$^+$ | Mass peak plus hydrogen |
| min | Minute(s) |
| mM | Millimolar |
| mmol | Millimole |
| MS | Mass spectrometry |
| MsCl | Methanesulfonyl chloride |
| MTBE | Methyl tert-butyl ether |
| NMR | Nuclear magnetic resonance |
| PE | Petroleum ether |
| POD | Peroxidase |
| PTSA | para-Toluene sulfonic acid |
| q | Quartet |
| rt | Room temperature |
| rpm | Revolutions per minute |
| s | Singlet (when used with NMR) |
| t | Triplet |
| TEA | Triethylamine |
| THF | Tetrahydrofuran |
| TFA | Trifluoroacetic acid |
| TLC | Thin layer chromatography |
| TMEDA | N,N,N',N'-Tetramethylethylenediamine |
| TR-FRET | Time-resolved fluorescence energy transfer |
| TRIS | Tris(hydroxymethyl)amino methane |
| TsOH | Toluene sulfonic acid |
| UV | Ultraviolet |
| v/v | Volume/volume |
| δ | Chemical shift (ppm) |
| μMol | Micromole |
| μM | Micromolar |
| ZPE | Zero percent effect |

3. Compounds

Provided herein are compounds that are useful as inhibitors of LRRK2. In one embodiment, provided is a compound of formula (I), or a pharmaceutically acceptable salt, prodrug, deuterated analog, stereoisomer, or a mixture of stereoisomers thereof, wherein:

$R^1$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^4$;

$R^2$ is optionally substituted cycloalkyl, cycloalkoxy, heteroaryl, optionally substituted $C_{1-6}$ alkoxy, —S—$C_{1-6}$ alkyl, —S(O)$_{1-2}$—$C_{1-6}$ alkyl or —N($R^5$)($R^6$);

m is 1, 2, 3, or 4;

each $R^3$ is independently H, halo, cyano, $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, alkylheteroarylcycloalkyl, amido, amidoalkyl, —N($R^{16}$)$_2$, or —C(O)$R^7$, wherein each $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, and alkylheteroarylcycloalkyl is optionally substituted; or two $R^3$ together with the atom to which they are attached form a cycloalkyl or heterocyclyl, wherein each cycloalkyl and heterocyclyl is optionally substituted;

$R^4$ is $C_{1-6}$alkyl, $C_{1-6}$alkoxy, —N($R^{17}$)$_2$, or heterocyclyl, wherein each $C_{1-6}$ alkyl, $C_{1-6}$ alkoxy and heterocyclyl is optionally substituted;

$R^5$ and $R^6$ are each independently H, $C_{1-6}$ alkyl, $C_{1-6}$ haloalkyl, cycloalkyl; or $R^5$ and $R^6$ together with the atom to which they are attached form an optionally substituted heterocyclyl;

$R^7$ is $C_{1-6}$ alkyl, $C_{1-6}$ haloalkyl, $C_{1-6}$ alkoxy, or heterocyclyl, wherein each $C_{1-6}$ alkyl, $C_{1-6}$ haloalkyl, $C_{1-6}$ alkoxy, and heterocyclyl is independently optionally substituted with one or more substituents selected from halo, cyano, hydroxy, $C_{1-6}$ alkoxy, and $C_{1-6}$ alkylsulfonyl;

each $R^{16}$ is independently H or optionally substituted $C_{1-6}$ alkyl;

each $R^{17}$ is independently H or optionally substituted $C_{1-6}$ alkyl; and ring A is a 5-membered heteroaryl, provided that ring A is not pyrazolyl, and provided that when $R^5$ or $R^6$ is cycloalkyl, then ring A is not isothiazolyl or thiophenyl.

In certain embodiments, when $R^5$ or $R^6$ is cycloalkyl, then ring A is thiazolyl.

In one embodiment, provided is a compound of formula (I), or a pharmaceutically acceptable salt, prodrug, stereoisomer, or a mixture of stereoisomers thereof, wherein:

$R^1$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^4$;

$R^2$ is optionally substituted cycloalkyl, heteroaryl, $C_{1-6}$ alkoxy, —S—$C_{1-6}$ alkyl, or —N($R^5$)($R^6$);

m is 1, 2, 3, or 4;

each $R^3$ is independently H, halo, cyano, $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, alkylheteroarylcycloalkyl, amido, amidoalkyl, or —C(O)$R^7$, wherein each $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, and alkylheteroarylcycloalkyl is optionally substituted; or two $R^3$ together with the atom to which they are attached form a cycloalkyl or heterocyclyl, wherein each cycloalkyl and heterocyclyl is optionally substituted;

$R^4$ is $C_{1-6}$ alkyl, $C_{1-6}$ alkoxy, —N($R^{17}$)$_2$, or heterocyclyl, wherein each $C_{1-6}$ alkyl, $C_{1-6}$ alkoxy and heterocyclyl is optionally substituted;

$R^5$ and $R^6$ are each independently H or optionally substituted $C_{1-6}$ alkyl; or $R^5$ and $R^6$ together with the atom to which they are attached form an optionally substituted heterocyclyl;

$R^7$ is $C_{1-6}$ alkyl or heterocyclyl, wherein $C_{1-6}$ alkyl, $C_{1-6}$ haloalkyl, and heterocyclyl is independently optionally substituted with one or more substituents selected from halo, cyano, hydroxy, $C_{1-6}$ alkoxy, and $C_{1-6}$ alkylsulfonyl;

each $R^{17}$ is independently H or optionally substituted $C_{1-6}$ alkyl; and ring A is a 5-membered heteroaryl, provided that ring A is not pyrazolyl.

In one embodiment, provided is a compound of formula (I), or a pharmaceutically acceptable salt, prodrug, stereoisomer, or a mixture of stereoisomers thereof, wherein:

$R^1$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^4$;

$R^2$ is optionally substituted cycloalkyl, heteroaryl, $C_{1-6}$ alkoxy, —S—$C_{1-6}$ alkyl, or —N($R^5$)($R^6$);

m is 0, 1, 2, 3, or 4;

each $R^3$ is independently H, halo, cyano, $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, alkylheteroarylcycloalkyl, amido, or —C(O)$R^7$, wherein each $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, and alkylheteroarylcycloalkyl is optionally substituted; or two $R^3$ together with the atom to which they are attached form a cycloalkyl or heterocyclyl, wherein each cycloalkyl and heterocyclyl is optionally substituted;

$R^4$ is $C_{1-6}$ alkyl, $C_{1-6}$ alkoxy, —N($R^{17}$)$_2$, or heterocyclyl, wherein each $C_{1-6}$ alkyl, $C_{1-6}$ alkoxy and heterocyclyl is optionally substituted;

$R^5$ and $R^6$ are each independently H or optionally substituted $C_{1-6}$ alkyl; or $R^5$ and $R^6$ together with the atom to which they are attached form an optionally substituted heterocyclyl;

$R^7$ is $C_{1-6}$ alkyl or heterocyclyl, wherein $C_{1-6}$ alkyl, $C_{1-6}$ haloalkyl, and heterocyclyl is independently optionally substituted with one or more substituents selected from halo, cyano, hydroxy, $C_{1-6}$ alkoxy, and $C_{1-6}$ alkylsulfonyl;

each $R^{17}$ is independently H or optionally substituted $C_{1-6}$ alkyl; and ring A is a 5-membered heteroaryl, provided that ring A is not pyrazolyl.

In another embodiment, provided is a pharmaceutical composition comprising a compound of formula (I), or a pharmaceutically acceptable salt, prodrug, stereoisomer, or a mixture of stereoisomers thereof, and a pharmaceutically acceptable carrier, diluent, or excipient.

In some embodiments, ring A is furyl, thiophenyl, pyrrolyl, imidazolyl, thiazolyl, isothiazolyl, oxazolyl, isoxazolyl, oxadiazolyl, thiadiazolyl, triazolyl, oxatriazolyl, thiatriazolyl, or tetrazolyl. In one embodiment, ring A is pyrrolyl, imidazolyl, thiazolyl, or isothiazolyl. In one embodiment, ring A is pyrrolyl. In one embodiment, ring A is imidazolyl. In one embodiment, ring A is thiazolyl. In one embodiment, ring A is isothiazolyl. In certain embodiments, when $R^5$ or $R^6$ is cycloalkyl, then ring A is not isothiazolyl or thiophenyl. In certain embodiments, when $R^5$ or $R^6$ is cycloalkyl, then ring A is thiazolyl.

In one embodiment, m is 1, 2 or 3 and $R^3$ is other than H. In one embodiment, m is 1, 2 or 3. In another embodiment, m is 1. In another embodiment, m is 2. In another embodiment, m is 3.

In one embodiment, ring A is thiazolyl, m is 2, and $R^3$ is independently, halo, $C_{1-6}$ alkyl, $C_{1-6}$ haloalkyl, $C_{1-6}$ alkyl wherein 1-6 hydrogens have been replaced by deuterium, cycloalkyl, heterocyclyl, wherein said alkyl, cycloalkyl and heterocyclyl are each independently optionally substituted with oxo, halo, $C_{1-6}$ alkyl, $C_{1-6}$ haloalkyl, $C_{1-6}$ alkyl wherein 1-6 hydrogens have been replaced by deuterium, heterocyclyl, or cycloalkyl. In one example, $R^3$ is independently, halo or heterocyclyl, wherein said heterocyclyl is independently optionally substituted with oxo, $C_{1-6}$ alkyl, $C_{1-6}$ haloalkyl, or $C_{1-6}$ alkyl wherein 1-6 hydrogens have been replaced by deuterium.

In some embodiments, provided is a compound of formula (I'):

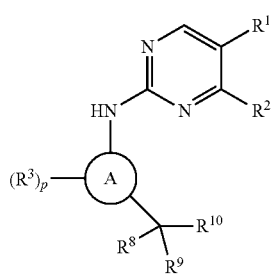

(I')

or a pharmaceutically acceptable salt, prodrug, deuterated analog, stereoisomer, or a mixture of stereoisomers thereof, wherein:
ring A is as defined herein;
$R^8$ and $R^9$ are each independently H or $C_{1-6}$ alkyl, or $R^8$ and $R^9$ with the carbon attached thereto form a $C_{1-6}$ cycloalkyl, and $R^{10}$ is H, cyano, heteroaryl, —C(O)NR$^{12}$R$^{13}$, or alkylheteroaryl; or $R^9$ and $R^{10}$ form a heterocyclyl substituted with oxo and independently optionally substituted with one to four halo or $C_{1-6}$ alkyl;
$R^8$ and $R^9$ with the carbon attached thereto form a C(O) and $R^{10}$ is $C_{1-6}$ alkyl, amino, $C_{1-6}$ alkylamino, $C_{1-6}$ haloalkyl, or heterocyclyl optionally substituted with one or more halo;
p is 0, 1, 2 or 3; and
$R^{12}$ and $R^{13}$ are each independently H, $C_{1-6}$ alkyl, $C_{2-6}$ alkenyl, $C_{2-6}$ alkynyl, cycloalkyl, heterocyclyl, aryl, heteroalkyl, or heteroaryl, wherein each of $C_{1-6}$ alkyl, $C_{2-6}$ alkenyl, $C_{2-6}$ alkynyl, cycloalkyl, heterocyclyl, aryl, heteroalkyl, and heteroaryl is optionally substituted, or $R^{12}$ and $R^{13}$ together with the nitrogen to which they are attached, form a three- to six-membered optionally substituted heterocyclyl.

In some embodiments, provided is a compound of formula (I'), or a pharmaceutically acceptable salt, prodrug, stereoisomer, or a mixture of stereoisomers thereof, wherein:
ring A is as defined herein;
$R^8$ and $R^9$ are each independently H or $C_{1-6}$ alkyl, or $R^8$ and $R^9$ with the carbon attached thereto form a $C_{1-6}$ cycloalkyl, or a optionally substituted heterocyclyl, and $R^{10}$ is $C_{1-6}$ alkyl, cyano, heteroaryl, —C(O)NR$^{12}$R$^{13}$, or alkylheteroaryl; or
$R^8$ and $R^9$ with the carbon attached thereto form a C(O) and $R^{10}$ is $C_{1-6}$ alkyl, $C_{1-6}$ haloalkyl, or heterocyclyl independently optionally substituted with one or more halo;
$R^1$, $R^2$, and $R^3$ are as defined herein for the compound of formula (I);
p is 0, 1, 2 or 3; and
$R^{12}$ and $R^{13}$ are each independently H, $C_{1-6}$ alkyl, $C_{2-6}$ alkenyl, $C_{2-6}$ alkynyl, cycloalkyl, heterocyclyl, aryl, or heteroaryl, wherein each $C_{1-6}$ alkyl, $C_{2-6}$ alkenyl, $C_{2-6}$ alkynyl, cycloalkyl, heterocyclyl, aryl, and heteroaryl is independently optionally substituted, or $R^{12}$ and $R^{13}$ together with the nitrogen to which they are attached, form a optionally substituted three- to six-membered heterocyclyl.

In some embodiments, provided is a compound of formula (I'), or a pharmaceutically acceptable salt, prodrug, stereoisomer, or a mixture of stereoisomers thereof, wherein:
ring A is as defined herein;
$R^8$ and $R^9$ are each independently H or $C_{1-6}$ alkyl, or $R^8$ and $R^9$ with the carbon attached thereto form a $C_{1-6}$ cycloalkyl, and $R^{10}$ is cyano, heteroaryl, —C(O)NR$^{12}$R$^{13}$, or alkylheteroaryl; or
$R^8$ and $R^9$ with the carbon attached thereto form a C(O) and $R^{10}$ is $C_{1-6}$ alkyl, $C_{1-6}$ haloalkyl, or heterocyclyl independently optionally substituted with one or more halo;
$R^1$, $R^2$, and $R^3$ are as defined herein for the compound of formula (I);
p is 0, 1, 2 or 3; and
$R^{12}$ and $R^{13}$ are each independently H, $C_{1-6}$ alkyl, $C_{2-6}$ alkenyl, $C_{2-6}$ alkynyl, cycloalkyl, heterocyclyl, aryl, or heteroaryl, wherein each $C_{1-6}$ alkyl, $C_{2-6}$ alkenyl, $C_{2-6}$ alkynyl, cycloalkyl, heterocyclyl, aryl, and heteroaryl is independently optionally substituted, or $R^{12}$ and $R^{13}$ together with the nitrogen to which they are attached, form a optionally substituted three- to six-membered heterocyclyl.

In one embodiment, p is 0. In another embodiment, p is 1. In another embodiment, p is 2. In another embodiment, p is 3.

In some embodiments, provided is a compound of formula (II):

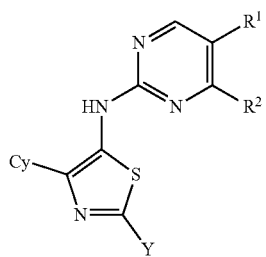

(II)

or a pharmaceutically acceptable salt, prodrug, deuterated analog, stereoisomer, or a mixture of stereoisomers thereof, wherein:
Cy is cycloalkyl;
Y is H, hydroxy, halo, ester, cyano, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, alkylheteroarylcycloalkyl, amido, amidoalkyl, or —N(R$^{16}$)$_2$, —C(O)R$^7$, wherein each C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ alkoxyalkyl, C$_{1-6}$ cyanoalkyl, C$_{1-6}$ aminoalkyl, C$_{1-6}$ alkylsulfonyl, C$_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, and alkylheteroarylcycloalkyl is optionally substituted;

R$^7$ is C$_{1-6}$ alkyl, C$_{1-6}$ haloalkyl, C$_{1-6}$ alkoxy, or heterocyclyl, wherein C$_{1-6}$ alkyl, C$_{1-6}$ haloalkyl, C$_{1-6}$ alkoxy, and heterocyclyl is independently optionally substituted with one or more substituents selected from halo, cyano, hydroxy, C$_{1-6}$ alkoxy, and C$_{1-6}$ alkylsulfonyl; and each R$^{16}$ is independently H or optionally substituted C$_{1-6}$ alkyl.

In one embodiment, Y is cyano, C$_{1-6}$ alkyl, C$_{1-6}$ cyanoalkyl, cycloalkyl, cyanocycloalkyl, heterocyclyl, heteroarylalkyl, alkylheteroarylalkyl, heteroarylcycloalkyl, (C$_{1-6}$ alkyl)NHCO, amidoalkyl, —C(O)R$^7$, or heterocyclyl substituted with oxo and one to two C$_{1-6}$ alkyl; and R$^7$ is heterocyclyl optionally substituted with one to three halo.

In certain embodiments, Y is:

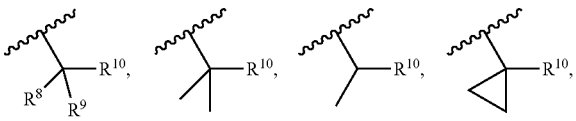

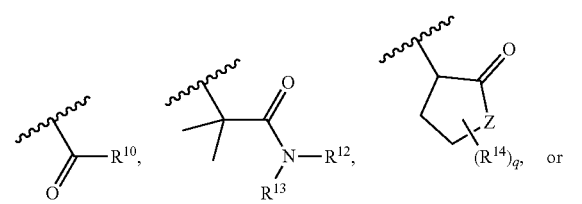

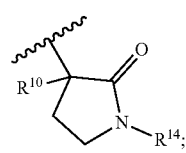

wherein

R$^8$ and R$^9$ are each independently H or C$_{1-6}$ alkyl, or R$^8$ and R$^9$ with the carbon attached thereto form a C$_{1-6}$ cycloalkyl, and R$^{10}$ is H, cyano, heteroaryl, —C(O)NR$^{12}$R$^{13}$, or alkylheteroaryl; or R$^9$ and R$^{10}$ form a heterocyclyl substituted with oxo and independently optionally substituted with one to four halo or C$_{1-6}$ alkyl;

R$^8$ and R$^9$ with the carbon attached thereto form a C(O) and R$^{10}$ is C$_{1-6}$ alkyl, amino, C$_{1-6}$ alkylamino, C$_{1-6}$ haloalkyl, or heterocyclyl optionally substituted with one or more halo;

R$^{12}$ and R$^{13}$ are each independently H, C$_{1-6}$ alkyl, C$_{2-6}$ alkenyl, C$_{2-6}$ alkynyl, cycloalkyl, heterocyclyl, aryl, heteroalkyl, or heteroaryl, wherein each of C$_{1-6}$ alkyl, C$_{2-6}$ alkenyl, C$_{2-6}$ alkynyl, cycloalkyl, heterocyclyl, aryl, heteroalkyl, and heteroaryl is optionally substituted, or R$^{12}$ and R$^{13}$ together with the nitrogen to which they are attached, form a three- to six-membered optionally substituted heterocyclyl;

Z is O or NR$^{15}$;

R$^{14}$ is halo or C$_{1-6}$ alkyl;

R$^{15}$ is H or C$_{1-6}$ alkyl; and and q is 0 to 3.

In certain embodiments, Cy is optionally independently substituted with one to two halo, hydroxy, or heteroaryl.

In certain embodiments of Formula (I) or (II), or any subformula thereof, R$^{10}$ is heteroaryl, cyano, alkylheteroaryl, or —C(O)NR$^{12}$R$^{13}$. In certain embodiments of Formula (I) or (II), or any subformula thereof, R$^{10}$ is 1H-1,2,4-triazol-3-yl, cyano, 2-methyl-2H-tetrazol-5-yl, 1H-1,2,4-triazol-1-yl, or —C(O)NH$_2$. In certain embodiments of Formula (I) or (II), or any subformula thereof, R$^{10}$ is H, heteroaryl, or cyano. In certain embodiments of Formula (I) or (II), or any subformula thereof R$^{10}$ is H, 1H-1,2,4-triazol-3-yl, or cyano. In certain embodiments of Formula (I) or (II), or any subformula thereof, R$^{10}$ is 1-morpholinyl, 3,3-difluoropyrrolidin-1-yl, methylamino, or 8-oxa-3-azabicyclo[3.2.1]octan-3-yl.

In certain embodiments of Formula (I) or (II), or any subformula thereof, R$^{10}$ is 1H-1,2,4-triazol-3-yl, cyano, 2-methyl-2H-tetrazol-5-yl, or 1H-1,2,4-triazol-1-yl.

In certain embodiments of Formula (I) or (II), or any subformula thereof, R$^{10}$ is H, 1H-1,2,4-triazol-3-yl, or cyano.

In certain embodiments of Formula (I) or (II), or any subformula thereof, R$^{10}$ is 1H-1,2,4-triazol-3-yl, or cyano.

In certain embodiments of Formula (I) or (II), or any subformula thereof, R$^{10}$ is 1-morpholinyl, 3,3-difluoropyrrolidin-1-yl, or 8-oxa-3-azabicyclo[3.2.1]octan-3-yl.

In certain embodiments of Formula (I) or (II), or any subformula thereof, R$^{10}$ is 1H-1,2,4-triazol-1-yl or cyano.

In certain embodiments of Formula (I) or (II), or any subformula thereof, R$^{10}$ is C$_{1-6}$ alkyl.

In certain embodiments of Formula (I) or (II), or any subformula thereof, R$^{12}$ and R$^{13}$ are H.

In some embodiments, provided is a compound of formula (I'a):

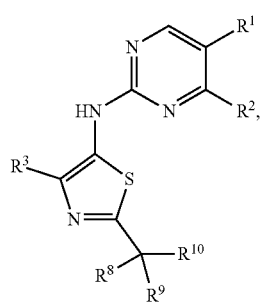

(I'a)

or a pharmaceutically acceptable salt, prodrug, stereoisomer, or a mixture of stereoisomers thereof, wherein R$^1$, R$^2$, R$^3$, R$^8$, R$^9$ and R$^{10}$ are as defined herein for the compound of formula (I').

In some embodiments, provided is a compound of formula (I'aa):

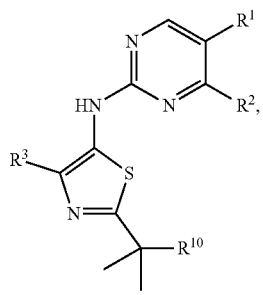

(I'aa)

or a pharmaceutically acceptable salt, prodrug, stereoisomer, or a mixture of stereoisomers thereof, wherein $R^1$, $R^2$, $R^3$, and $R^{10}$ are as defined herein for the compound of formula (I'). In some embodiments, $R^{10}$ is 1H-1,2,4-triazol-3-yl, cyano, 2-methyl-2H-tetrazol-5-yl, or 1H-1,2,4-triazol-1-yl.

In some embodiments, provided is a compound of formula (I'ab):

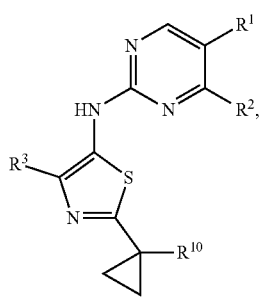

(I'ab)

or a pharmaceutically acceptable salt, prodrug, stereoisomer, or a mixture of stereoisomers thereof, wherein $R^1$, $R^2$, $R^3$ and $R^{10}$ are as defined herein for the compound of formula (I'). In some embodiments, $R^{10}$ is H, 1H-1,2,4-triazol-3-yl, or cyano. In some embodiments, $R^{1'}$ is 1H-1,2,4-triazol-3-yl, or cyano.

In some embodiments, provided is a compound of formula (I'ac):

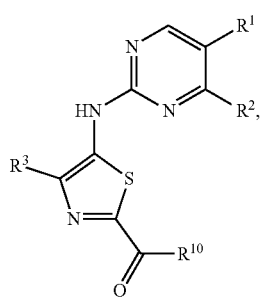

(I'ac)

or a pharmaceutically acceptable salt, prodrug, stereoisomer, or a mixture of stereoisomers thereof, wherein $R^1$, $R^2$, $R^3$ and $R^{10}$ are as defined herein for the compound of formula (I'). In some embodiments, $R^{10}$ is 1-morpholinyl, 3,3-difluoropyrrolidin-1-yl, or 8-oxa-3-azabicyclo[3.2.1]octan-3-yl.

In some embodiments, provided is a compound of formula (I'ad):

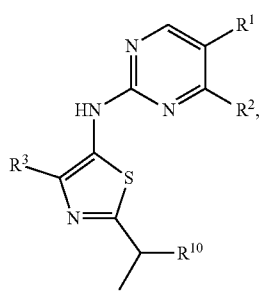

(I'ad)

or a pharmaceutically acceptable salt, prodrug, stereoisomer, or a mixture of stereoisomers thereof, wherein $R^1$, $R^2$, $R^3$ and $R^{10}$ are as defined herein for the compound of formula (I'). In some embodiments, $R^{10}$ is 1H-1,2,4-triazol-1-yl or cyano.

In some embodiments, provided is a compound of formula (I'ae):

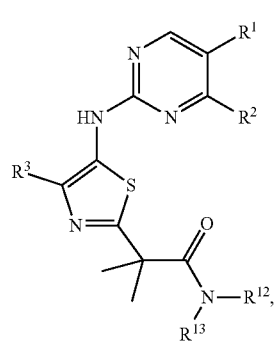

(I'ae)

or a pharmaceutically acceptable salt, prodrug, stereoisomer, or a mixture of stereoisomers thereof, wherein $R^1$, $R^2$, $R^3$, $R^{12}$ and $R^{13}$ are as defined herein for the compound of formula (I'). In some embodiments, $R^{12}$ and $R^{13}$ are H.

In some embodiments, provided is a compound of formula (I'af):

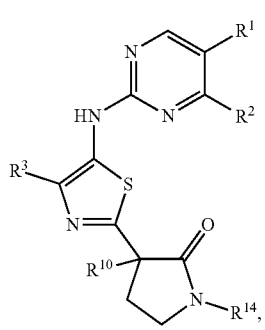

(I'af)

or a pharmaceutically acceptable salt, prodrug, stereoisomer, or a mixture of stereoisomers thereof, wherein $R^1$, $R^2$, $R^3$ and $R^{10}$ are as defined herein for the compound of formula (I') and $R^{14}$ is H or $C_{1-6}$ alkyl. In some embodiments, $R^{10}$ is $C_{1-6}$ alkyl.

In some embodiments, provided is a compound of formula (I'ag):

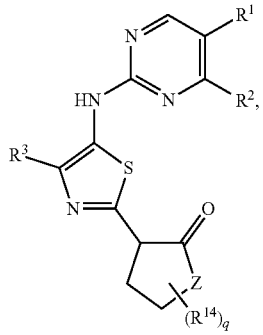

(I'ag)

or a pharmaceutically acceptable salt, prodrug, deuterated analog, stereoisomer, or a mixture of stereoisomers thereof, wherein $R^1$, $R^2$, and $R^3$ are as defined herein for the compound of formula (I') Z is O or $NR^{15}$, $R^{14}$ is halo or $C_{1-6}$ alkyl, $R^{15}$ is H or $C_{1-6}$ alkyl, and q is 0 to 3. In some embodiments, Z is O. In some embodiments, Z is $NR^{15}$. In some embodiments, Z is NH. In some embodiments, $R^3$ is halo. In some embodiments, q is 1 or 2 and $R^{14}$ is $CD_3$.

In some embodiments, provided is a compound of formula (I'b):

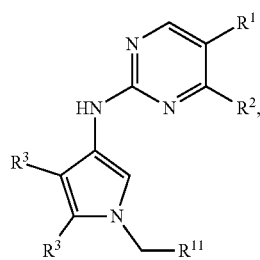

(I'b)

or a pharmaceutically acceptable salt, prodrug, stereoisomer, or a mixture of stereoisomers thereof, wherein $R^1$, $R^2$ and $R^3$ are as defined herein for the compound of formula (I') and $R^{11}$ is H, alkylsulfonyl, or alkylheteroaryl. In some embodiments, $R^{11}$ is H, 1-methyl-1H-pyrazol-3-yl, or methylsulfonyl.

In some embodiments, provided is a compound of formula (I'c):

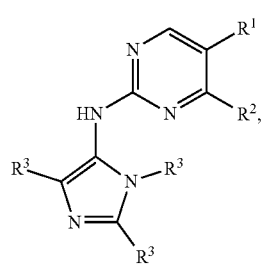

(I'c)

or a pharmaceutically acceptable salt, prodrug, stereoisomer, or a mixture of stereoisomers thereof, wherein $R^1$, $R^2$ and $R^3$ are as defined herein for the compound of formula (I').

In some embodiments, provided is a compound of formula (I'd):

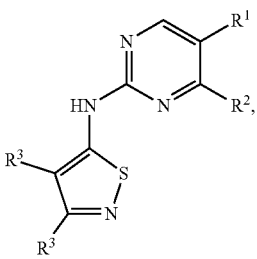

(I'd)

or a pharmaceutically acceptable salt, prodrug, stereoisomer, or a mixture of stereoisomers thereof, wherein $R^1$, $R^2$ and $R^3$ are as defined herein for the compound of formula (I').

In some embodiments, provided is a compound of formulae (I), (I'), (I'a), (I'aa), (I'ab), (I'ac), (I'ad), (I'b), (I'c), or (I'd), or a pharmaceutically acceptable salt, prodrug, stereoisomer, or a mixture of stereoisomers thereof, wherein $R^1$ is halo, cyano, $C_{1-6}$ alkyl, or $C_{1-6}$ haloalkyl and other variables are as defined herein. In some embodiments, provided is a compound of formulae (I), (I'), (I'a), (I'aa), (I'ab), (I'ac), (I'ad), (I'ae), (I'af), (I'b), (I'c), or (I'd), or a pharmaceutically acceptable salt, prodrug, stereoisomer, or a mixture of stereoisomers thereof, wherein $R^1$ is halo, cyano, $C_{1-6}$ alkyl, or $C_{1-6}$ haloalkyl and other variables are as defined herein. In some embodiments, $R^1$ is halo or $C_{1-6}$ haloalkyl. In some embodiments, $R^1$ is bromo. In some embodiments, $R^1$ is $C_{1-6}$ fluoroalkyl. In some other embodiments, $R^1$ is —$CF_3$. In some other embodiments, $R^1$ is bromo or —$CF_3$.

In some embodiments, provided is a compound of formulae (I), (I'), (I'a), (I'aa), (I'ab), (I'ac), (I'ad), (I'b), (I'c), or (I'd), or a pharmaceutically acceptable salt, prodrug, stereoisomer, or a mixture of stereoisomers thereof, wherein $R^2$ is optionally substituted cycloalkyl or —$N(R^5)(R^6)$. In some embodiments, $R^2$ is cyclopropyl, —$NH(CH_3)$, or —$NH(CH_2CH_3)$ and other variables are as defined herein. In some embodiments, provided is a compound of formulae (I), (I'), (I'a), (I'aa), (I'ab), (I'ac), (I'ad), (I'ae), (I'af), (I'b), (I'c), or (I'd), or a pharmaceutically acceptable salt, prodrug, stereoisomer, or a mixture of stereoisomers thereof, wherein $R^2$ is optionally substituted cycloalkyl, $C_{1-6}$ alkoxy or —$N(R^5)(R^6)$. In some embodiments, $R^2$ is cyclopropyl, —$NH(CH_3)$, or —$NH(CH_2CH_3)$ and other variables are as defined herein. In some embodiments, $R^2$ is cyclopropyl, —$NH(CH_3)$, —$NH(CH_2CH_3)$ or —$NH(cyclopropyl)$ and other variables are as defined herein. In some embodiments, $R^2$ is cycloalkyl. In some embodiments, $R^2$ is cyclopropyl. In some embodiments, $R^2$ is $C_{1-6}$ alkoxy. In some embodiments, $R^2$ is —$OCH_3$. In some embodiments, $R^2$ is —$N(R^5)(R^6)$ and other variables are as defined herein. In some embodiments, $R^2$ is —$NH(CH_3)$ and other variables are as defined herein. In some embodiments, $R^2$ is —$NH(CH_2CH_3)$ and other variables are as defined herein. In some embodiments, $R^2$ is —$NH(cyclopropyl)$ and other variables are as defined herein. In some embodiments, $R^2$ is —$NH(CH_3)$, —$NH(CH_2CH_3)$, —$NH(CH_2CHF_2)$, —$NH(cyclopropyl)$, or —$OCH_3$.

In some embodiments, provided is a compound of formulae (I), (I'), (I'a), (I'aa), (I'ab), (I'ac), (I'ad), (I'ae), (I'af), (I'b), (I'c), or (I'd), or a pharmaceutically acceptable salt, prodrug, stereoisomer, or a mixture of stereoisomers thereof, wherein each $R^3$ independently is halo, cyano, $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroarylalkyl, alkylheteroarylalkyl, heteroarylcycloalkyl, alkylheteroarylcycloalkyl, amido, amidoalkyl, or —C(O)$R^7$, wherein each of $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroarylalkyl, alkylheteroarylalkyl, heteroarylcycloalkyl, and alkylheteroarylcycloalkyl is independently optionally substituted. In some embodiments, each $R^3$ independently is H, $C_{1-6}$ alkyl, halo, or cycloalkyl and other variables are as defined herein.

In some embodiments, provided is a compound of formulae (I), (I'), (I'a), (I'aa), (I'ab), (I'ac), (I'ad), (I'b), (I'c), or (I'd), or a pharmaceutically acceptable salt, prodrug, stereoisomer, or a mixture of stereoisomers thereof, wherein each $R^3$ independently is halo, cyano, $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroarylalkyl, alkylheteroarylalkyl, heteroarylcycloalkyl, alkylheteroarylcycloalkyl, amido, or —C(O)$R^7$, wherein each of $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroarylalkyl, alkylheteroarylalkyl, heteroarylcycloalkyl, and alkylheteroarylcycloalkyl is independently optionally substituted. In some embodiments, provided is a compound of formulae (I), (I'), (I'a), (I'aa), (I'ab), (I'ac), (I'ad), (I'ae), (I'af), (I'b), (I'c), or (I'd), or a pharmaceutically acceptable salt, prodrug, stereoisomer, or a mixture of stereoisomers thereof, wherein each $R^3$ independently is halo, cyano, $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroarylalkyl, alkylheteroarylalkyl, heteroarylcycloalkyl, alkylheteroarylcycloalkyl, amido, or —C(O)$R^7$, wherein each of $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroarylalkyl, alkylheteroarylalkyl, heteroarylcycloalkyl, and alkylheteroarylcycloalkyl is independently optionally substituted. In some embodiments, each $R^3$ independently is H, $C_{1-6}$ alkyl, halo, or cycloalkyl and other variables are as defined herein.

In some embodiments, each $R^3$ independently is H, $C_{1-6}$ alkyl, halo, heterocyclyl, or cycloalkyl, wherein the alkyl, heterocyclyl and cycloalkyl are each independently optionally substituted by one or more oxo, halo, $C_{1-6}$ alkyl, $C_{1-6}$ alkyl wherein 1-6 hydrogens have been replaced by deuterium, $C_{1-6}$ haloalkyl, cyano, heterocyclyl, heteroaryl, —C(O)NR$^{12}$R$^{13}$, or alkylheteroaryl. In some embodiments, each $R^3$ independently is $C_{1-6}$ alkyl, heterocyclyl, or cycloalkyl, wherein the alkyl, heterocyclyl and cycloalkyl are each independently optionally substituted by one or more oxo, halo, $C_{1-6}$ alkyl, $C_{1-6}$ alkyl wherein 1-6 hydrogens have been replaced by deuterium, $C_{1-6}$ haloalkyl, cyano, heterocyclyl, heteroaryl, —C(O)NR$^{12}$R$^{13}$, or alkylheteroaryl. In certain embodiments, the $C_{1-6}$ alkyl wherein 1-6 hydrogens have been replaced by deuterium is —CD$_3$.

In some embodiments, m is 2 and one $R^3$ is halo and one $R^3$ is pyrrolidone optionally substituted by one or more —CD$_3$.

In some embodiments, each $R^3$ independently is H, chloro, cyano, methyl,

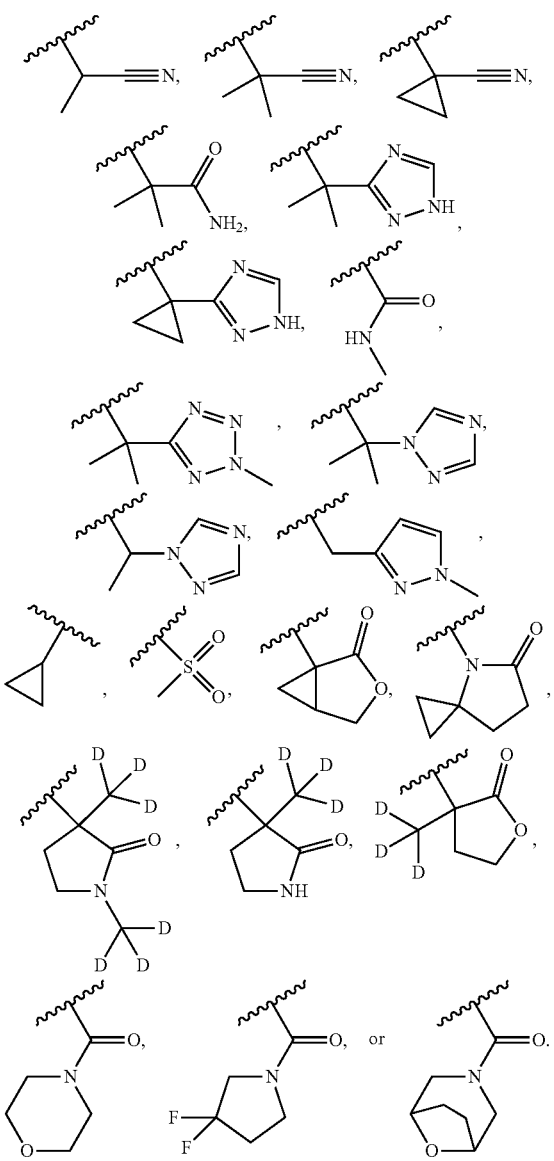

In some embodiments, $R^1$ is halo or $C_{1-6}$ haloalkyl; $R^2$ is cycloalkyl, $C_{1-6}$ alkoxy, or —N(R')(R$^6$) each $R^3$ is independently H, halo, cyano, $C_{1-6}$ alkyl, $C_{1-6}$ cyanoalkyl, cycloalkyl, cyanocycloalkyl, heterocyclyl, heteroarylalkyl, alkylheteroarylalkyl, heteroarylcycloalkyl, ($C_{1-6}$ alkyl)NHCO, amidoalkyl, —C(O)R$^7$, or heterocyclyl substituted with oxo and one to two $C_{1-6}$ alkyl; and R$^1$ and R$^6$ are each independently H, cycloalkyl, and $C_{1-6}$ alkyl optionally substituted with one to three halo; and $R^7$ is heterocyclyl optionally substituted with one to three halo.

In some embodiments, when 1) $R^4$ is $C_{1-6}$ alkyl, $C_{1-6}$ alkoxy, or heterocyclyl or 2) $R^{17}$ is $C_{1-6}$ alkyl, or 3) $R^2$ is cycloalkyl, or 4) $R^3$ is $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, $C_{1-6}$ alkylsulfonyl, $C_{1-6}$ alkylsulfonylalkyl, cycloalkyl, cyanocycloalkyl, cycloalkylalkyl, heterocyclyl, heterocyclylalkyl, alkylheterocyclylalkyl, aryl, arylalkyl, heteroaryl, heteroarylalkyl, alkylheteroarylalkyl, heteroarylcycloalkyl, or alkylheteroarylcycloalkyl, or 5) $R^{12}$ and $R^{13}$ are $C_{1-6}$ alkyl, $C_{2-6}$ alkenyl, $C_{2-6}$ alkynyl, cycloalkyl, heterocyclyl, aryl, heteroalkyl, or heteroaryl, or 6) $R^{12}$ and $R^{13}$ together with the nitrogen to which they are attached, form a three- to six-membered heterocyclyl, each $R^2$, $R^3$, $R^4$, $R^{17}$, $R^{12}$ and $R^{13}$ is independently optionally substituted with one or more substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si($R^y$)$_3$ wherein each $R^y$ is independently hydrogen, alkyl, alkenyl, alkynyl, heteroalkyl, cycloalkyl, aryl, heteroaryl or heterocyclyl.

In some embodiments, when $R^5$ or $R^6$ is $C_{1-6}$ alkyl, each $R^5$ or $R^6$ is independently optionally substituted with one or more substituents independently selected from alkenyl, alkynyl, alkoxy, alkylthio, acyl, amido, amino, amidino, aryl, azido, carbamoyl, carboxyl, carboxyl ester, cyano, cycloalkyl, guanadino, halo, haloalkoxy, hydroxyalkyl, heteroalkyl, heteroaryl, hydrazine, hydrazone, imino, imido, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si($R^y$)$_3$ wherein each $R^y$ is independently hydrogen, alkyl, alkenyl, alkynyl, heteroalkyl, cycloalkyl, aryl, heteroaryl or heterocyclyl.

In some embodiments, when $R^5$ and $R^6$ together with the atom to which they are attached form a heterocyclyl which is optionally substituted with one or more substituents independently selected from $C_{2-6}$ alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si($R^y$)$_3$ wherein each $R^y$ is independently hydrogen, alkyl, alkenyl, alkynyl, heteroalkyl, cycloalkyl, aryl, heteroaryl or heterocyclyl.

In any of the above embodiments, the compound may be a pharmaceutically acceptable salt, tautomer, stereoisomer, mixture of stereoisomers, prodrug, or deuterated analog thereof.

In one embodiment, a compound may be selected from those compounds in Table 1. Also included within the disclosure are pharmaceutically acceptable salts, prodrugs, stereoisomers, or a mixture of stereoisomers thereof. In certain embodiments, provided are compounds of Table 1 and Table IA for use in the methods described herein.

TABLE 1

| No. | Structure |
|---|---|
| 1 | 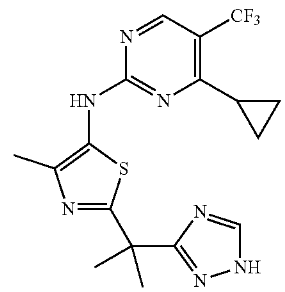 [SMILES: Cc1nc(C(C)(C)c2nc[nH]n2)sc1Nc1ncc(C(F)(F)F)c(C2CC2)n1] |
| 2 | 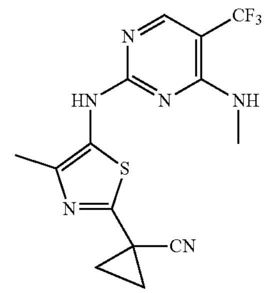 [SMILES: CNc1nc(Nc2sc(C3(C#N)CC3)nc2C)ncc1C(F)(F)F] |
| 3 | 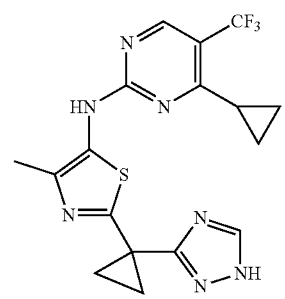 [SMILES: Cc1nc(C2(c3nc[nH]n3)CC2)sc1Nc1ncc(C(F)(F)F)c(C2CC2)n1] |
| 4 | 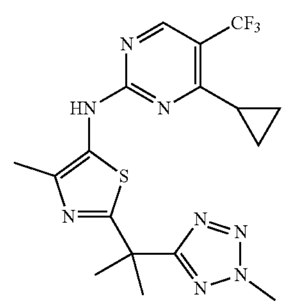 [SMILES: Cc1nc(C(C)(C)c2nnn(C)n2)sc1Nc1ncc(C(F)(F)F)c(C2CC2)n1] |
| 5 | 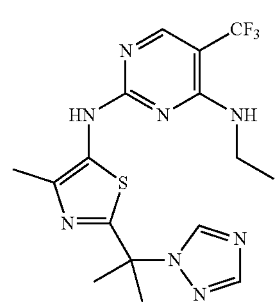 [SMILES: CCNc1nc(Nc2sc(C(C)(C)n3cncn3)nc2C)ncc1C(F)(F)F] |

TABLE 1-continued

| No. | Structure |
|---|---|
| 6 | (structure) |
| 7 | (structure) |
| 8 | (structure) |
| 9 | (structure) |
| 10 | (structure) |
| 11 | (structure) |
| 12 | (structure) |
| 13 | (structure) |
| 14 | (structure) |

TABLE 1-continued

| No. | Structure |
|---|---|
| 15 | (structure) |
| 16 | (structure) |
| 17 | (structure) |
| 18 | (structure) |
| 19 | (structure) |
| 20 | (structure) |
| 21 | (structure) |
| 22 | (structure) |
| 23 | (structure) |

TABLE 1-continued

| No. | Structure |
|---|---|
| 24 | (structure) |
| 25 | (structure) |
| 26 | (structure) |
| 27 | (structure) |
| 28 | (structure) |
| 29 | (structure) |
| 30 | (structure) |
| 31 | (structure) |

TABLE 1-continued

| No. | Structure |
|---|---|
| 32 | (structure) |
| 33 | (structure) |
| 34 | (structure) |
| 35 | (structure) |
| 36 | (structure) |
| 37 | (structure) |
| 38 | (structure) |
| 39 | (structure) |
| 40 | (structure) |

TABLE 1-continued

| No. | Structure |
|---|---|
| 41 | (5-bromopyrimidin-2-yl / 4-cyclopropylamino, chlorothiazole, 2-methylpropanamide) |
| 42 | (trifluoromethylpyrimidin-methylamino, chlorothiazole, CD2H-pyrrolidinone) — First eluting isomer |
| 43 | (trifluoromethylpyrimidin-methylamino, chlorothiazole, CD2H-pyrrolidinone) — Second eluting isomer |
| 44 | (trifluoromethylpyrimidin-methylamino, chlorothiazole, CH3-pyrrolidinone N-CD3) — First eluting isomer |
| 45 | (trifluoromethylpyrimidin-methylamino, chlorothiazole, CD2H-pyrrolidinone N-CD3) — Second eluting isomer |
| 46 | (trifluoromethylpyrimidin-ethylamino, chlorothiazole, CD2H-pyrrolidinone N-CD3) — First eluting isomer |
| 47 | (trifluoromethylpyrimidin-ethylamino, chlorothiazole, CD2H-pyrrolidinone N-CD3) — Second eluting isomer |

TABLE 1-continued
| No. | Structure |
|---|---|
| 48 | 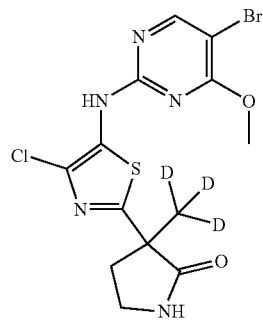 [SMILES: [2H]C([2H])([2H])C1(c2nc(Cl)c(Nc3ncc(Br)c(OC)n3)s2)CCNC1=O]<br>First eluting isomer |
| 49 | 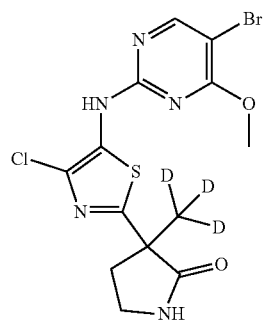 [SMILES: [2H]C([2H])([2H])C1(c2nc(Cl)c(Nc3ncc(Br)c(OC)n3)s2)CCNC1=O]<br>Second eluting isomer |
| 50 | 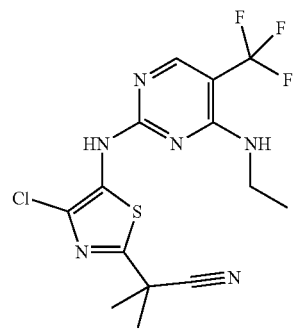 [SMILES: CCNc1nc(Nc2sc(C(C)(C)C#N)nc2Cl)ncc1C(F)(F)F] |
| 51 | 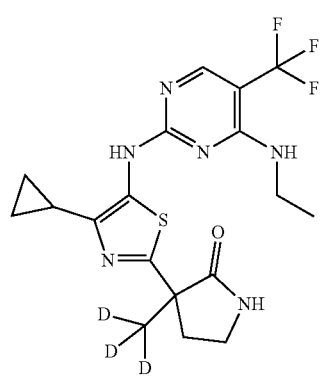 [SMILES: [2H]C([2H])([2H])C1(c2nc(C3CC3)c(Nc3ncc(C(F)(F)F)c(NCC)n3)s2)CCNC1=O]<br>First eluting isomer |
TABLE 1-continued
| No. | Structure |
|---|---|
| 52 | 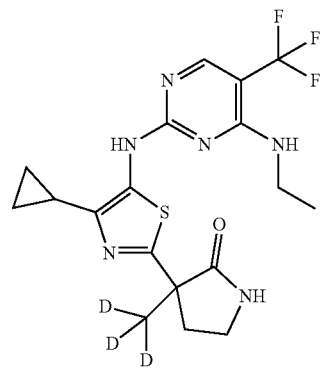 [SMILES: [2H]C([2H])([2H])C1(c2nc(C3CC3)c(Nc3ncc(C(F)(F)F)c(NCC)n3)s2)CCNC1=O]<br>Second eluting isomer |
| 53 | 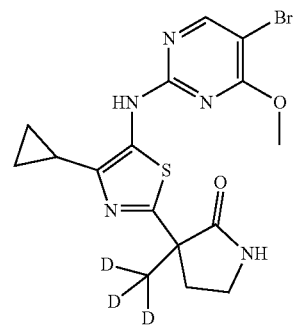 [SMILES: [2H]C([2H])([2H])C1(c2nc(C3CC3)c(Nc3ncc(Br)c(OC)n3)s2)CCNC1=O]<br>First eluting isomer |
| 54 | 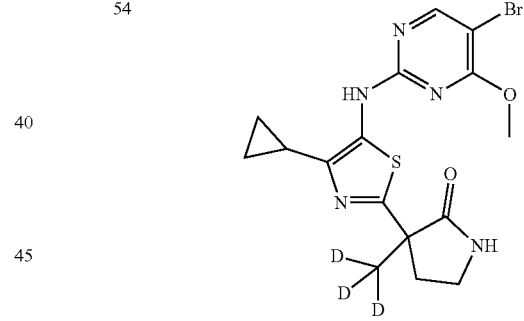<br>Second eluting isomer |
| 55 | 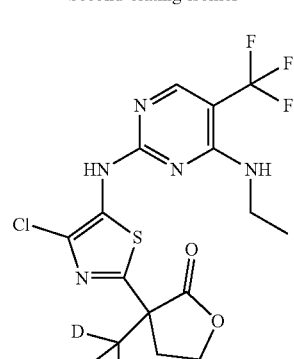<br>First eluting isomer |

TABLE 1-continued
| No. | Structure |
|-----|-----------|
| 56 | 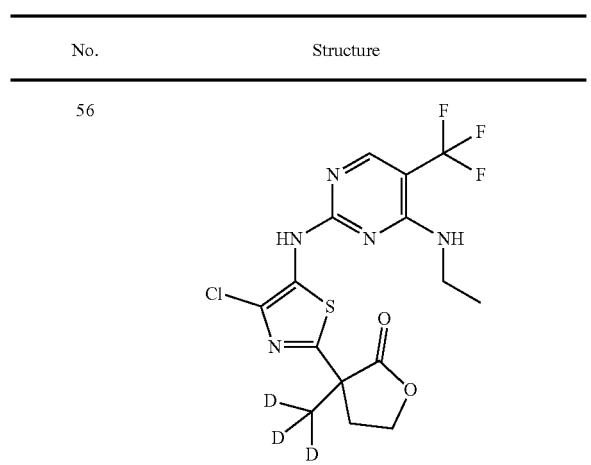
Second eluting isomer |
| 57 | 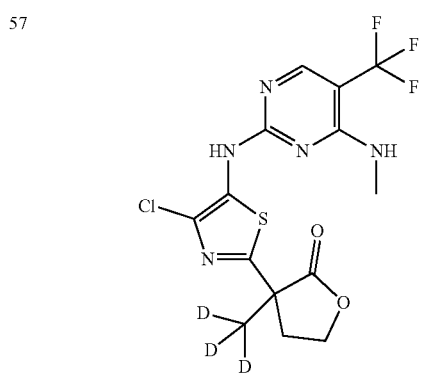
First eluting isomer |
| 58 | 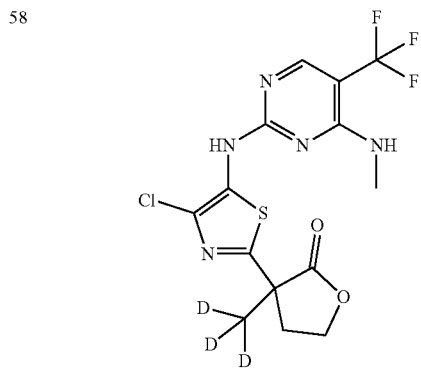
Second eluting isomer |
TABLE 1-continued
| No. | Structure |
|-----|-----------|
| 59 | 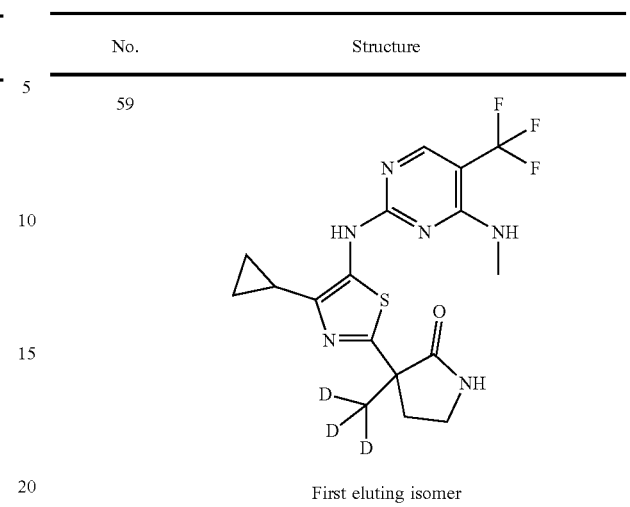
First eluting isomer |
| 60 | 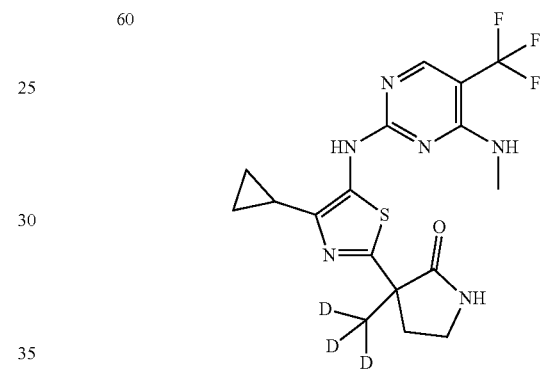
Second eluting isomer |
| 61 | 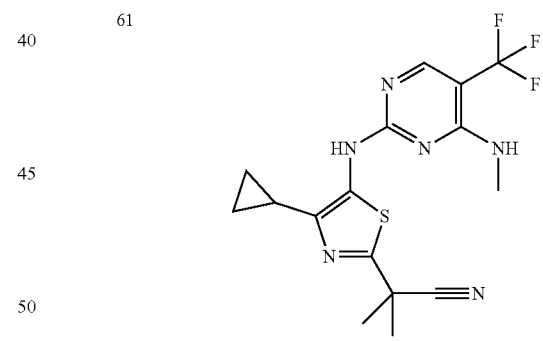 |
| 62 | 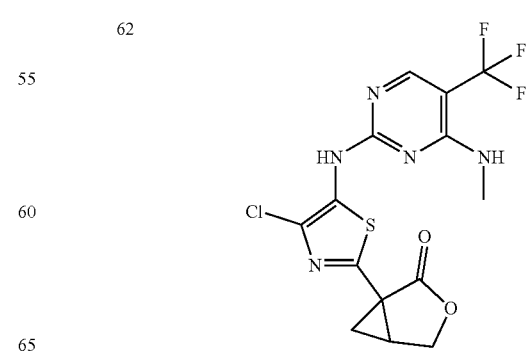 |

TABLE 1-continued

| No. | Structure |
|---|---|
| 63 | (structure) |
| 64 | (structure) |
| 65 | (structure) |
| 66 | (structure) |

Specific stereoisomers and regioisomers contemplated include the following in Table 1A.

TABLE 1A

| Structure |
|---|
| (structure) |
| (structure) |
| (structure) |
| (structure) |

TABLE 1A-continued

Structure

TABLE 1A-continued

Structure

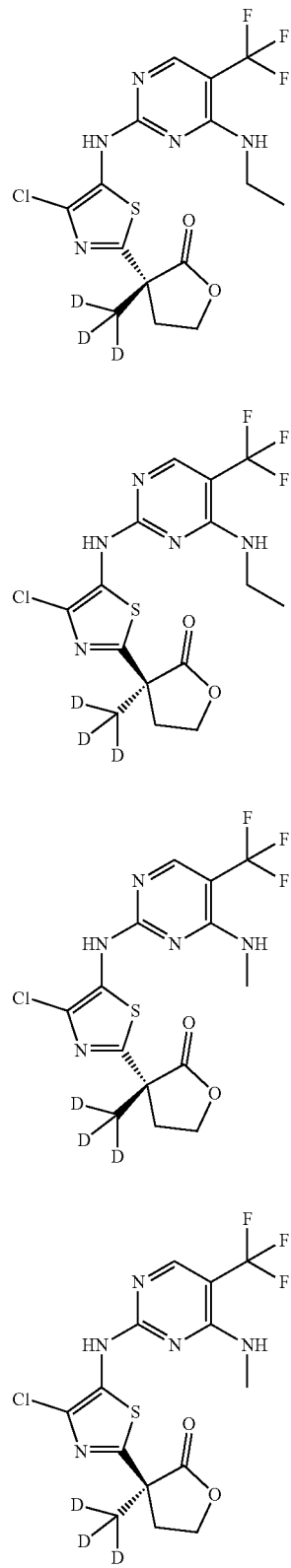

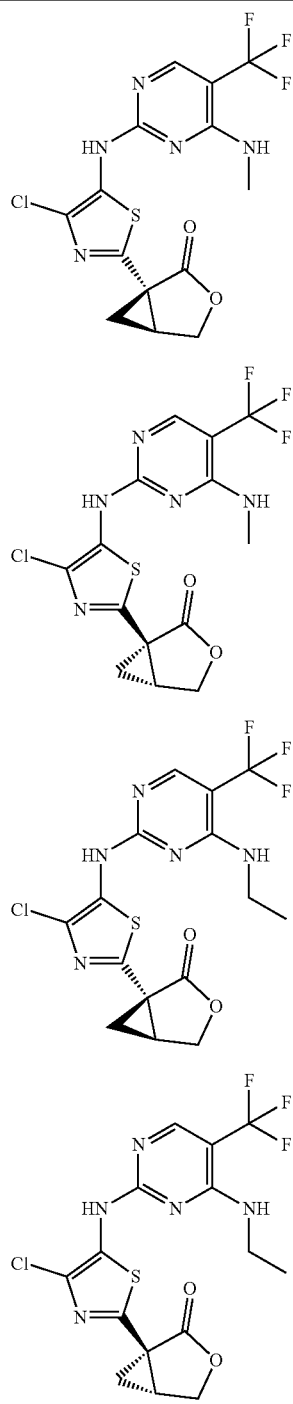

It is understood that any embodiment of the compounds of formula (I), (I'), (I'a), (I'aa), (I'ab), (I'ac), (I'ad), (I'ae), (I'af), (I'b), (I'c), or (I'd), including substructures thereof, and any of the specific substituents set forth herein in the compounds of formula (I), as set forth above, or any other formula provided herein, may be independently combined with other embodiments and/or substituents of compounds of formula (I) to form embodiments of the disclosures not specifically set forth above. In addition, in the event that a list of substituents is listed for any particular R group in a particular embodiment and/or claim, it is understood that each individual substituent may be deleted from the particular embodiment and/or claim and that the remaining list of substituents will be considered to be within the scope of the disclosure. It is understood that in the present description, combinations of substituents and/or variables of the depicted formulae are permissible only if such contributions result in stable compounds.

4. Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject, and disease or condition being treated, the weight and age of the subject, the severity of the disease or condition, and the manner of administering, which can readily be determined by one of ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

LRRK2 has been associated with the transition from mild cognitive impairment to Alzheimer's disease; L-Dopa induced dyskinesia (Hurley et al., Eur. J, Neurosci., Vol. 26, 2007, 171-177); CNS disorders associated with neuroprogenitor cell proliferation and migration, and regulation of LRRK2 may have utility in improving neurological outcomes following ischemic injury, and stimulating restoration of CNS function following neuronal injury such as ischemic stroke, traumatic brain injury, or spinal cord injury (Milosevic et al., Neurodegen., Vol. 4, 2009, 25; See Zhang et al., J. Neurosci. Res. Vol. 88, 2010, 3275-3281); Parkinson's disease, Alzheimer's disease, multiple sclerosis, and HIV-induced dementia (See Milosevic et al., Mol. Neurodegen., Vol. 4, 2009, 25); kidney, breast, prostate (e.g. solid tumor), blood and lung cancer, and acute myeologenouse leukemia (AML); lymphomas and leukemias (See Ray et al., J. Immunolo., Vol. 230, 2011, 109); multiple myeoloma (Chapman et al., Nature, Vol. 471, 2011, 467-472); papillary renal and thyroid carcinomas; multiple myeloma (Chapman et al., Nature, Vol. 471, 2011, 467-472); diseases of the immune system, including rheumatoid arthritis, systemic lupus erythematosus autoimmune hemolytic anemia, pure red cell aplasia, idiopathic thrombocytopenic pupura (ITP), Evans syndrome, vasculitis, bullous skin disorders, type 1 diabetes mellitus, Sjogren's syndrome, Delvic's disease, and inflammatory myopathies (Nakamura et al., DNA Res. Vol. 13(4), 2006, 169-183; See Engel et al., Pharmacol. Rev. Vol. 63, 2011, 127-156; Homam et al., J. Clin. Neuromuscular Disease, Vol. 12, 2010, 91-102); ankylosing spondylitis and leprosy infection (DAnoy et al., PLoS Genetics, Vol. 6(12), 2010, e1001195, 1-5; see Zhang et al., N. Eng. J. Med. Vol. 361, 2009, 2609-2618); alpha-synucleinopathies, taupathies (See Li et al., 2010 Neurodegen. Dis. Vol. 7, 2010, 265-271); Gaucher disease (See Westbroek et al., Trends. Mol. Med. Vol. 17, 2011, 485-493); tauopathy diseases characterized by hyperphosphorylation of Tau such as argyrophilic grain disease, Pick's disease, corticobasal degeneration, progressive supranuclear palsy, and inherited frontotemporal dementia and parkinsonism linked to chromosome 17 (See Goedert, M and Jakes, R, Biochemica et Biophysica Acta, Vol. 1739, 2005, 240-250); diseases characterized by diminished dopamine levels such as withdrawal symptoms/relapse associated with drug addiction (See Rothman et al., og. Brain Res., Vol. 172, 2008, 385); microglial proinflammatory responses (See Moehle et al., J. Neuroscience Vol. 32, 2012, 1602-1611); Crohn's disease pathogenesis (see Barrett et al., Nature Genetics, Vol. 40, 2008, 955-962); and amyotrophic lateral sclerosis (ALS).

It is suggested that increased LRRK2 activity may be characteristic of ALS. Significantly elevated levels of LRRK2 mRNA have been observed in fibroblasts of Niemann-Pick Type C (NPC) disease patients, indicating abnormal LRRK2 function may play a role in lysosomal disorders.

In another aspect, the present disclosure relates to a method of treating a disease or condition mediated, at least in part, by LRRK2. In particular, the disclosure provides methods for preventing or treating a disorder associated with LRRK2 in a mammal, comprising the step of administering to said mammal a therapeutically effective amount of a compound of formula (I) or therapeutic preparation of the present disclosure. In some embodiments, the disease or condition mediated, at least in part, by LRRK2 is a neurodegenerative disease, for example, a central nervous system (CNS) disorder, such as Parkinson's disease (PD), Alzheimer's disease (AD), dementia (including Lewy body dementia and cascular dementia), amyotrophic lateral sclerosis (ALS), age related memory dysfunction, mild cognitive impairment (e.g., including the transition from mild cognitive impairment to Alzheimer's disease), argyrophilic grain disease, lysosomal disorders (for example, Niemann-PickType C disease, Gaucher disease) corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, Huntington's disease (HD), and HIV-associated dementia (HAD). In other embodiments, the disorder is an ischemic disease of organs including but not limited to brain, heart, kidney, and liver.

In some other embodiments, the disease or condition mediated, at least in part, by LRRK2 is cancer. In certain specific embodiments, the cancer is thyroid, renal (including papillary renal), breast, lung, blood, and prostate cancers (e.g. solid tumor), leukemias (including acute myelogenous leukemia (AML)), or lymphomas. In some embodiments, the cancer is kidney cancer, breast cancer, prostate cancer, blood cancer, papillary cancer, lung cancer, acute myelogenous leukemia, or multiple myeloma.

In other embodiments, the presently disclosed compounds are used in methods for treatment of inflammatory disorders. In some embodiments, the disorder is an inflammatory disease of the intestines, such as Crohn's disease or ulcerative colitis (both generally known together as inflammatory bowel disease). In other embodiments, the inflammatory disease is leprosy, amyotrophic lateral sclerosis, rheumatoid arthritis, or ankylosing spondylitis. In some embodiments, the inflammatory disease is leprosy, Crohn's disease, inflammatory bowel disease, ulcerative colitis, amyotrophic lateral sclerosis, rheumatoid arthritis, or ankylosing spondylitis.

In other embodiments, the presently disclosed compounds are used in methods for treatment of multiple sclerosis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease, and inflammatory myopathies.

Other embodiments include methods for enhancing cognitive memory of a subject, the method comprising administering an effective amount of a composition comprising the compound of formula (I) to a subject in need thereof.

Other embodiments include use of the presently disclosed compounds in therapy. Some embodiments include their use in the treatment of a neurodegenerative disease, cancer, or an inflammatory disease.

In other embodiments, provided are the presently disclosed compounds for use in the treatment of Alzheimer's disease, L-Dopa induced dyskinesia, Parkinson's disease, dementia, ALS, kidney cancer, breast cancer, prostate cancer, blood cancer, papillary cancer, lung cancer, acute myelogenous leukemia, multiple myeloma, leprosy, Crohn's disease, inflammatory bowel disease, ulcerative colitis, amyotrophic lateral sclerosis, rheumatoid arthritis, or ankylosing spondylitis.

In other embodiments, provided is the use of the presently disclosed compounds for the manufacture of a medicament for treating a neurodegenerative disease, cancer, or an inflammatory disease.

In other embodiments, provided is the use of the presently disclosed compounds for the manufacture of a medicament for treating Alzheimer's disease, L-Dopa induced dyskinesia, Parkinson's disease, dementia, amyotrophic lateral sclerosis, kidney cancer, breast cancer, prostate cancer, blood cancer, papillary cancer, lung cancer, acute myelogenous leukemia, multiple myeloma, leprosy, Crohn's disease, inflammatory bowel disease, ulcerative colitis, amyotrophic lateral sclerosis, rheumatoid arthritis, or ankylosing spondylitis.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel, and in certain embodiments of the disclosure the term stroke refers to ischemic stroke or hemorrhagic stroke. The term "myocardial infarction" refers to a cardiovascular disorder characterized by localized necrosis resulting from obstruction of the blood supply.

In certain embodiments, the present disclosure relates to compounds for inhibiting cell death, wherein the compounds are represented by formulae (I), (I'), (I'a), (I'aa), (I'ab), (I'ac), (I'ad), (I'b), (I'c)) and (I'd). In certain embodiments, the compounds of the present disclosure are inhibitors of cell death. In any event, the compounds of the present disclosure preferably exert their effect on inhibiting cell death at a concentration less than about 50 micromolar, more preferably at a concentration less than about 10 micromolar, and most preferably at a concentration less than 1 micromolar.

5. Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

6. Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

7. Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate.

In other embodiments a dosage of between 0.5 and 60 mg/kg may be appropriate. In some embodiments, a dosage of from about 0.0001 to about 100 mg per kg of body weight per day, from about 0.001 to about 50 mg of compound per kg of body weight, or from about 0.01 to about 10 mg of compound per kg of body weight may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of formula (I) may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, four, or more times daily, using any suitable mode described above.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

8. Combination Therapy

In another aspect of the disclosure the compounds can be administered in combination with other agents, including (but not limited to) compounds that are apoptosis inhibitors; PARP poly(ADP-ribose) polymerase inhibitors; Src inhibitors; agents for the treatment of cardiovascular disorders; hypertension, hypercholesterolemia and type II diabetes; anti-inflammatory agents, anti-thrombotic agents; fibrinolytic agents; anti-platelet agents, lipid reducing agents, direct thrombin inhibitors; glycoprotein IIb/IIIa receptor inhibitors; calcium channel blockers; beta-adrenergic receptor blocking agents; cyclooxygenase (e.g., COX-1 and COX-2) inhibitors; angiotensin system inhibitor (e.g., angiotensin-converting enzyme (ACE) inhibitors); renin inhibitors; and/or agents that bind to cellular adhesion molecules and inhibit the ability of white blood cells to attach to such molecules (e.g., polypeptides, polyclonal and monoclonal antibodies).

In other embodiments, the compounds of the present disclosure can be administered in combination with an additional agent having activity for treatment of a neurodegenerative disease. For example, in some embodiments the compounds are administered in combination with one or more additional therapeutic agents useful for treatment of Parkinson's disease. In some embodiments, the additional therapeutic agent is L-dopa (e.g., Sinemet®), a dopaminergic agonist (e.g. Ropinerol or Pramipexole), a catechol-O-methyltransferase (COMT) inhibitor (e.g. Entacapone), a L-monoamine oxidase (MAO) inhibitor (e.g., selegiline or rasagiline) or an agent which increases dopamine release (e.g., Zonisamide).

The present disclosure also provides combinations of two or more compounds that inhibit cellular necrosis (e.g., a compound as disclosed herein and an additional agent for inhibiting necrosis). The present disclosure also provides combinations of one or more compounds that inhibit cellular necrosis combined with one or more additional agents or compounds (e.g., other therapeutic compounds for treating a disease, condition, or infection).

9. Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more formulas or compounds disclosed herein, may be accomplished as described in the following examples. If available, reagents may be purchased commercially, e.g. from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

It will also be appreciated that in each of the above schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

General Synthesis

The following General Reaction Scheme I illustrates a general method of making compounds of formula (I):

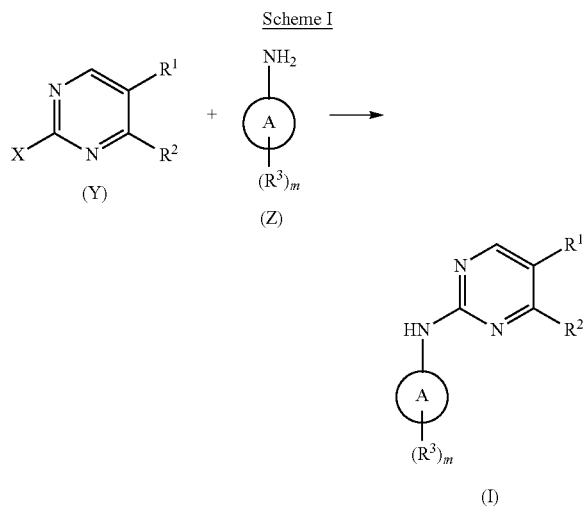

Referring to General Reaction Scheme I, compounds of formula (I) are prepared by coupling of a substituted pyrimidine of formula (Y) with an amine of formula (Z), wherein $R^1$, $R^2$, $R^3$, ring A and m are as defined herein and X is a leaving group. In certain embodiments, X is halo. Appropriate compounds of formula (Y) or (Z) can be prepared according to the more specific methods described in the Examples which follow or by methods known to one of skill in the art. Coupling of compounds of formula (Y) and (Z) in presence of an acid, provides a compound of formula (I). In some embodiments, the acid is toluene sulfonic acid or trifluroacetic acid. In some embodiments, coupling of compounds of formula (Y) and (Z) in the presence of a base provides a compound of formula (I). In some embodiments, the base is triethylamine.

In one embodiment, provided is a method of preparing a compound of formula (I) comprising coupling a compound of formula (Y) with a compound of formula (Z) under conditions to provide the compound of formula (I), wherein $R^1$, $R^2$, $R^3$, ring A and m are as defined herein and X is a leaving group. In certain embodiments, X is halo.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

General Experimental Methods:

All non-aqueous reactions were carried out in oven-dried or flame-dried glassware under nitrogen atmosphere. All chemicals were purchased from commercial vendors and used as is, unless otherwise specified. Reactions were magnetically stirred and monitored by thin layer chromatography (TLC) with 250 μm pre-coated silica gel plates, visualized either with UV, or in an iodine chamber. Flash column chromatography was performed using silica gel (100-200 mesh). Chemical shifts are reported relative to chloroform ($\delta 7.26$), methanol ($\delta 3.31$), or DMSO ($\delta 2.50$) for $^1$H NMR. HPLC analysis was performed on Shimadzu 20AB HPLC system with a photodiode array detector and Luna-C18(2) 2.0×50 mm, 5 μm column at a flow rate of 1.2 mL/min with a gradient solvent Mobile phase A (MPA, $H_2O$+0.037% (v/v) TFA): Mobile phase B (MPB, ACN+0.018% (v/v) TFA) (0.01 min, 10% MPB; 4 min, 80% MPB; 4.9 min, 80% MPB; 4.92 min, 10% MPB; 5.5 min, 10% MPB). LCMS was detected under 220 and 254 nm or used evaporative light scattering (ELSD) detection as well as positive electrospray ionization (MS). Semi-preparative HPLC was performed by either acidic or neutral condition. Acidic: Luna C18 100×30 mm, 5 μm; MPA: HC/$H_2O$=0.04%, or formic acid/$H_2O$=0.2% (v/v); MPB: ACN. Neutral: Waters Xbridge 150×25, 5 μm; MPA: 10 mM $NH_4HCO_3$ in $H_2O$; MPB: ACN. Gradient for both conditions: 10% of MPB to 80% of MPB within 12 min at a flow rate of 20 mL/min, then 100% MPB over 2 min, 10% MPB over 2 min, UV detector.

Compound Preparation

Where the preparation of starting materials is not described, these are commercially available, known in the literature or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is a Biotage Initiator. The actual power supplied varies during the course of the reaction in order to maintain a constant temperature.

Compounds were named by using either ChemBioDraw Ultra 13.0 or Chemaxon.

Example 1

Synthesis of 2-methyl-2-(4-methyl-5-((4-(methylamino)-5-(trifluoromethyl)pyrimidin-2-yl)amino)thiazol-2-yl)propanenitrile (17)

2-(4-methylthiazol-2-yl)acetonitrile: To a solution of cyanothioacetamide (2 g, 19.97 mmol) in DMF (50 mL) was slowly added triethylamine (2.02 g, 19.97 mmol) and 1-chloropropan-2-one (1.85 g, 19.97 mmol). A sticky solid rapidly was separated from the solution. The reaction mixture was heated at 40° C. for 1.5 h. The suspension was poured into water (110 mL) and extracted with EtOAc (3×150 mL). The combined organic phases were dried over $Na_2SO_4$ and concentrated under reduced pressure. The residue was purified by silica gel column chromatography eluting with PE/EtOAc (5/1 to EtOAc) to give 2-(4-methylthiazol-2-yl)acetonitrile as a yellow oil. $^1$H NMR (400 MHz, DMSO-$d_6$) δ ppm 2.34 (s, 3H) 4.49 (s, 2H) 7.26 (s, 1H).

2-methyl-2-(4-methylthiazol-2-yl)propanenitrile: To a solution of 2-(4-methylthiazol-2-yi)acetonitrile (1.8 g, 13.03 nmmol) in DMSO (20 mL) was added NaH (2.08 g, 52.12 mmol), and the mixture was stirred at 20° C. for 30 min. Under cooling to 0° C., MeI (7.40 g, 52.12 mmol) was added dropwise to the mixture, and the mixture was stirred at 20° C. for 1 h. The mixture was poured into the ice water (100 mL) and extracted with EtOAc (40 mL×3). The organic layer was washed by brine, dried and concentrated to give a residue. The residue was purified by silica gel column chromatography (ISCO®; 20 g SepaFlash® Silica Flash Column, Eluent of 0~50% Ethyl acetate/Petroleum ether gradient @75 mL/min) to give 2-methyl-2-(4-methylthiazol-2-yl)propanenitrile as a yellow oil. LCMS: RT 0.701 min, m/z=167.1 [M+H]$^+$.

2-methyl-2-(4-methyl-5-nitrothiazol-2-yl)propanenitrile: To a mixture of 2-methyl-2-(4-methylthiazol-2-yl)propanenitrile (500 mg, 3.01 mmol) in $Ac_2O$ (10 mL) was added $HNO_3$ (568.98 mg, 9.03 mmol) in $Ac_2O$ (1 mL) dropwise at 0° C. The mixture was stirred at 50° C. for 48 h. The reaction mixture was poured into ice water (60 mL), and extracted with EtOAc (20 mL×3). The combined organic layers were washed with brine (30 mL), dried over $Na_2SO_4$, filtered and concentrated under reduced pressure to give the crude product, used in the next step directly. 2-methyl-2-(4-methyl-5-nitrothiazol-2-yl)propanenitrile was obtained as a yellow oil. LCMS: RT 0.786 min, m/z=212.1 [M+H]$^+$.

2-(5-amino-4-methylthiazol-2-yl)-2-methylpropanenitrile: To a mixture of 2-methyl-2-(4-methyl-5-nitrothiazol-2-yl)propanenitrile (500 mg, 2.37 mmol) in EtOH (8 mL) and $H_2O$ (2 mL) was added Fe (660.98 mg, 11.83 mmol) and $NH_4Cl$ (633.05 mg, 11.83 mmol) at 0° C. The mixture was heated to 90° C. and stirred for 1 h. The mixture was filtered and the filtrate was concentrated, then added to EtOAc (100 mL) and washed by water (50 mL×2). The organic layer was washed by brine (50 mL), dried over $Na_2SO_4$, and concentrated to give a crude product which was used to the next step directly. 2-(5-amino-4-methylthiazol-2-yl)-2-methylpropanenitrile was obtained as a yellow oil. LCMS: RT 0.539 min, m/z=182.1 [M+H]$^+$.

2-methyl-2-(4-methyl-5-((4-(methylamino)-5-(trifluoromethyl)pyrimidin-2-yl)amino)thiazol-2-yl)propanenitrile (17): To a mixture of 2-(5-amino-4-methylthiazol-2-yl)-2-methylpropanenitrile (1-5, 150 mg, 413.77 μmol) and 2-chloro-N-methyl-5-(trifluoromethyl)pyrimidin-4-amine (87.54 mg, 413.77 μmol) in 1,4-dioxane (5 mL) was added TsOH.$H_2O$ (23.61 mg, 124.13 μmol) at 20° C. The mixture was heated to 80° C. and stirred for 2 h. The mixture was concentrated, purified by prep-HPLC (neutral condition) to give 2-methyl-2-(4-methyl-5-((4-(methylamino)-5-(trifluoromethyl)pyrimidin-2-yl)amino)thiazol-2-yl)propanenitrile (17). $^1$H NMR (400 MHz, CDCl$_3$) δ ppm 1.84 (s, 6H) 2.41 (s, 3H) 3.15 (br. s., 3H) 5.32 (br. s., 1H) 7.05 (br. s., 1H) 8.18 (s, 1H); HPLC: RT: 2.659 min; MS: m/z: 357.1 [M+H]$^+$.

Example 2

Synthesis of 1,3-dimethyl-4-((4-(methylamino)-5-(trifluoromethyl)pyrimidin-2-yl)amino)-1H-pyrrole-2-carbonitrile (14)

Ethyl 1,3-dimethyl-1H-pyrrole-2-carboxylate: To a solution of ethyl 3-methyl-1H-pyrrole-2-carboxylate (Ig, 6.53 mmol) in DMF (10 mL) was added NaH (313 mg, 7.84 mmol, 60% purity) in three portions at 0° C. The reaction mixture was stirred at 25° C. for 30 min. Then MeI (1.2 g, 8.49 mmol) was added to the mixture and stirred at 25° C. for 16 h. The reaction mixture was quenched by addition of $H_2O$ (60 mL) at 0° C., and then extracted with MTBE 150 mL (3×50 mL). The combined organic layers were washed with brine (3×50 mL), dried over $Na_2SO_4$, filtered and concentrated under reduced pressure to give ethyl 1,3-dimethylpyrrole-2-carboxylate (2-2) as a yellow oil. LCMS: RT 0.786 min, m/z=168.2 [M+H]$^+$. $^1$H NMR (400 MHz, CDCl$_3$): δ 1.37 (t, J=7.09 Hz, 3H), 2.34 (s, 3H), 3.87 (s, 3H), 4.31 (q, J=7.15 Hz, 2H), 5.96 (d, J=2.38 Hz, 1H), 6.65 (d, J=2.51 Hz, 1H).

Ethyl 1,3-dimethyl-4-nitro-1H-pyrrole-2-carboxylate: Ethyl 1,3-dimethylpyrrole-2-carboxylate (200 mg, 1.2 mmol) was added dropwise to HNO$_3$ (2 mL) and stirred at 0° C. for 40 min. The mixture was poured into ice water (10 mL) and the yellow solid was filtered. The solid was washed with NaHCO$_3$ (10 mL), water (20 mL) and concentrated to get ethyl 1,3-dimethyl-4-nitro-pyrrole-2-carboxylate (2-3) as a yellow solid. LCMS: RT 0.83 min, m/z=213.1 [M+H]$^+$.

1,3-dimethyl-4-nitro-1H-pyrrole-2-carboxylic acid: To a solution of ethyl 1,3-dimethyl-4-nitro-pyrrole-2-carboxylate (2.2 g, 10.37 mmol) in H$_2$O (5 mL) and EtOH (20 mL) was added NaOH (1.24 g, 31.11 mmol). The mixture was stirred at 50° C. for 1 h. The reaction mixture was concentrated under reduced pressure, diluted with water 20 mL, adjusted to pH=4 with HCl (6 N) and extracted with EA (3×20 mL). The combined organic layers were washed with saturated brine (20 mL), dried over Na$_2$SO$_4$, filtered and concentrated under reduced pressure to give 1,3-dimethyl-4-nitro-pyrrole-2-carboxylic acid as a yellow solid. LCMS: RT 0.19 min, m/z=183.1 [M−H].

1,3-dimethyl-4-nitro-1H-pyrrole-2-carboxamide: To a solution of 1,3-dimethyl-4-nitro-pyrrole-2-carboxylic acid (1.8 g, 9.77 mmol) in DCM (20 mL) was added oxalyl chloride (2.48 g, 19.54 mmol). The mixture was stirred at 25° C. for 1 h. The mixture was concentrated to get a residue. The residue was dissolve with THF (20 mL) and then added dropwise to NH$_3$.H$_2$O (30 mL). The mixture was stirred at 25° C. for 1 h. The reaction mixture was concentrated under reduced pressure to give 1,3-dimethyl-4-nitro-pyrrole-2-carboxamide as a yellow gum. LCMS: RT 0.359 min, m/z=184.1 [M+H]$^+$. $^1$H NMR (400 MHz, DMSO): δ2.36 (s, 3H), 3.72 (s, 3H), 7.66 (s, 2H), 8.03 (s, 1H).

1,3-dimethyl-4-nitro-1H-pyrrole-2-carbonitrile: A solution of 1,3-dimethyl-4-nitro-pyrrole-2-carboxamide (1.58 g, 8.63 mmol) in POCl$_3$ (10 mL) was stirred at 110° C. for 1 h under N$_2$. The reaction mixture was concentrated under reduced pressure. The residue was diluted with water (20 mL) and extracted with EtOAc (3×20 mL). The combined organic layers were washed with aq. NaHCO$_3$ (50 mL) and saturated brine (50 mL), dried over Na$_2$SO$_4$, filtered and concentrated under reduced pressure to give 1,3-dimethyl-4-nitro-pyrrole-2-carbonitrile (2-6) as a yellow oil. LCMS: RT 0.667 min, m/z=166 [M+H]$^+$.

4-amino-1,3-dimethyl-1H-pyrrole-2-carbonitrile: To a solution of 1,3-dimethyl-4-nitro-pyrrole-2-carbonitrile (500 mg, 3.03 mmol) in EtOH (6 mL) and H$_2$O (1.5 mL) was added Fe (845 mg, 15.14 mmol) and NH$_4$Cl (809 mg, 15.14 mmol). The mixture was stirred at 80° C. for 1 h. The reaction mixture was filtered and the filtrate was concentrated to get a residue. The residue was added with EtOAc (50 mL), filtered and the filtrate was concentrated to give 4-amino-1,3-dimethyl-pyrrole-2-carbonitrile as a black brown solid. LCMS: RT 0.572 min, m/z=136.1 [M+H]$^+$.

1,3-dimethyl-4-((4-(methylamino)-5-(trifluoromethyl) pyrimidin-2-yl)amino)-1H-pyrrole-2-carbonitrile (14): 4-amino-1,3-dimethyl-pyrrole-2-carbonitrile (150 mg, 1.11 mmol), 2-chloro-N-methyl-5-(trifluoromethyl)pyrimidin-4-amine (235 mg, 1.11 mmol) and TEA (337 mg, 3.33 mmol) were taken up into a microwave tube in n-BuOH (4 mL). The sealed tube was heated at 120° C. for 2 h under microwave. The reaction mixture was concentrated under reduced pressure. The residue was diluted with H$_2$O (30 mL) and extracted with EtOAc (3×10 mL). The combined organic layers were washed with brine (10 mL), dried over Na$_2$SO$_4$, filtered and concentrated under reduced pressure to give a residue, which was purified by prep-HPLC (neutral condition), to give 1,3-dimethyl-4-[[4-(methylamino)-5-(trifluoromethyl)pyrimidin-2-yl]amino]pyrrole-2-carbonitrile (14). $^1$H NMR (400 MHz, MeOD): δ 7.99 (s, 1H), 7.23 (s, 1H), 3.73 (s, 3H), 2.96 (s, 3H), 2.13 (s, 3H); HPLC: RT 1.79 min; MS: m/z: 311.1 [M+H]$^+$.

Example 3

Synthesis of 4-((4-(ethylamino)-5-(trifluoromethyl) pyrimidin-2-yl)amino)-3-methyl-1-((1-methyl-1H-pyrazol-3-yl)methyl)-1H-pyrrole-2-carbonitrile (15)

Ethyl 3-methyl-4-nitro-1H-pyrrole-2-carboxylate: Ethyl 3-methyl-1H-pyrrole-2-carboxylate (5 g, 32.64 mmol) was added to HNO$_3$ (29.4 mL) at 0° C. over a period of 1 h under N$_2$. During which the temperature was maintained below 15° C. The reaction mixture was stirred at 15° C. for 40 min. The brown reaction mixture was poured into ice-water. The yellow precipitate was collected, washed exhaustively with water, concentrated to get ethyl 3-methyl-4-nitro-1H-pyrrole-2-carboxylate as a yellow solid. LCMS: RT 0.759 min, m/z=199.1 [M+H]$^+$. $^1$H NMR (400 MHz, CDCl$_3$): δ ppm 9.35 (br. s., 1H), 7.76 (d, J=3.89 Hz, 1H), 4.37-4.43 (m, 2H), 2.68 (s, 3H), 1.41 (t, J=7.15 Hz, 3H).

3-methyl-4-nitro-1H-pyrrole-2-carboxylic acid: To a solution of ethyl 3-methyl-4-nitro-1H-pyrrole-2-carboxylate (1.8 g, 9.08 mmol) in EtOH (10 mL) and H$_2$O (3 mL) was added NaOH (1.09 g, 27.24 mmol). The mixture was stirred at 50° C. for 16 h. The reaction mixture was concentrated under reduced pressure. The residue was diluted with H$_2$O (45 mL), acidified to pH=4 with HCl (4N) and extracted with EtOAc (3×15 mL). The combined organic layers were washed with brine (15 mL), dried over Na$_2$SO$_4$, filtered and concentrated under reduced pressure to give 3-methyl-4-nitro-1H-pyrrole-2-carboxylic acid as a yellow solid. LCMS: RT 1.122 min, m/z=169.1 [M−H]$^−$.

3-methyl-4-nitro-1H-pyrrole-2-carboxamide: To a solution of 3-methyl-4-nitro-1H-pyrrole-2-carboxylic acid (500 mg, 2.94 mmol) in DCM (2 mL) was added oxalyl chloride (746 mg, 5.88 mmol) and DMF (0.1 mL) at 0° C. The mixture was stirred at 25° C. for 1 h. The mixture was concentrated and dissolved to THF (3 mL). The mixture was added to NH$_3$.H$_2$O (5 mL) at 0° C. and stirred at 25° C. for 1 h. The mixture was concentrated under reduced pressure. The residue was diluted with water (8 mL) and extracted with EtOAc (3×7 mL). The combined organic layers were washed with brine (10 mL), dried over Na$_2$SO$_4$, filtered and concentrated under reduced pressure to give 3-methyl-4-nitro-1H-pyrrole-2-carboxamide as a yellow oil. LCMS: RT 1.363 min, m/z=170.1 [M+H]$^+$.

3-methyl-4-nitro-1H-pyrrole-2-carbonitrile: A solution of 3-methyl-4-nitro-1H-pyrrole-2-carboxamide (600 mg, 3.55 mmol) in POCl$_3$ (3 mL) was degassed and purged with N$_2$ for 3 times, and then the mixture was stirred at 110° C. for 1 h under N$_2$. The reaction mixture was quenched by addition of H$_2$O (30 mL) at 0° C., adjusted to pH=8 with aq. NaHCO$_3$ and extracted with EtOAc (3×10 mL). The combined organic layers were washed with brine (10 mL), dried over Na$_2$SO$_4$, filtered and concentrated under reduced pressure to give a residue. The residue was purified by prep-TLC (SiO$_2$, PE: EtOAc=2:1) to give 3-methyl-4-nitro-1H-pyrrole-2-carbonitrile (3-5) as a yellow solid. $^1$H NMR (400 MHz, MeOD): δ ppm 2.45 (s, 3H), 7.90 (s, 1H).

(1-methyl-1H-pyrazol-3-yl)methyl methanesulfonate: To a solution of (1-methylpyrazol-3-yl)methanol (3-6, 100 mg, 891.82 μmol) in DCM (2 mL) was added MsCl (153 mg, 1.34 mmol, 103.54 L) and TEA (180 mg, 1.78 mmol). The mixture was stirred at 0° C. for 20 min. The mixture was poured into ice-water (10 mL) and extracted with DCM (3×4 mL). The combined organic phase was washed with brine (5 mL), dried with anhydrous Na$_2$SO$_4$, filtered and concentrated under reduced pressure to give (1-methyl-1H-pyrazol-3-yl)methyl methanesulfonate as a yellow oil.

3-methyl-1-((1-methyl-1H-pyrazol-3-yl)methyl)-4-nitro-1H-pyrrole-2-carbonitrile: To a solution of 3-methyl-4-nitro-1H-pyrrole-2-carbonitrile (3-5, 70 mg, 463.21 μmol) in DMF (5 mL) was added NaH (22 mg, 555.85 mol, 60% purity) at 0° C. The mixture was stirred at 15° C. for 1 h. (1-methylpyrazol-3-yl)methyl methanesulfonate (176 mg, 926.42 mol) was added to the mixture and stirred at 60° C. for 16 h. The reaction mixture was quenched by addition of ice-water (30 mL) at 0° C., and extracted with EtOAc (3×10 mL). The combined organic layers were washed with brine (10 mL), dried over Na$_2$SO$_4$, filtered and concentrated under reduced pressure to give a residue. The residue was purified by prep-TLC (SiO$_2$, PE:EtOAc=1:1) to give 3-methyl-1-[(1-methylpyrazol-3-yl)methyl]-4-nitro-pyrrole-2-carbonitrile (3-8) as a yellow solid. LCMS: RT 0.756 min, m/z=246.2 [M+H]$^+$.

4-amino-3-methyl-1-((1-methyl-1H-pyrazol-3-yl) methyl)-1H-pyrrole-2-carbonitrile: To a solution of 3-methyl-1-[(1-methylpyrazol-3-yl)methyl]-4-nitro-pyrrole-2-carbonitrile (120 mg, 489.32 µmol) in EtOH (4 mL) and H$_2$O (1 mL) was added Fe (137 mg, 2.45 mmol) and NH$_4$Cl (131 mg, 2.45 mmol). The mixture was stirred at 80° C. for 2 h. The reaction mixture was filtered and the filtrate was concentrated under reduced pressure to give a residue. The residue was diluted with H$_2$O (20 mL) and extracted with EtOAc (3×10 mL). The combined organic layers were washed with brine (10 mL), dried over Na$_2$SO$_4$, filtered and concentrated under reduced pressure to give 4-amino-3-methyl-1-((1-methyl-1H-pyrazol-3-yl)methyl)-1H-pyrrole-2-carbonitrile as a yellow gum. LCMS: RT 0.104 min, m/z=216.1 [M+H]$^+$ 4-((4-(ethylamino)-5-(trifluoromethyl)pyrimidin-2-yl)amino)-3-methyl-1-((1-methyl-1H-pyrazol-3-yl)methyl)-1H-pyrrole-2-carbonitrile (15): A mixture of 4-amino-3-methyl-1-[(1-methylpyrazol-3-yl)methyl]pyrrole-2-carbonitrile (120 mg, 557.49 µmol), 2-chloro-N-ethyl-5-(trifluoromethyl)pyrimidin-4-amine (126 mg, 557.49 mol) and PTSA (48 mg, 278.75 µmol) in dioxane (3 mL) was degassed and purged with N$_2$ for 3 times, and then the mixture was stirred at 90° C. for 2 h under N$_2$. The reaction mixture was concentrated under reduced pressure, diluted with H$_2$O (30 mL) and extracted with EtOAc (3×10 mL). The combined organic layers were washed with brine (10 mL), dried over Na$_2$SO$_4$, filtered and concentrated under reduced pressure to give a residue. The residue was purified by prep-HPLC (neutral condition) to give 4-[[4-(ethylamino)-5-(trifluoromethyl)pyrimidin-2-yl]amino]-3-methyl-1-[(1-methylpyrazol-3-yl)methyl]pyrrole-2-carbonitrile (15). $^1$H NMR (400 MHz, CDCl$_3$): δ ppm 8.06 (br. s., 1H), 7.37 (br. s., 1H), 7.31 (br. s., 1H), 6.21 (br. s., 1H), 5.12 (s, 2H), 3.88 (s, 3H), 3.43-3.53 (m, 2H), 2.19 (s, 3H), 1.22-1.29 (m, 3H); HPLC: RT: 2.04 min; MS: m/z: 405.2 [M+H]$^+$.

Example 4

Synthesis of 4-((4-(ethylamino)-5-(trifluoromethyl)pyrimidin-2-yl)amino)-3-methyl-1-((1-methyl-1H-pyrazol-3-yl)methyl)-1H-pyrrole-2-carbonitrile (16)

3-methyl-1-(methylsulfonyl)-4-nitro-1H-pyrrole-2-carbonitrile(4-2): To a mixture of 3-methyl-4-nitro-1H-pyrrole-2-carbonitrile (30 mg, 198.52 mol) in THF (3 mL) was added NaH (12 mg, 297.78 µmol, 60% purity) in one portion at 0° C. under N$_2$. The mixture was stirred at 15° C. for 1 h. MsCl (34 mg, 297.78 µmol) was added to the mixture at 0° C. and stirred at 15° C. for 16 h. The residue was poured into ice-water (20 mL) and then extracted with EtOAc (3×10 mL). The combined organic phase was washed with brine (10 mL), dried with anhydrous Na$_2$SO$_4$, filtered and concentrated under reduced pressure. The residue was purified by prep-TLC (SiO$_2$, PE:EtOAc=3:1) to give 3-methyl-1-methylsulfonyl-4-nitro-pyrrole-2-carbonitrile as a yellow gum. LCMS: RT 0.729 min, m/z=230.0 [M+H]$^+$.

4-amino-3-methyl-1-(methylsulfonyl)-1H-pyrrole-2-carbonitrile: To a solution of 3-methyl-1-methylsulfonyl-4-nitro-pyrrole-2-carbonitrile (40 mg, 174.5 µmol) in EtOH (2 mL) and H$_2$O (0.5 mL) was added Fe (61 mg, 1.09 mmol) and NH$_4$Cl (58 mg, 1.09 mmol). The mixture was stirred at 80° C. for 1 h. The mixture was filtered and the filtrate was concentrated. The residue was added with H$_2$O (20 mL) and extracted with EtOAc (3×10 mL). The combined organic phase was washed with brine (10 mL), dried with anhydrous Na$_2$SO$_4$, filtered and concentrated under reduced pressure to give 4-amino-3-methyl-1-methylsulfonyl-pyrrole-2-carbonitrile as a yellow gum. LCMS: RT 0.13 min, m/z=200.1 [M+H]$^+$.

4-((4-(ethylamino)-5-(trifluoromethyl)pyrimidin-2-yl)amino)-3-methyl-1-(methylsulfonyl)-1H-pyrrole-2-carbonitrile (16): A mixture of 4-amino-3-methyl-1-methylsulfonyl-pyrrole-2-carbonitrile (50 mg, 251 mol), 2-chloro-N-ethyl-5-(trifluoromethyl)pyrimidin-4-amine (59 mg, 262.01 µmol) and TsOH.H$_2$O (55 mg, 291.12 mol) in 1,4-dioxane (3 mL) was degassed and purged with N$_2$ for 3 times, and then the mixture was stirred at 90° C. for 2 h under N$_2$. The reaction mixture was concentrated under reduced pressure, diluted with H$_2$O (30 mL) and extracted with EtOAc (3×10 mL). The combined organic layers were washed with brine (10 mL), dried over Na$_2$SO$_4$, filtered and concentrated under reduced pressure to give a residue. The residue was purified by prep-HPLC (neutral condition) to give 4-[[4-(ethylamino)-5-(trifluoromethyl)pyrimidin-2-yl]amino]-3-methyl-1-methylsulfonyl-pyrrole-2-carbonitrile (16). $^1$H NMR (400 MHz, CDCl$_3$): δ 8.18 (s, 1H), 8.03 (s, 1H), 6.66 (br. s., 1H), 5.25 (br. s., 1H), 3.52-3.61 (m, 2H), 3.30 (s, 3H), 2.29 (s, 3H), 1.33 (t, J=7.22 Hz, 3H); HPLC: RT 3.73 min; MS: m/z: 389.0 [M+H]$^+$.

Example 5

Synthesis of N$^2$-(4-chloro-3-cyclopropylisothiazol-5-yl)-N$^4$-methyl-5-(trifluoromethyl)pyrimidine-2,4-diamine (18) and N$^2$-(3-cyclopropyl-4-methylisothiazol-5-yl)-N$^4$-methyl-5-(trifluoromethyl)pyrimidine-2,4-diamine (21)

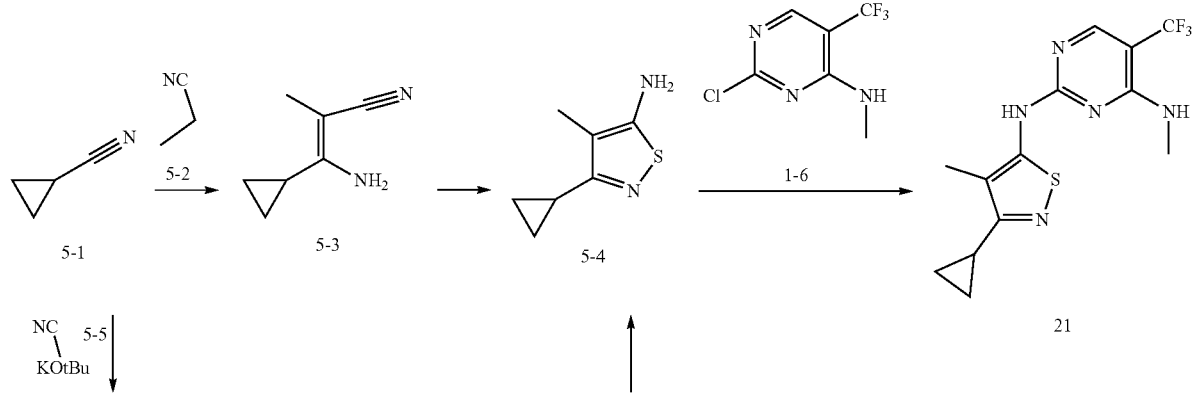

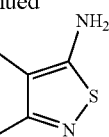
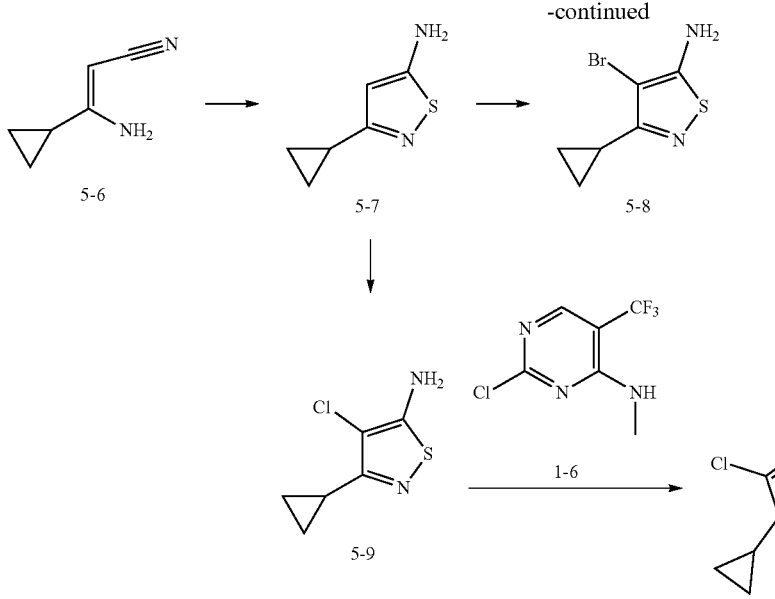

Compound 21 is synthesized by two different routes as shown in the scheme above. Reaction of cyanocyclopropane 5-1 with cyanoethane 5-2 in presence of a base such as potassium tert-butoxide in a solvent such as toluene provides compound 5-3, which on cyclization, by treating with $H_2S$ in a solvent such as methanol followed by $I_2$ in presence of a base such as potassium carbonate in a solvent such as diethyl ether, provides the aminoisothiazole 5-4. Coupling of compound 5-4 with pyrimidine 1-6 in presence of an acid such as toluene sulfonic acid using a solvent such as 1,4-dioxane, provides compound 21.

Alternatively, cyanocyclopropane 5-1 is reacted with cyanomethane 5-5 in presence of a base such as potassium tert-butoxide in a solvent such as toluene to provide compound 5-6, which on cyclization, by treating with $H_2S$ in a solvent such as methanol followed by $I_2$ in presence of a base such as potassium carbonate in a solvent such as diethyl ether, provides the aminosothiazole 5-7. Bromination of compound 5-7 using N-chlorosuccinimide in a solvent such as carbon tetrachloride provides the bromoisothiazole 5-8 which is treated with $MeB(OH)_3$ to provide compound 5-4. Compound 5-4 is converted to compound 21 as discussed above.

Alternatively, compound 5-7 is chlorinated using N-chlorosuccinimide in a solvent such as dichloromethane to provide the chloroisothiazole 5-9. Coupling of compound 5-9 with pyrimidine 1-6 in presence of an acid such as toluene sulfonic acid using a solvent such as 1,4-dioxane, provides compound 18.

Example 6

Synthesis of $N^2$-(4-chloro-2-methyl-1H-imidazol-5-yl)-$N^4$-methyl-5-(trifluoromethyl)pyrimidine-2,4-diamine (Compound 19) and $N^2$-(1,2-dimethyl-1H-imidazol-5-yl)-$N^4$-methyl-5-(trifluoromethyl)pyrimidine-2,4-diamine (Compound 20)

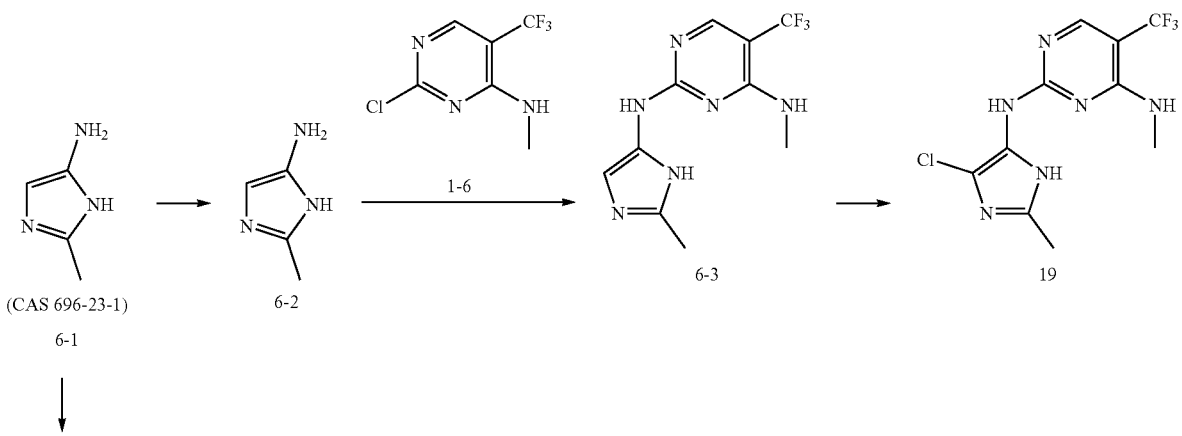

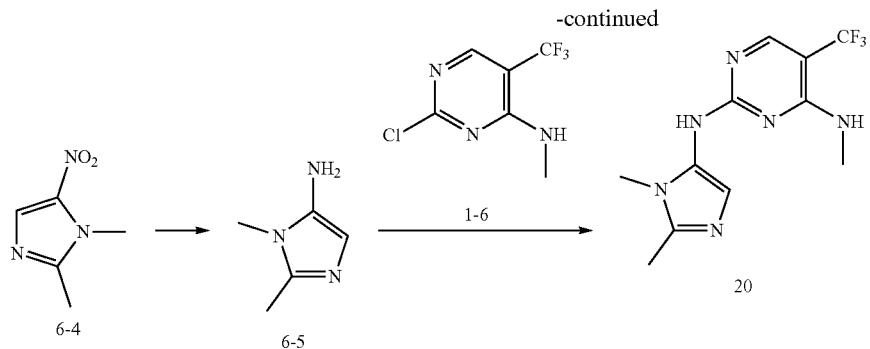

Compounds 19 and 20 are synthesized as shown in the scheme above. Reduction of 2-methyl-5-nitro-1H-imidazole 6-1 under hydrogen and Pd/C in a solvent such as methanol provides amine 6-2, coupling of which with pyrimidine 1-6 in presence of an acid such as toluene sulfonic acid using a solvent such as 1,4-dioxane, provides compound 6-3. Chlorination of compound 6-3 using N-chlorosuccinimide in a solvent such as dichloromethane provides compound 19.

Alternatively, compound 6-1 is methylated using methyl iodide in presence of a base such as $CsCO_3$ in a solvent such as DMF to provide 1,2-dimethyl-5-nitro-1H-imidazole 6-4, which on reduction under hydrogen and Pd/C in a solvent such as methanol provides amine 6-5, coupling of which with pyrimidine 1-6 in presence of an acid such as toluene sulfonic acid using a solvent such as 1,4-dioxane, provides compound 20.

Example 7

Synthesis (3S)-3-[4-cyclopropyl-5-[[4-(ethylamino)-5-(trifluoromethyl)pyrimidin-2-yl]amino]thiazol-2-yl]-3-(trideuteriomethyl)pyrrolidin-2-one and (3R)-3-[4-cyclopropyl-5-[[4-(ethylamino)-5-(trifluoromethyl)pyrimidin-2-yl]amino]thiazol-2-yl]-3-(trideuteriomethyl)pyrrolidin-2-one (51 and 52)

1-[(4-methoxyphenyl)methyl]pyrrolidin-2-one: To a solution of pyrrolidin-2-one (50 g, 587.54 mmol) in DMF (750 mL) was added NaH (25.85 g, 646.29 mmol, 60% purity) slowly at 0° C. over a period of 30 min under $N_2$. A solution of PMB-Cl (92.02 g, 587.54 mmol, 80.02 mL) was then added dropwise at 0° C. over a period of 30 min under $N_2$. The reaction mixture was warmed to 25° C. and stirred at 25° C. for 15 h. The reaction was quenched by cold aq. $NH_4Cl$ (200 mL) slowly and water (2 L), then extracted with EtOAc (3×500 mL). The combined organic phase was washed with brine (3×200 mL), dried over anhydrous $Na_2SO_4$, filtered and concentrated under reduced pressure. The residue was purified by silica gel column chromatography (PE:EtOAc=5:1 to 0:1) to afford 1-[(4-methoxyphenyl)methyl]pyrrolidin-2-one as a yellow oil. $^1$H NMR (400 MHz, $CDCl_3$) δ 7.15 (d, J=8.53 Hz, 2H), 6.87 (d, J=8.53 Hz, 2H), 4.38 (s, 2H), 3.77 (s, 3H), 3.19-3.25 (m, 2H), 2.40-2.44 (m, 2H), 1.92-2.00 (m, 2H).

2,4-dichlorothiazole-5-carboxylic acid: To a solution of LDA (2 M, 178.55 mL) in THF (50 mL) was added a solution of 2,4-dichlorothiazole (50 g, 324.63 mmol) dropwise in THF (200 mL) at −78° C. over 30 min. After addition, the mixture was stirred at this temperature for 30 min, and then carbon dioxide (14.29 g, 324.63 mmol) was added at −78° C. The resulting mixture was warmed to 25° C. and stirred for 1 h. The crude mixture crude poured into 1N HCl (1 L) and extracted with EtOAc (3×500 mL). The combined organic phase was washed with brine (500 mL), dried over anhydrous $Na_2SO_4$, filtered and concentrated. The residue was washed with PE (300 mL), filtered and the filtrate was concentrated under reduced pressure to afford 2,4-dichlorothiazole-5-carboxylic acid as a yellow solid. $^1$H NMR (400 MHz, $CDCl_3$): δ 9.69 (s, 1H).

tert-butyl 2,4-dichlorothiazole-5-carboxylate: A suspension of 2,4-dichlorothiazole-5-carboxylic acid (112 g, 565.57 mmol) in $SOCl_2$ (656 g, 5.51 mol, 400 mL) under $N_2$ was stirred at 85° C. for 2 h. The mixture was concentrated under reduced pressure. The residue in THF (500 mL) and DCM (500 mL) was added with t-BuOK (76.16 g, 678.68 mmol) slowly at 0° C. under $N_2$. The mixture was stirred at 0° C. for 3 h. The mixture was poured into ice-water (1000 mL) and extracted with EtOAc (3×600 mL). The combined organic phase was washed with brine (600 mL), dried over anhydrous $Na_2SO_4$, filtered and concentrated. The residue was adjusted pH=7 by 6 N NaOH, extracted with EtOAc (3×600 mL), washed with brine (600 mL), dried with anhydrous $Na_2SO_4$, filtered and concentrated. The residue was purified by column chromatography (PE:EtOAc=1:0 to 10:1) to give tert-butyl 2,4-dichlorothiazole-5-carboxylate as a yellow oil. $^1$H NMR (400 MHz, $CDCl_3$): δ 1.56 (s, 9H).

tert-butyl 4-chloro-2-[1-[(4-methoxyphenyl)methyl]-2-oxo-pyrrolidin-3-yl]thiazole-5-carboxylate: To a solution of 1-[(4-methoxyphenyl)methyl]pyrrolidin-2-one (38.77 g, 188.88 mmol) in THF (800 mL) was added a solution of LDA (2 M, 98.38 mL) dropwise at −78° C. over a period of 30 min under $N_2$. The reaction mixture was stirred at −78° C. for 30 min and a solution of tert-butyl 2,4-dichlorothiazole-5-carboxylate (40 g, 157.40 mmol) in THF (100 mL) was added drop-wise at −78° C. The reaction mixture was stirred at −50° C. for another 3 h. The reaction was quenched by aqueous $NH_4Cl$ (200 mL) slowly and then extracted with EtOAc (2×100 mL). The combined organic phase was washed with brine (100 mL), dried over anhydrous $Na_2SO_4$, filtered and concentrated under reduced pressure to give a residue. The residue was purified by silica gel column chromatography (PE:EtOAc, gradient from 3:1 to 1:1) to give tert-butyl 4-chloro-2-[1-[(4-methoxyphenyl)methyl]-2-oxo-pyrrolidin-3-yl]thiazole-5-carboxylate as a yellow solid. $^1$H NMR (400 MHz, $CDCl_3$): δ 7.19 (d, J=8.53 Hz, 2H), 6.87 (d, J=8.53 Hz, 2H), 4.38-4.54 (m, 2H), 3.97 (t, J=9.10 Hz, 1H), 3.81 (s, 3H), 3.28-3.43 (m, 2H), 2.50-2.65 (m, 2H), 1.56-1.60 (m, 11H).

tert-butyl 4-chloro-2-[1-[(4-methoxyphenyl)methyl]-2-oxo-3-(trideuteriomethyl)pyrrolidin-3-yl]thiazole-5-carboxylate: To a solution of tert-butyl 4-chloro-2-[1-[(4- methoxyphenyl)methyl]-2-oxo-pyrrolidin-3-yl]thiazole-5-carboxylate (8.5 g, 20.10 mmol) in THF (100 mL) was added a solution of LDA (2 M, 12.06 mL) dropwise at −78° C. over a period of 30 min under $N_2$. The reaction mixture was stirred at −78° C. for 30 mins, then trideuterio(iodo) methane (4.37 g, 30.15 mmol, 1.88 mL) was added. The reaction mixture was warmed to 20° C. over a period of 1 h and stirred at 20° C. for another 10 h. The reaction mixture was quenched by addition of aqueous $NH_4Cl$ (100 mL) at 0° C., and then diluted with $H_2O$ (50 mL) and extracted with EtOAc (3×50 mL). The combined organic layers were washed with brine (50 mL), dried over $Na_2SO_4$, filtered and concentrated under reduced pressure to give a residue. The residue was purified by silica gel column chromatography (PE:EtOAc=5:1) to give tert-butyl 4-chloro-2-[1-[(4-methoxyphenyl)methyl]-2-oxo-3-(trideuteriomethyl)pyrrolidin-3-yl]thiazole-5-carboxylate as a off-white solid. $^1H$ NMR (400 MHz, $CDCl_3$) δ 7.16 (d, J=8.53 Hz, 2H), 6.86 (d, J=8.53 Hz, 2H), 4.33-4.53 (m, 2H), 3.80 (s, 3H), 3.31-3.41 (m, 1H), 3.21-3.31 (m, 1H), 2.73-2.84 (m, 1H), 2.17 (ddd, J=4.96, 7.97, 13.05 Hz, 1H), 1.57 (s, 9H).

tert-butyl 4-cyclopropyl-2-[1-[(4-methoxyphenyl)methyl]-2-oxo-3-(trideuteriomethyl)pyrrolidin-3-yl]thiazole-5-carboxylate: To a mixture of tert-butyl 4-chloro-2-[1-[(4-methoxyphenyl)methyl]-2-oxo-3-(trideuteriomethyl)pyrrolidin-3-yl]thiazole-5-carboxylate (3.77 g, 8.57 mmol), cyclopropylboronic acid (5.89 g, 68.56 mmol) and CsF (6.51 g, 42.85 mmol) in 1,4-dioxane (113 mL) was added $Pd(dppf)Cl_2.CH_2Cl_2$ (700 mg, 857 umol) at 25° C. under $N_2$. The mixture was then heated to 140° C. and stirred for 16 h. The mixture was cooled to 25° C. and poured into water (300 mL). The aqueous phase was extracted with EtOAc (3×100 mL). The combined organic phase was washed with brine (50 mL), dried over anhydrous $Na_2SO_4$, filtered and concentrated under reduced pressure to give a residue. The residue was purified by silica gel column chromatography (PE:EtOAc=5:1) to afford tert-butyl 4-cyclopropyl-2-[1-[(4-methoxyphenyl)methyl]-2-oxo-3-(trideuteriomethyl)pyrrolidin-3-yl]thiazole-5-carboxylate as a light-yellow oil. LCMS: RT 0.979 min, m/z=446.3 $[M+H]^+$.

$^1H$ NMR (400 MHz, $CDCl_3$): δ 7.13 (d, J=8.60 Hz, 2H), 6.86 (d, J=7.54 Hz, 2H), 4.31-4.52 (m, 2H), 3.81 (s, 3H), 3.37 (td, J=7.63, 9.21 Hz, 1H), 3.19 (dt, J=3.97, 9.04 Hz, 1H), 2.93-3.02 (m, 1H), 2.71 (ddd, J=3.97, 8.10, 12.62 Hz, 1H), 2.00-2.05 (m, 1H), 1.57 (s, 9H), 0.93-1.07 (m, 4H).

4-cyclopropyl-2-[2-oxo-3-(trideuteriomethyl)pyrrolidin-3-yl]thiazole-5-carboxylic acid: To a solution of tert-butyl 4-cyclopropyl-2-[1-[(4-methoxyphenyl)methyl]-2-oxo-3-(trideuteriomethyl)pyrrolidin-3-yl]thiazole-5-carboxylate (3.4 g, 7.63 mmol) in DCM (34 mL) was added TFA (34 mL) and TfOH (8.02 g, 53.41 mmol, 4.72 mL) at 25° C. under $N_2$. The mixture was then heated to 50° C. and stirred for 16 h. The mixture was cooled to 25° C. and concentrated under reduced pressure to give a residue. The residue was added with ice-water (50 mL) and stirred for 10 min. The mixture was filtered, and the filter cake was triturated with EtOAc (30 mL) and filtered to give 4-cyclopropyl-2-[2-oxo-3-(trideuteriomethyl)pyrrolidin-3-yl]thiazole-5-carboxylic acid as an off-white solid. The product was used into the next step without further purification. LCMS: RT 0.682 min, m/z=270.1$[M+H]^+$. $^1H$ NMR (400 MHz, DMSO-$d_6$): δ 13.22 (br s, 1H), 7.99 (s, 1H), 3.28 (t, J=6.73 Hz, 2H), 2.89-3.00 (m, 1H), 2.63 (td, J=6.59, 13.06 Hz, 1H), 2.13 (td, J=6.56, 12.90 Hz, 1H), 1.02 (br dd, J=2.32, 8.27 Hz, 2H), 0.89-1.00 (m, 2H).

tert-butyl N-[4-cyclopropyl-2-[2-oxo-3-(trideuteriomethyl)pyrrolidin-3-yl]thiazol-5-yl]carbamate: To a mixture of 4-cyclopropyl-2-[2-oxo-3-(trideuteriomethyl)pyrrolidin-3-yl]thiazole-5-carboxylic acid (1.5 g, 5.57 mmol), TEA (1.97 g, 19.50 mmol, 2.70 mL) and t-BuOH (20.64 g, 278.50 mmol, 26.46 mL) in toluene (15 mL) was added DPPA (4.6 g, 16.71 mmol, 3.62 mL) at 25° C. under $N_2$. The mixture was then heated to 90° C. and stirred for 16 h. The mixture was cooled to 25° C. and concentrated under reduced pressure. The residue was poured into water (100 mL). The aqueous phase was extracted with EtOAc (3×50 mL). The combined organic phase was washed with brine (30 mL), dried over anhydrous $Na_2SO_4$, filtered and concentrated under reduced pressure to give a residue. The residue was purified by silica gel column chromatography (PE:EtOAc=1:1) to afford tert-butyl N-[4-cyclopropyl-2-[2-oxo-3-(trideuteriomethyl)pyrrolidin-3-yl]thiazol-5-yl]carbamate as a light-yellow solid. LCMS: RT 0.767 min, m/z=341.2 $[M+H]^+$.

$^1H$ NMR (400 MHz, $CDCl_3$): δ 6.62 (br s, 1H), 5.97 (br s, 1H), 3.47-3.55 (m, 1H), 3.36 (dt, J=4.89, 8.66 Hz, 1H), 2.90 (ddd, J=4.45, 7.69, 12.33 Hz, 1H), 2.12-2.20 (m, 1H), 1.69-1.78 (m, 1H), 1.52 (s, 9H), 0.86-0.95 (m, 4H).

(3S)-3-[4-cyclopropyl-5-[[4-(ethylamino)-5-(trifluoromethyl)pyrimidin-2-yl]amino]thiazol-2-yl]-3-(trideuteriomethyl)pyrrolidin-2-one and (3R)-3-[4-cyclopropyl-5-[[4-(ethylamino)-5-(trifluoromethyl)pyrimidin-2-yl]amino]thiazol-2-yl]-3-(trideuteriomethyl)pyrrolidin-2-one: To a mixture of tert-butyl N-[4-cyclopropyl-2-[2-oxo-3-(trideuteriomethyl)pyrrolidin-3-yl]thiazol-5-yl]carbamate (250 mg, 734.32 umol) and 2-chloro-N-ethyl-5-(trifluoromethyl)pyrimidin-4-amine (166 mg, 734.32 umol) in 1,4-dioxane (5 mL) was added p-TsOH.$H_2O$ (210 mg, 1.10 mmol) at 25° C. under $N_2$. The mixture was then heated to 90° C. and stirred for 4 h. The mixture was cooled to 25° C. and added with aqueous $NaHCO_3$ (60 mL). The aqueous phase was extracted with EtOAc (3×20 mL). The combined organic phase was washed with brine (20 mL), dried over anhydrous $Na_2SO_4$, filtered and concentrated under reduced pressure to give a residue. The residue was triturated with MTBE (20 mL) and filtered to afford product as a light-yellow solid, 100 mg was further separated by SFC to give (3S)-3-[4-cyclopropyl-5-[[4-(ethylamino)-5-(trifluoromethyl)pyrimidin-2-yl]amino]thiazol-2-yl]-3-(trideuteriomethyl)pyrrolidin-2-one as a light-yellow solid (peak 1 in SFC) and (3R)-3-[4-cyclopropyl-5-[[4-(ethylamino)-5-(trifluoromethyl)pyrimidin-2-yl]amino]thiazol-2-yl]-3-(trideuteriomethyl)pyrrolidin-2-one as a light-yellow solid (peak 2 in SFC).

(3S)-3-[4-cyclopropyl-5-[[4-(ethylamino)-5-(trifluoromethyl)pyrimidin-2-yl]amino]thiazol-2-yl]-3-(trideuteriomethyl)pyrrolidin-2-one. $^1H$ NMR (400 MHz, $CDCl_3$): δ 8.15 (s, 1H), 7.74 (br s, 1H), 5.93 (br s, 1H), 5.24 (br s, 1H), 3.65 (m, 2H), 3.48-3.57 (m, 1H), 3.39 (dt, J=4.39, 8.53 Hz, 1H), 3.01 (ddd, J=4.33, 7.84, 12.55 Hz, 1H), 2.13-2.24 (m, 1H), 1.77-1.87 (m, 1H), 1.30 (t, J=7.15 Hz, 3H), 0.86-0.98 (m, 4H). HPLC: RT: 2.32 min. MS: m/z: 430.2 $[M+H]^+$.

(3R)-3-[4-cyclopropyl-5-[[4-(ethylamino)-5-(trifluoromethyl)pyrimidin-2-yl]amino]thiazol-2-yl]-3-(trideuteriomethyl)pyrrolidin-2-one. $^1H$ NMR (400 MHz, $CDCl_3$): δ 8.15 (s, 1H), 7.60 (br s, 1H), 5.80 (br s, 1H), 5.24 (br s, 1H), 3.58-3.74 (m, 2H), 3.49-3.58 (m, 1H), 3.39 (dt, J=4.30, 8.65 Hz, 1H), 3.01 (ddd, J=4.30, 7.72, 12.46 Hz, 1H), 2.14-2.24 (m, 1H), 1.77-1.86 (m, 1H), 1.31 (t, J=7.17 Hz, 3H), 0.87-0.96 (m, 4H). HPLC: Retention Time: 2.32 min. MS: m/z: 430.2 $[M+H]^+$.

The following compounds from Table 1 were prepared according to the Examples above and/or general procedures described herein.

| No. | MS [M + H]+ |
|---|---|
| 1 | 410.1 |
| 2 | 355.1 |
| 3 | 408.1 |
| 10 | 437.1 |
| 22 | 375.1 |
| 23 | 407.2 |
| 24 | 417.1 |
| 25 | 395.1 |
| 26 | 389.1 |
| 27 | 329.1 |
| 28 | 361.1 |
| 29 | 401.2 |
| 30 | 386.1 |
| 31 | 425.1 |
| 32 | 369 |
| 33 | 443.2 |
| 34 | 421.2 |
| 36 | 377.1 |
| 37 | 409.1 |
| 38 | 421.0 |
| 39 | 430 [M + Na]+ |
| 40 | 445.1 |
| 41 | 431.0 |
| 42 | 410.2 |
| 43 | 410.2 |
| 44 | 427.2 |
| 45 | 427.2 |
| 46 | 441.3 |
| 47 | 441.3 |
| 48 | 421.0 |
| 49 | 421.0 |
| 50 | 391.1 |
| 51 | 430.2 |
| 52 | 430.2 |
| 53 | 427.1 |
| 54 | 427.2, 429.1 |
| 55 | 425.1 |
| 56 | 425.1 |
| 57 | 411 |
| 59 | 416.3 |
| 60 | 416.2 |

The other compounds in Table 1 and Table 1A are prepared according to the Examples above and/or general procedures described herein.

Example 7

Biochemical Assay of the Compounds

Materials:
LRRK2 G2019S enzyme
Substrate (LRRKtide)
ATP
TR-FRET dilution buffer
pLRRKtide antibody
384-well assay plate
DMSO
Enzyme reaction conditions
50 mM Tris pH 7.5, 10 mM $MgCl_2$, 1 mM EGTA, 0.01% Brij-35, 2 mM DTT
5 nM LRRK2
134 μM ATP
60 minute reaction time
23° C. reaction temperature
10 μL total reaction volume
Detection reaction conditions
1×TR-FRET dilution buffer
10 mM EDTA
2 nM antibody
23° C. reaction temperature
10 μL total reaction volume Compounds were prepared by initially diluting to 1 mM with DMSO. 35 μL of reference compound solution, 35 μL of test compound solution, and 35 μL HPE were successively added to the source plate (384-well assay plate, Labcyte). The plates were centrifuged at 2500 rpm for 1 minute and sealed in foil. POD was used to perform a 3.162 fold serial dilution and 100 nL of reference compound solution, test compound solution, HPE and ZPE were transferred to assay plates. The assay plate was centrifuged at 2500 rpm for 1 minute, and sealed with foil.

To perform the enzyme reaction, 5 μL of LRRKtide substrate and kinase mixture in assay buffer was added to all wells of the assay plate. The plate was centrifuged to concentrate the mixture at the bottom of the wells. The assay plate was incubated at 23° C. for 20 minutes. Following incubation, 5 μL of 2×ATP in assay buffer was added to each well, and plates were centrifuged to concentrate the mixture at the bottom of the wells. The plate was incubated at 23° C. for 60 minutes.

To perform the detection of the reaction, EDTA completely mixed in TR-FRET dilution buffer was added to antibody reagent. 10 μL of detection reagent was added to all wells of each well of the assay plate and the plate was centrifuged to concentrate the mixture at the bottom of the wells. The plate was then incubated at 23° C. for 60 minutes. Plates were read on Perkin Elmer Envision 2104 instrument in TR-FRET mode using a 340 nm excitation filter, 520 nm fluorescence emission filter, and 490 or 495 nm terbium emission filter.

Several of the compounds in Table 1 were tested according to the above methods and found to exhibit an LRRK2 G2019S $IC_{50}$ as indicated in Table 2. In the table below, activity is provided as follows: In the table below, activity is provided as follows: +++=$IC_{50}$ less than 30 nM; ++=$IC_{50}$ between 30 nM and 60 nM; +=$IC_{50}$ greater than 60 nM.

TABLE 2

Activity of Representative Compounds

| No. | $IC_{50}$ (nM) |
|---|---|
| 1 | +++ |
| 2 | +++ |
| 3 | +++ |
| 10 | +++ |
| 11 | +++ |
| 14 | +++ |
| 15 | +++ |
| 16 | +++ |
| 17 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 36 | +++ |
| 37 | +++ |
| 38 | +++ |
| 39 | +++ |
| 40 | +++ |
| 41 | +++ |
| 42 | +++ |
| 43 | +++ |
| 44 | +++ |

TABLE 2-continued

Activity of Representative Compounds

| No. | IC$_{50}$ (nM) |
|---|---|
| 45 | +++ |
| 46 | +++ |
| 47 | +++ |
| 48 | +++ |
| 49 | +++ |
| 50 | +++ |
| 51 | +++ |
| 52 | +++ |
| 53 | +++ |
| 54 | +++ |
| 59 | +++ |
| 60 | +++ |
| 61 | +++ |

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:

1. A compound of formula (I):

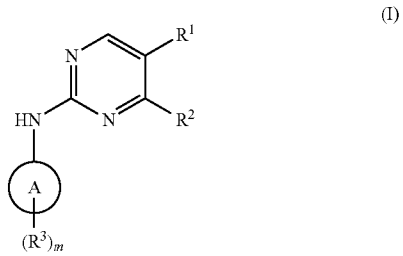

or a pharmaceutically acceptable salt, deuterated isotope, or stereoisomer thereof,
wherein:
  m is 1 or 2;
  ring A is isothiazolyl or thiazolyl;
  $R^1$ is halo, cyano, $C_{1-6}$ alkyl, or $C_{1-6}$ haloalkyl;
  $R^2$ is $N(R^5)(R^6)$, $C_{1-6}$ alkoxy, or cycloalkyl;
  each $R^3$ is independently H, halo, cyano, $C_{1-6}$ alkyl, $C_6$ haloalkyl, $C_{1-6}$ cyanoalkyl, $C_{1-6}$ aminoalkyl, amidoalkyl, $C_{1-6}$ hydroxyalkyl, $C_{1-6}$ alkoxyalkyl, $C(O)R^7$, amido, $N(R^{16})_2$, $C_{1-6}$ alkylsulfonyl, $C_{1-6}$ alkylsulfonylalkyl, cycloalkylalkyl, heterocyclylalkyl, alkytheterocyclylalkyl, arylalkyl, heteroarylalkyl, alkylheteroarylalkyl, cycloalkyl, cyanocycloalkyl, heteroarylcycloalkyl, alkylheteroarylcycloalkyl, heterocyclyl, aryl, or heteroaryl, wherein each $C_{1-6}$ alkyl, $C_{1-6}$ haloalkyl, $C_{1-6}$ cyanoalkyl, $C_{1-6}$ aminoalkyl, $C_{1-6}$ hydroxyalkyl, $C_{1-6}$ alkoxyalkyl, $C_{1-6}$ alkylsulfonyl, $C_{1-6}$ alkylsulfonylalkyl, cycloalkylalkyl, heterocyclylalkyl, alkylheterocyclylalkyl, arylalkyl, heteroarylalkyl, alkylheteroarylalkyl, cycloalkyl, cyanocycloalkyl, heteroarylcycloalkyl, alkylheteroarylcycloalkyl, heterocyclyl, aryl, and heteroaryl is optionally and independently substituted with one or more substituents independently selected from the group consisting of oxo, thioxo, halo, cyano, hydrazino, azido, nitro, alkyl, haloalkyl, hydroxyalkyl, cycloalkylalkyl, heterocyclylalkyl, aralkyl, heteroarylalkyl, alkenyl, alkynyl, imino, hydrazone, amidino, oxime, C(O)H, amido, imido, carboxy, C(O)Oalkyl, amino, guanidino, NHC(O)Oalkyl, hydroxy, alkoxy, haloalkoxy, OC(O)NH$_2$, thiol, thiocyanate, alkylthio, alkylsulfinyl, alkylsulfonyl, sulfonamido, sulfinic acid, sulfonic acid, cycloalkyl, heterocyclyl, aryl, heteroaryl, and Si(R$^Y$)$_3$;
  $R^5$ is H, $C_{1-6}$ alkyl, $C_{1-6}$ haloalkyl, or cycloalkyl;
  $R^6$ is H, $C_{1-6}$ alkyl, $C_{1-6}$ haloalkyl, or cycloalkyl;
  each $R^7$ is independently $C_{1-6}$ alkyl, $C_{1-6}$ haloalkyl, $C_{1-6}$ alkoxy, or heterocyclyl, wherein each $C_{1-6}$ alkyl, $C_{1-6}$ haloalkyl, $C_{1-6}$ alkoxy, and heterocyclyl is optionally and independently substituted with one or more substituents independently selected from the group consisting of halo, cyano, hydroxy, $C_{1-6}$ alkoxy, and $C_{1-6}$ alkylsulfonyl;
  each $R^{16}$ is independently H or $C_{1-6}$ alkyl, wherein each $C_{1-6}$ alkyl is optionally and independently substituted with one or more substituents independently selected from the group consisting of halo, cyano, hydroxy, $C_{1-6}$ alkoxy, and $C_{1-6}$ alkylsulfonyl; and each $R^Y$ is independently H, alkyl, alkenyl, alkynyl, heteroalkyl, cycloalkyl, heterocyclyl, aryl, or heteroaryl;

with the proviso that if $R^5$ or $R^6$ is cycloalkyl, then ring A is not isothiazolyl.

2. The compound of claim 1, wherein the compound is of formula (I'):

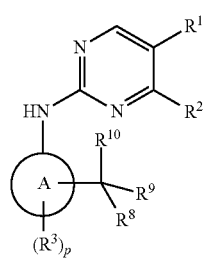

(I')

or a pharmaceutically acceptable salt, deuterated isotope, or stereoisomer thereof, wherein:
(i) $R^8$ is H or $C_{1-3}$ alkyl;
$R^9$ is H or $C_{1-2}$ alkyl;
$R^{10}$ is H, cyano, $C(O)NR^{12}R^{13}$, heteroaryl, or alkylheteroaryl; or
$R^8$ and $R^9$, together with the carbon to which they are attached, form a $C_{3-6}$ cycloalkyl; or
$R^9$ and $R^{10}$, together with the carbon to which they are attached, form a heterocyclyl, wherein the heterocyclyl is substituted with oxo and further optionally and independently substituted with one, two, three, or four substituents independently selected from the group consisting of halo and $C_{1-6}$ alkyl;
$R^{12}$ is H, $C_{1-6}$ alkyl, heteroalkyl, $C_{2-6}$ alkenyl, $C_{2-6}$ alkynyl, cycloalkyl, heterocyclyl, aryl, or heteroaryl; and
$R^{13}$ is H, $C_{1-6}$ alkyl, heteroalkyl, $C_{2-6}$ alkenyl, $C_{2-6}$ alkynyl, cycloalkyl, heterocyclyl, aryl, or heteroaryl; or
$R^{12}$ and $R^{13}$, together with the nitrogen to which they are attached, form a 3- to 6-membered heterocyclyl; or
(ii) $R^9$ and $R^{10}$, together with the carbon to which they are attached, form a C(O); and
$R^{10}$ is $C_{1-6}$ alkyl, $C_{1-6}$ haloalkyl, amino, $C_{1-6}$ alkylamino, or heterocyclyl, wherein the heterocyclyl is optionally and independently substituted with one or more independently selected halo substituents; and
p is 1.

3. The compound of claim 1, or a pharmaceutically acceptable salt, deuterated isotope, or stereoisomer thereof, wherein ring A is thiazolyl.

4. The compound of claim 3, wherein the compound is of formula (I'a):

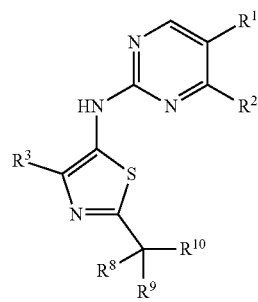

(I'a)

or a pharmaceutically acceptable salt, deuterated isotope, or stereoisomer thereof, wherein:
(i) $R^8$ is H or $C_{1-3}$ alkyl;
$R^9$ is H or $C_{1-2}$ alkyl;
$R^{10}$ is H, cyano, $C(O)NR^{12}R^{13}$, heteroaryl, or alkylheteroaryl; or
$R^8$ and $R^9$, together with the carbon to which they are attached, form a $C_{3-6}$ cycloalkyl; or
$R^9$ and $R^{10}$, together with the carbon to which they are attached, form a heterocyclyl, wherein the heterocyclyl is substituted with oxo and further optionally and independently substituted with one, two, three, or four substituents independently selected from the group consisting of halo and $C_{1-6}$ alkyl;
$R^{12}$ is H, $C_{1-6}$ alkyl, heteroalkyl, $C_{2-6}$ alkenyl, $C_{2-6}$ alkynyl, cycloalkyl, heterocyclyl, aryl, or heteroaryl; and
$R^{13}$ is H, $C_{1-6}$ alkyl, heteroalkyl, $C_{2-6}$ alkenyl, $C_{2-6}$ alkynyl, cycloalkyl, heterocyclyl, aryl, or heteroaryl; or
$R^{12}$ and $R^{13}$, together with the nitrogen to which they are attached, form a 3- to 6-membered heterocyclyl; or
(ii) $R^9$ and $R^{10}$, together with the carbon to which they are attached, form a C(O); and
$R^{10}$ is $C_{1-6}$ alkyl, $C_{1-6}$ haloalkyl, amino, $C_{1-6}$ alkylamino, or heterocyclyl, wherein the heterocyclyl is optionally and independently substituted with one or more independently selected halo substituents.

5. The compound of claim 4, wherein the compound is of formula (I'aa):

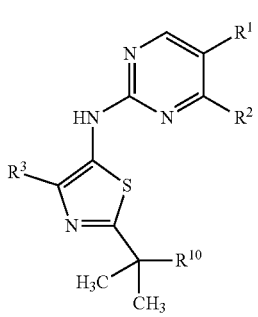

(I'aa)

or a pharmaceutically acceptable salt, deuterated isotope, or stereoisomer thereof, wherein:
$R^{10}$ is H, cyano, $C(O)NR^{12}R^{13}$, heteroaryl, or alkylheteroaryl.

6. The compound of claim 5, or a pharmaceutically acceptable salt, deuterated isotope, or stereoisomer thereof, wherein $R^{10}$ is cyano, $C(O)NR^{12}R^{13}$, heteroaryl, or alkylheteroaryl.

7. The compound of claim 5, or a pharmaceutically acceptable salt, deuterated isotope, or stereoisomer thereof, wherein $R^{10}$ is cyano, $C(O)NH_2$, 1H-1,2,4-triazol-1-yl, 1H-1,2,4-triazol-3-yl, or 2-methyl-2H-tetrazol-5-yl.

8. The compound of claim 4, wherein the compound is of formula (I'ab):

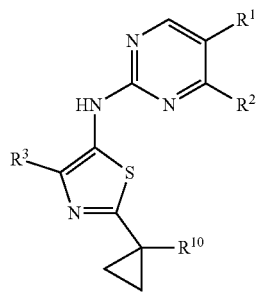
(I'ab)

or a pharmaceutically acceptable salt, deuterated isotope, or stereoisomer thereof,
wherein:
$R^{10}$ is H, cyano, $C(O)NR^{12}R^{13}$, heteroaryl, or alkylheteroaryl.

9. The compound of claim 8, or a pharmaceutically acceptable salt, deuterated isotope, or stereoisomer thereof, wherein $R^{10}$ is H, cyano, or heteroaryl.

10. The compound of claim 8, or a pharmaceutically acceptable salt, deuterated isotope, or stereoisomer thereof, wherein $R^{10}$ is H, cyano, or 1H-1,2,4-triazol-3-yl.

11. The compound of claim 4, wherein the compound is of formula (I'ac):

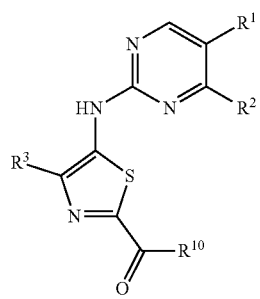
(I'ac)

or a pharmaceutically acceptable salt, deuterated isotope, or stereoisomer thereof,
wherein:
$R^{10}$ is $C_{1-6}$ alkyl, $C_{1-6}$ haloalkyl, amino, $C_{1-6}$ alkylamino, or heterocyclyl, wherein the heterocyclyl is optionally and independently substituted with one or more independently selected halo substituents.

12. The compound of claim 11, or a pharmaceutically acceptable salt, deuterated isotope, or stereoisomer thereof, wherein $R^{10}$ is methylamino, morpholin-4-yl, 3,3-difluoropyrrolidin-1-yl, or 8-oxa-3-azabicyclo[3.2.1]octan-3-yl.

13. The compound of claim 4, wherein the compound is of formula (I'ad):

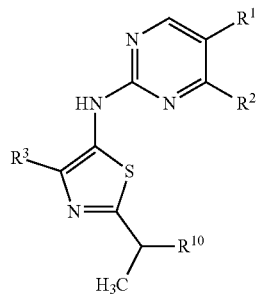
(I'ad)

or a pharmaceutically acceptable salt, deuterated isotope, or stereoisomer thereof,
wherein:
$R^{10}$ is H, cyano, $C(O)NR^{12}R^{13}$, heteroaryl, or alkylheteroaryl.

14. The compound of claim 13, or a pharmaceutically acceptable salt, deuterated isotope, or stereoisomer thereof, wherein $R^{10}$ is cyano or 1H-1,2,4-triazol-1-yl.

15. The compound of claim 2, wherein the compound is of formula (I'ae):

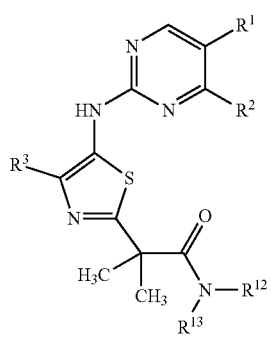
(I'ae)

or a pharmaceutically acceptable salt, deuterated isotope, or stereoisomer thereof.

16. The compound of claim 15, or a pharmaceutically acceptable salt, deuterated isotope, or stereoisomer thereof, wherein:
$R^{12}$ is H; and
$R^{13}$ is H.

17. The compound of claim 2, wherein the compound is of formula (I'ag):

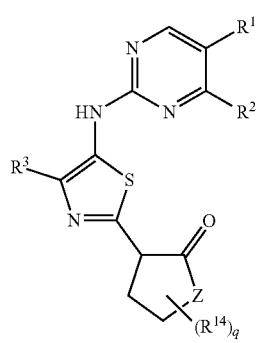
(I'ag)

or a pharmaceutically acceptable salt, deuterated isotope, or stereoisomer thereof,
wherein:
q is 0, 1, 2, or 3;
Z is —NR$^{15}$— or —O—;
R$^{14}$ is halo or C$_{1-6}$ alkyl; and
R$^{15}$ is H or C$_{1-6}$ alkyl.

18. The compound of claim 17, or a pharmaceutically acceptable salt, deuterated isotope, or stereoisomer thereof, wherein:
q is 1 or 2; and
each R$^{14}$ is independently CD$_3$.

19. The compound of claim 17, or a pharmaceutically acceptable salt, deuterated isotope, or stereoisomer thereof, wherein R$^3$ is halo.

20. The compound of claim 1, wherein the compound is of formula (I'd):

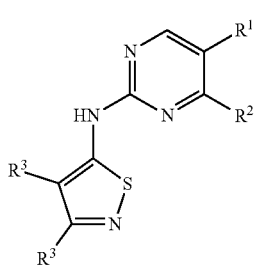

or a pharmaceutically acceptable salt, deuterated isotope, or stereoisomer thereof.

21. The compound of claim 3, wherein the compound is of formula (II):

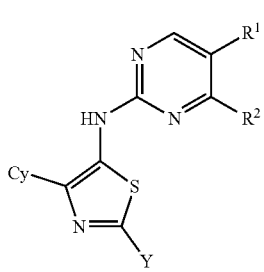

or a pharmaceutically acceptable salt, deuterated isotope, or stereoisomer thereof,
wherein:
Cy is cycloalkyl, optionally and independently substituted with one or more substituents independently selected from the group consisting of oxo, thioxo, halo, cyano, hydrazino, azido, nitro, alkyl, haloalkyl, hydroxyalkyl, cycloalkylalkyl, heterocyclylalkyl, aralkyl, heteroarylalkyl, alkenyl, alkynyl, imino, hydrazone, amidino, oxime, C(O)H, amido, imido, carboxy, C(O)Oalkyl, amino, guanidino, NHC(O)Oalkyl, hydroxy, alkoxy, haloalkoxy, OC(O)NH$_2$, thiol, thiocyanate, alkylthio, alkylsulfinyl, alkylsulfonyl, sulfonamido, sulfinic acid, sulfonic acid, cycloalkyl, heterocyclyl, aryl, heteroaryl, and Si(R$^Y$)$_3$;
Y is H, halo, cyano, C$_{1-6}$ alkyl, C$_{1-6}$ haloalkyl, C$_{1-6}$ cyanoalkyl, C$_{1-6}$ aminoalkyl, amidoalkyl, C$_{1-6}$ hydroxyalkyl, C$_{1-6}$ alkoxyalkyl, C(O)R$^7$, amido, N(R$^{16}$)$_2$, C$_{1-6}$ alkylsulfonyl, C$_{1-6}$ alkylsulfonylalkyl, cycloalkylalkyl, heterocyclylalkyl, alkylheterocyclylalkyl, arylalkyl, heteroarylalkyl, alkylheteroarylalkyl, cycloalkyl, cyanocycloalkyl, heteroarylcycloalkyl, alkylheteroarylcycloalkyl, heterocyclyl, aryl, or heteroaryl, wherein the C$_{1-6}$ alkyl, C$_{1-6}$ haloalkyl, C$_{1-6}$ cyanoalkyl, C$_{1-6}$ aminoalkyl, C$_{1-6}$ hydroxyalkyl, C$_{1-6}$ alkoxyalkyl, C$_{1-6}$ alkylsulfonyl, C$_{1-6}$ alkylsulfonylalkyl, cycloalkylalkyl, heterocyclylalkyl, alkylheterocyclylalkyl, arylalkyl, heteroarylalkyl, alkylheteroarylalkyl, cycloalkyl, cyanocycloalkyl, heteroarylcycloalkyl, alkylheteroarylcycloalkyl, heterocyclyl, aryl, and heteroaryl is optionally and independently substituted with one or more substituents independently selected from the group consisting of oxo, thioxo, halo, cyano, hydrazino, azido, nitro, alkyl, haloalkyl, hydroxyalkyl, cycloalkylalkyl, heterocyclylalkyl, aralkyl, heteroarylalkyl, alkenyl, alkynyl, imino, hydrazone, amidino, oxime, C(O)H, amido, imido, carboxy, C(O)Oalkyl, amino, guanidino, NHC(O)Oalkyl, hydroxy, alkoxy, haloalkoxy, OC(O)NH$_2$, thiol, thiocyanate, alkylthio, alkylsulfinyl, alkylsulfonyl, sulfonamido, sulfinic acid, sulfonic acid, cycloalkyl, heterocyclyl, aryl, heteroaryl, and Si(R$^Y$)$_3$;
R$^7$ is C$_{1-6}$ alkyl, C$_{1-6}$ haloalkyl, C$_{1-6}$ alkoxy, or heterocyclyl, wherein each C$_{1-6}$ alkyl, C$_{1-6}$ haloalkyl, C$_{1-6}$ alkoxy, and heterocyclyl is optionally and independently substituted with one or more substituents independently selected from the group consisting of halo, cyano, hydroxy, C$_{1-6}$ alkoxy, and C$_{1-6}$ alkylsulfonyl; and
each R$^{16}$ is independently H or C$_{1-6}$ alkyl, wherein each C$_{1-6}$ alkyl is optionally and independently substituted with one or more substituents independently selected from the group consisting of halo, cyano, hydroxy, C$_{1-6}$ alkoxy, and C$_{1-6}$ alkylsulfonyl.

22. The compound of claim 21, or a pharmaceutically acceptable salt, deuterated isotope, or stereoisomer thereof, wherein Cy is cycloalkyl, optionally and independently substituted with one or two substituents independently selected from the group consisting of halo, hydroxy, and heteroaryl.

23. The compound of claim 21, or a pharmaceutically acceptable salt, deuterated isotope, or stereoisomer thereof, wherein:
Y is cyano, C$_{1-6}$ alkyl, amidoalkyl, C$_{1-6}$ cyanoalkyl, C$_{1-6}$ hydroxyalkyl, C$_{1-6}$ alkoxyalkyl, C(O)R$^7$, C(O)NHC$_{1-6}$ alkyl, heteroarylalkyl, alkylheteroarylalkyl, cycloalkyl, cyanocycloalkyl, heteroarylcycloalkyl, or heterocyclyl, wherein the heterocyclyl is optionally and independently substituted with oxo and one or two independently selected C$_{1-6}$ alkyl substituents; and
R$^7$ is heterocyclyl, optionally and independently substituted with one, two, or three independently selected halo substituents.

24. The compound of claim 1, or a pharmaceutically acceptable salt, deuterated isotope, or stereoisomer thereof, wherein R$^1$ is halo or C$_{1-6}$ alkyl.

25. The compound of claim 1, or a pharmaceutically acceptable salt, deuterated isotope, or stereoisomer thereof, wherein R$^1$ is halo or C$_{1-6}$ haloalkyl.

26. The compound of claim 1, or a pharmaceutically acceptable salt, deuterated isotope, or stereoisomer thereof, wherein R$^1$ is C$_{1-6}$ fluoroalkyl.

27. The compound of claim 1, or a pharmaceutically acceptable salt, deuterated isotope, or stereoisomer thereof, wherein $R^1$ is $CF_3$.

28. The compound of claim 1, or a pharmaceutically acceptable salt, deuterated isotope, or stereoisomer thereof, wherein $R^2$ is $NHCH_3$, $NHCH_2CH_3$, $NH(CF_2CH_3)$, or NHcyclopropyl.

29. The compound of claim 1, or a pharmaceutically acceptable salt, deuterated isotope, or stereoisomer thereof, wherein $R^2$ is $NHCH_2CH_3$.

30. The compound of claim 1, or a pharmaceutically acceptable salt, deuterated isotope, or stereoisomer thereof, wherein each $R^3$ is independently halo, cyano, $C_{1-6}$ alkyl, $C_{1-6}$ haloalkyl, $C_{1-6}$ cyanoalkyl, $C_{1-6}$ aminoalkyl, amidoalkyl, $C_{1-6}$ hydroxyalkyl, $C_{1-6}$ alkoxyalkyl, $C(O)R^7$, amido, $C_{1-6}$ alkylsulfonyl, $C_{1-6}$ alkylsulfonylalkyl, cycloalkylalkyl, heterocyclylalkyl, alkylheterocyclylalkyl, arylalkyl, heteroarylalkyl, alkylheteroarylalkyl, cycloalkyl, cyanocycloalkyl, heteroarylcycloalkyl, alkylheteroarylcycloalkyl, heterocyclyl, or aryl, wherein each $C_{1-6}$ alkyl, $C_{1-6}$ haloalkyl, $C_{1-6}$ cyanoalkyl, $C_{1-6}$ aminoalkyl, $C_{1-6}$ hydroxyalkyl, $C_{1-6}$ alkoxyalkyl, $C_{1-6}$ alkylsulfonyl, $C_{1-6}$ alkylsulfonylalkyl, cycloalkylalkyl, heterocyclylalkyl, alkylheterocyclylalkyl, arylalkyl, heteroarylalkyl, alkylheteroarylalkyl, cycloalkyl, cyanocycloalkyl, heteroarylcycloalkyl, alkylheteroarylcycloalkyl, heterocyclyl, and aryl is optionally and independently substituted with one or more substituents independently selected from the group consisting of oxo, thioxo, halo, cyano, hydrazino, azido, nitro, alkyl, haloalkyl, hydroxyalkyl, cycloalkylalkyl, heterocyclylalkyl, aralkyl, heteroarylalkyl, alkenyl, alkynyl, imino, hydrazone, amidino, oxime, C(O)H, amido, imido, carboxy, C(O)Oalkyl, amino, guanidino, NHC(O)Oalkyl, hydroxy, alkoxy, haloalkoxy, $OC(O)NH_2$, thiol, thiocyanate, alkylthio, alkylsulfinyl, alkylsulfonyl, sulfonamido, sulfinic acid, sulfonic acid, cycloalkyl, heterocyclyl, aryl, heteroaryl, and $Si(R^Y)_3$.

31. The compound of claim 1, or a pharmaceutically acceptable salt, deuterated isotope, or stereoisomer thereof, wherein each $R^3$ is independently H, halo, $C_{1-6}$ alkyl, or cycloalkyl.

32. The compound of claim 1, or a pharmaceutically acceptable salt, deuterated isotope, or stereoisomer thereof, wherein at least one $R^3$ is not H.

33. The compound of claim 1, or a pharmaceutically acceptable salt, deuterated isotope, or stereoisomer thereof, wherein at least one $R^3$ is H.

34. The compound of claim 1, or a pharmaceutically acceptable salt, deuterated isotope, or stereoisomer thereof, wherein at least one $R^3$ is optionally substituted cycloalkyl.

35. The compound of claim 1, or a pharmaceutically acceptable salt, deuterated isotope, or stereoisomer thereof, wherein at least one $R^3$ is cyclopropyl or cyclobutyl, wherein each cyclopropyl and cyclobutyl is optionally and independently substituted with one or two substituents independently selected from the group consisting of halo, hydroxy, alkoxy, and heteroaryl.

36. The compound of claim 1, or a pharmaceutically acceptable salt, deuterated isotope, or stereoisomer thereof, wherein:
 m is 2;
 ring A is thiazolyl; and
 each $R^3$ is independently halo, $C_{1-6}$ alkyl, $C_{1-6}$ haloalkyl, cycloalkyl, or heterocyclyl, wherein each $C_{1-6}$ alkyl, cycloalkyl, and heterocyclyl is optionally and independently substituted with one or more substituents independently selected from the group consisting of oxo, halo, $C_{1-6}$ alkyl, $C_{1-6}$ haloalkyl, cycloalkyl, and heterocyclyl;
 wherein one, two, three, four, five, or six hydrogens of each $C_{1-6}$ alkyl is optionally and independently replaced by deuterium.

37. The compound of claim 1, or a pharmaceutically acceptable salt, deuterated isotope, or stereoisomer thereof, wherein:
 $R^1$ is halo or $C_{1-6}$ haloalkyl;
 $R^2$ is $N(R^5)(R^6)$, $C_{1-6}$alkoxy, or cycloalkyl;
 each $R^3$ is independently H, halo, cyano, $C_{1-6}$ alkyl, $C_{1-6}$ cyanoalkyl, $C(O)R^7$, $C(O)NH(C_{1-6}$ alkyl), heteroarylalkyl, alkylheteroarylalkyl, cycloalkyl, cyanocycloalkyl, heteroarylcycloalkyl, or heterocyclyl, wherein each heterocyclyl is substituted with oxo and one or two independently selected $C_{1-6}$ alkyl substituents;
 $R^5$ is H, $C_{1-6}$ alkyl, or cycloalkyl, wherein the $C_{1-6}$ alkyl is optionally and independently substituted with one, two, or three independently selected halo substituents;
 $R^6$ is H, $C_{1-6}$ alkyl, or cycloalkyl, wherein the $C_{1-6}$ alkyl is optionally and independently substituted with one, two, or three independently selected halo substituents; and
 each $R^7$ is independently heterocyclyl, each optionally and independently substituted with one, two, or three independently selected halo substituents.

38. A pharmaceutical composition comprising the compound of claim 1, or a pharmaceutically acceptable salt, deuterated isotope, or stereoisomer thereof, and a pharmaceutically acceptable carrier, diluent, or excipient.

39. A method for enhancing cognitive memory in a subject, comprising administering to the subject in need thereof an effective amount of the compound of claim 1, or a pharmaceutically acceptable salt, deuterated isotope, or stereoisomer thereof.

40. A method for enhancing memory in a subject, comprising administering to the subject in need thereof an effective amount of a pharmaceutical composition comprising the compound of claim 1, or a pharmaceutically acceptable salt, deuterated isotope, or stereoisomer thereof, and a pharmaceutically acceptable carrier, diluent, or excipient.

41. A method for modulating leucine-rich repeat kinase 2 activity in a subject, comprising administering to the subject in need thereof an effective amount of the compound of claim 1, or a pharmaceutically acceptable salt, deuterated isotope, or stereoisomer thereof.

42. The method of claim 41, wherein the subject has cancer.

43. The method of claim 42, wherein the cancer is acute myelogenous leukemia, blood cancer, breast cancer, lung cancer, kidney cancer, prostate cancer, papillary cancer, or multiple myeloma.

44. The method of claim 41, wherein the subject has an inflammatory disease.

45. The method of claim 44, wherein the inflammatory disease is amyotrophic lateral sclerosis, ankylosing spondylitis, Crohn's disease, inflammatory bowel disease, leprosy, rheumatoid arthritis, or ulcerative colitis.

46. The method of claim 41, wherein the subject has a neurodegenerative disease.

47. The method of claim 46, wherein the neurodegenerative disease is a central nervous system disorder.

48. The method of claim 47, wherein the central nervous system disorder is Alzheimer's disease or levodopa-induced dyskinesia.

49. The method of claim 46, wherein the neurodegenerative disease is dementia or Parkinson's disease.

50. A method for modulating leucine-rich repeat kinase 2 activity in a subject, comprising administering to the subject in need thereof an effective amount of a pharmaceutical composition comprising the compound of claim 1, or a pharmaceutically acceptable salt, deuterated isotope, or stereoisomer thereof, and a pharmaceutically acceptable carrier, diluent, or excipient.

51. A process for preparing the compound of formula (I) of claim 1:

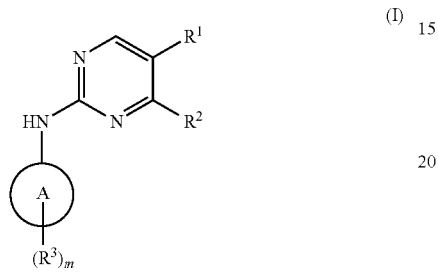

wherein:
m is 1 or 2;
ring A is isothiazolyl or thiazolyl;
$R^1$ is halo, cyano, $C_{1-6}$ alkyl, or $C_{1-6}$ haloalkyl;
$R^2$ is $N(R^5)(R^6)$, $C_{1-6}$ alkoxy, or cycloalkyl;
each $R^3$ is independently H, halo, cyano, $C_{1-6}$ alkyl, $C_{1-6}$ haloalkyl, $C_{1-6}$ cyanoalkyl, $C_{1-6}$ aminoalkyl, amidoalkyl, $C_{1-6}$ hydroxyalkyl, $C_{1-6}$ alkoxyalkyl, $C(O)R^7$, amido, $N(R^{16})_2$, $C_{1-6}$ alkylsulfonyl, $C_{1-6}$ alkylsulfonylalkyl, cycloalkylalkyl, heterocyclylalkyl, alkylheterocyclylalkyl, arylalkyl, heteroarylalkyl, alkylheteroarylalkyl, cycloalkyl, cyanocycloalkyl, heteroarylcycloalkyl, alkylheteroarylcycloalkyl, heterocyclyl, aryl, or heteroaryl, wherein each $C_{1-6}$ alkyl, $C_{1-6}$ haloalkyl, $C_{1-6}$ cyanoalkyl, $C_{1-6}$ aminoalkyl, $C_{1-6}$ hydroxyalkyl, $C_{1-6}$ alkoxyalkyl, $C_{1-6}$ alkylsulfonyl, $C_{1-6}$ alkylsulfonylalkyl, cycloalkylalkyl, heterocyclylalkyl, alkylheterocyclylalkyl, arylalkyl, heteroarylalkyl, alkylheteroarylalkyl, cycloalkyl, cyanocycloalkyl, heteroarylcycloalkyl, alkylheteroarylcycloalkyl, heterocyclyl, aryl, and heteroaryl is optionally and independently substituted with one or more substituents independently selected from the group consisting of oxo, thioxo, halo, cyano, hydrazino, azido, nitro, alkyl, haloalkyl, hydroxyalkyl, cycloalkylalkyl, heterocyclylalkyl, aralkyl, heteroarylalkyl, alkenyl, alkynyl, imino, hydrazone, amidino, oxime, C(O)H, amido, imido, carboxy, C(O)Oalkyl, amino, guanidino, NHC(O)Oalkyl, hydroxy, alkoxy, haloalkoxy, $OC(O)NH_2$, thiol, thiocyanate, alkylthio, alkylsulfinyl, alkylsulfonyl, sulfonamido, sulfinic acid, sulfonic acid, cycloalkyl, heterocyclyl, aryl, heteroaryl, and $Si(R^Y)_3$;
$R^5$ is H, $C_{1-6}$alkyl, $C_{1-6}$ haloalkyl, or cycloalkyl;
$R^6$ is H, $C_{1-6}$ alkyl $C_{1-6}$ haloalkyl, or cycloalkyl;
each $R^7$ is independently $C_{1-6}$ alkyl, $C_{1-6}$ haloalkyl, $C_{1-6}$ alkoxy, or heterocyclyl, wherein each $C_{1-6}$ alkyl, $C_{1-6}$ haloalkyl, $C_{1-6}$ alkoxy, and heterocyclyl is optionally and independently substituted with one or more substituents independently selected from the group consisting of halo, cyano, hydroxy, $C_{1-6}$ alkoxy, and $C_{1-6}$ alkylsulfonyl;

each $R^{16}$ is independently H or $C_{1-6}$ alkyl, wherein each $C_{1-6}$ alkyl is optionally and independently substituted with one or more substituents independently selected from the group consisting of halo, cyano, hydroxy, $C_{1-6}$ alkoxy, and $C_{1-6}$ alkylsulfonyl; and each $R^Y$ is independently H, alkyl, alkenyl, alkynyl, heteroalkyl, cycloalkyl, heterocyclyl, aryl, or heteroaryl;

with the proviso that if $R^5$ or $R^6$ is cycloalkyl, then ring A is not isothiazolyl;

wherein the process comprises:
coupling a compound of formula (Y):

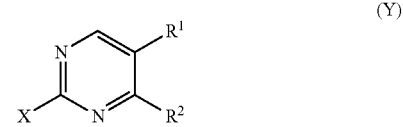

wherein:
$R^1$ is halo, cyano, $C_{1-6}$ alkyl, or $C_{1-6}$ haloalkyl;
$R^2$ is $N(R^5)(R^6)$, $C_{1-6}$ alkoxy, or cycloalkyl;
$R^5$ is H, $C_{1-6}$ alkyl, $C_{1-6}$ haloalkyl, or cycloalkyl;
$R^6$ is H, $C_{1-6}$ alkyl, $C_{1-6}$ haloalkyl, or cycloalkyl; and
X is selected from the group consisting of:
halo

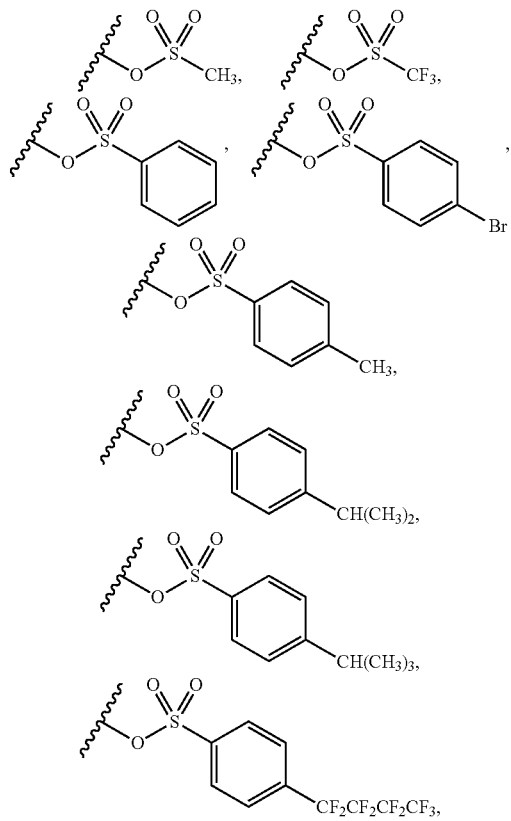

-continued

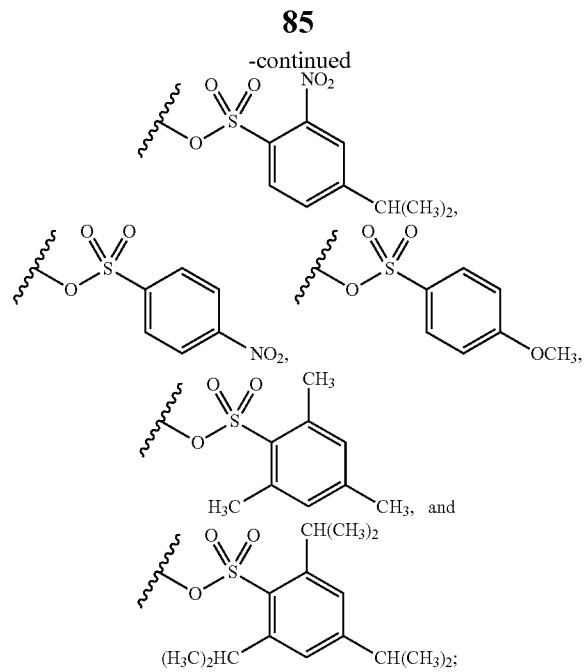

with a compound of formula (Z):

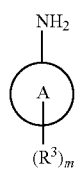

(Z)

wherein:
  m is 1 or 2;
  ring A is isothiazolyl or thiazolyl;
  each $R^3$ is independently H, halo, cyano, $C_{1-6}$ alkyl, $C_{1-6}$ haloalkyl, $C_{1-6}$ cyanoalkyl, $C_{1-6}$ aminoalkyl, amidoalkyl, $C_{1-6}$ hydroxyalkyl, $C_{1-6}$ alkoxyalkyl, $C(O)R^7$, amido, $N(R^{16})_2$, $C_{1-6}$ alkylsulfonyl, $C_{1-6}$ alkylsulfonylalkyl, cycloalkylalkyl, heterocyclylalkyl, alkylheterocyclylalkyl, arylalkyl, heteroarylalkyl, alkylheteroarylalkyl, cycloalkyl, cyanocycloalkyl, heteroarylcycloalkyl, alkylheteroarylcycloalkyl, heterocyclyl, aryl, or heteroaryl, wherein each $C_{1-6}$ alkyl, $C_{1-6}$ haloalkyl, $C_{1-6}$ cyanoalkyl, $C_{1-6}$ aminoalkyl, $C_{1-6}$ hydroxyalkyl, $C_{1-6}$ alkoxyalkyl, $C_{1-6}$ alkylsulfonyl, $C_{1-6}$ alkylsulfonylalkyl, cycloalkylalkyl, heterocyclylalkyl, alkylheterocyclylalkyl, arylalkyl, heteroarylalkyl, alkylheteroarylalkyl, cycloalkyl, cyanocycloalkyl, heteroarylcycloalkyl, alkylheteroarylcycloalkyl, heterocyclyl, aryl, and heteroaryl is optionally and independently substituted with one or more substituents independently selected from the group consisting of oxo, thioxo, halo, cyano, hydrazino, azido, nitro, alkyl, haloalkyl, hydroxyalkyl, cycloalkylalkyl, heterocyclylalkyl, aralkyl, heteroarylalkyl, alkenyl, alkynyl, imino, hydrazone, amidino, oxime, C(O)H, amido, imido, carboxy, C(O)Oalkyl, amino, guanidino, NHC(O)Oalkyl, hydroxy, alkoxy, haloalkoxy, $OC(O)NH_2$, thiol, thiocyanate, alkylthio, alkylsulfinyl, alkylsulfonyl, sulfonamido, sulfinic acid, sulfonic acid, cycloalkyl, heterocyclyl, aryl, heteroaryl, and $Si(R^Y)_3$;

each $R^7$ is independently $C_{1-6}$ alkyl, $C_{1-6}$ haloalkyl, $C_{1-6}$ alkoxy, or heterocyclyl, wherein each $C_{1-6}$ alkyl, $C_{1-6}$ haloalkyl, $C_{1-6}$ alkoxy, and heterocyclyl is optionally and independently substituted with one or more substituents independently selected from the group consisting of halo, cyano, hydroxy, $C_{1-6}$ alkoxy, and $C_{1-6}$ alkylsulfonyl;

each $R^{16}$ is independently H or $C_{1-6}$ alkyl, wherein each $C_{1-6}$ alkyl is optionally and independently substituted with one or more substituents independently selected from the group consisting of halo, cyano, hydroxy, $C_{1-6}$ alkoxy, and $C_{1-6}$ alkylsulfonyl; and each $R^Y$ is independently H, alkyl, alkenyl, alkynyl, heteroalkyl, cycloalkyl, heterocyclyl, aryl, or heteroaryl;

with the proviso that if $R^5$ or $R^6$ is cycloalkyl, then ring A is not isothiazolyl;

in the presence of trifluoroacetic acid, toluenesulfonic acid, or triethylamine, to provide the compound of formula (I) above.

52. A compound, or a pharmaceutically acceptable salt, deuterated isotope, or stereoisomer thereof, selected from the group consisting of:

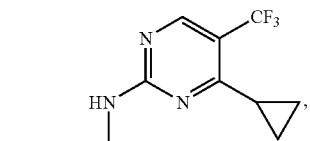

1

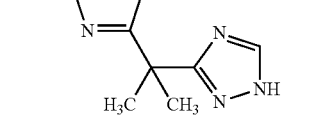

2

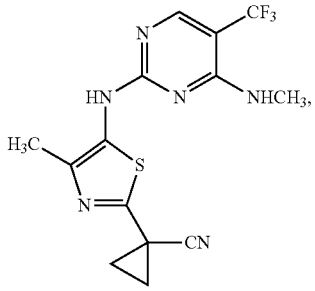

3

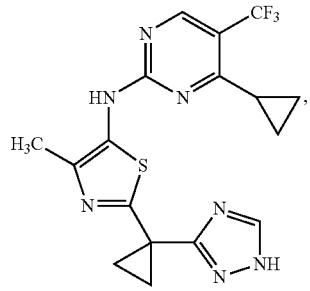

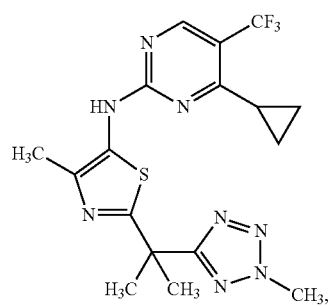
4
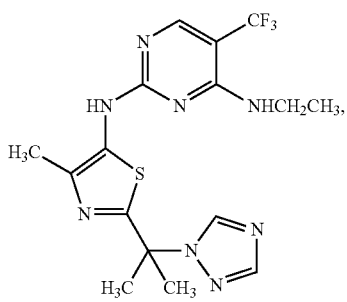
5
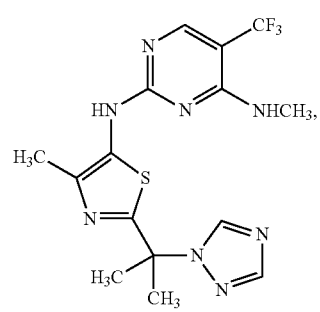
6
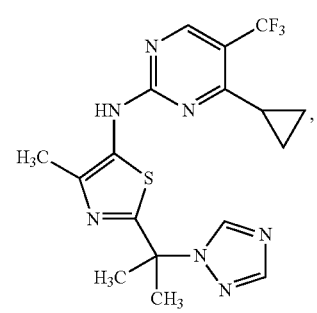
7
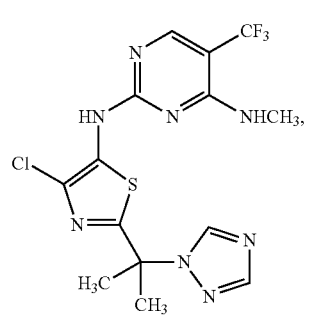
8
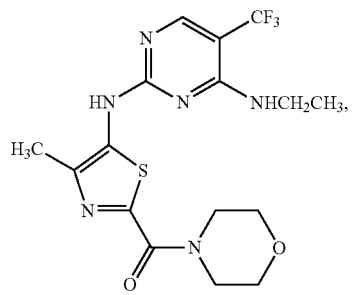
9
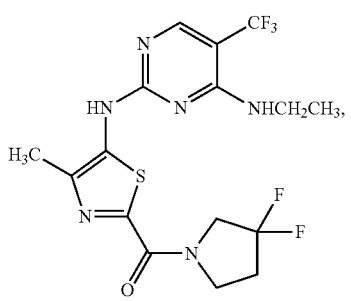
10
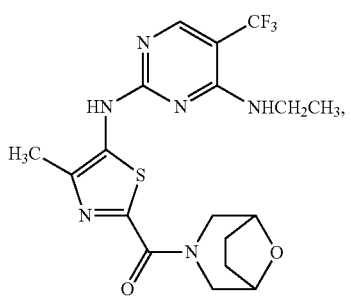
11
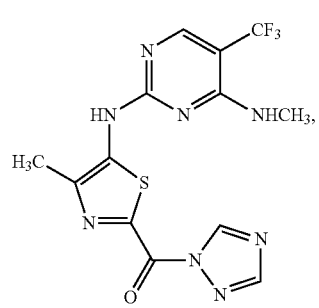
12
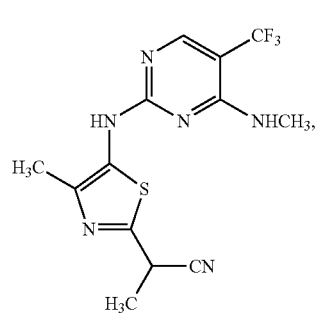
13

17 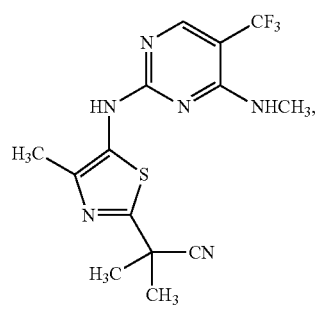
18 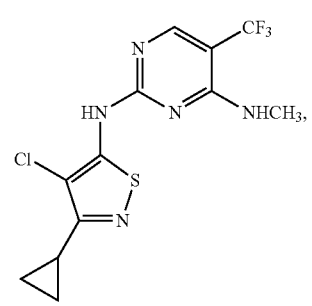
21 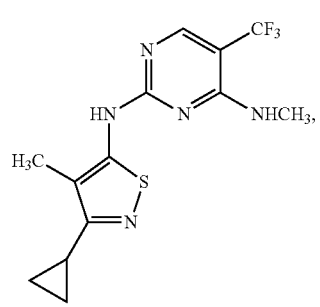
22 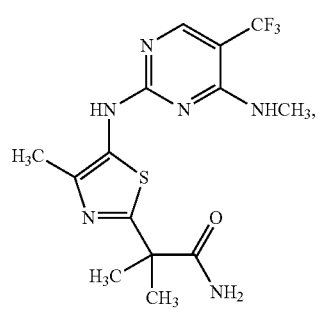
23 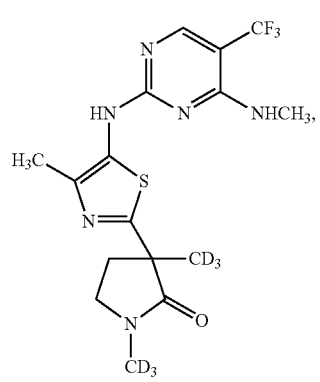
25 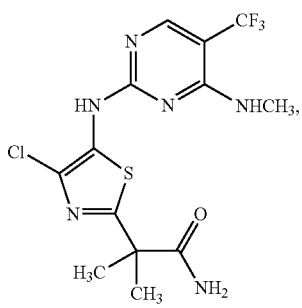
26 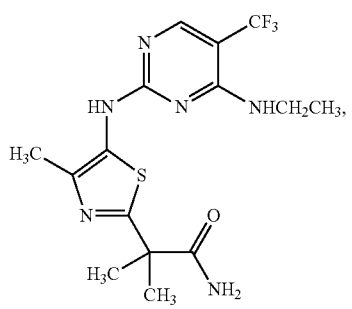
27 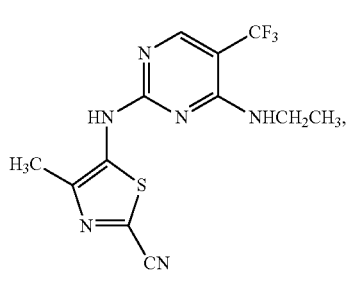
28 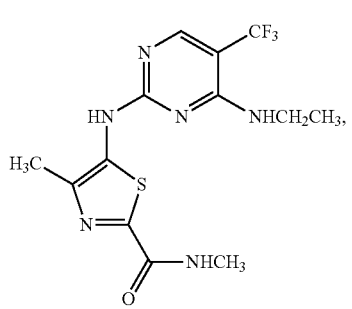
29

-continued
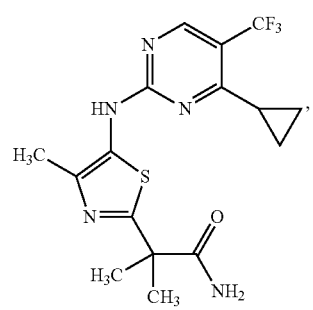
30
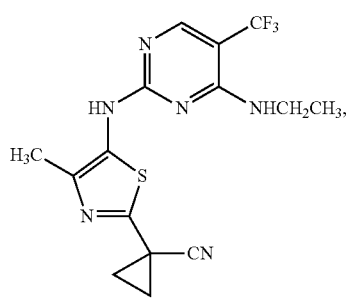
32
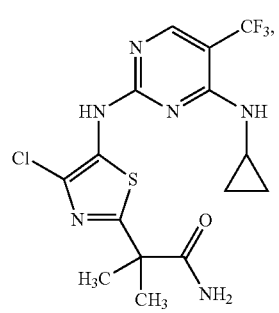
34
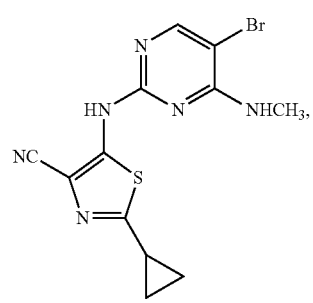
35
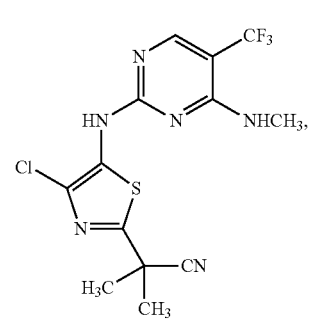
36
-continued
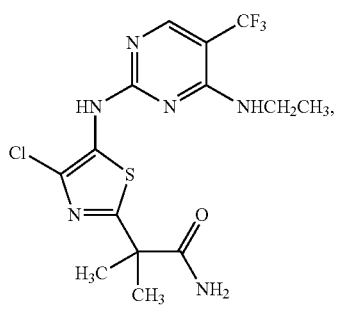
37
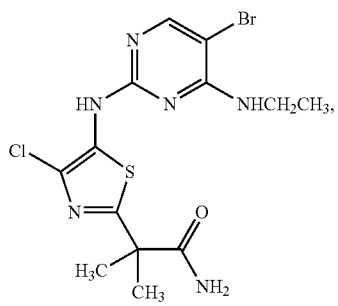
38
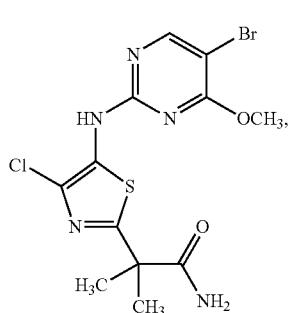
39
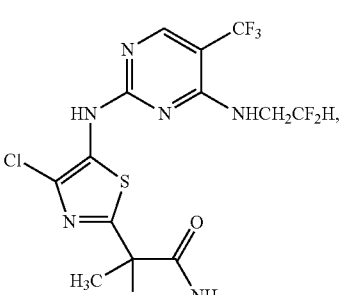
40
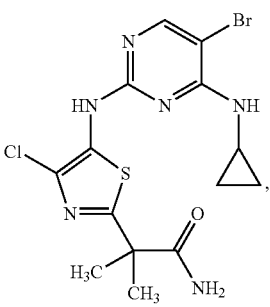
41

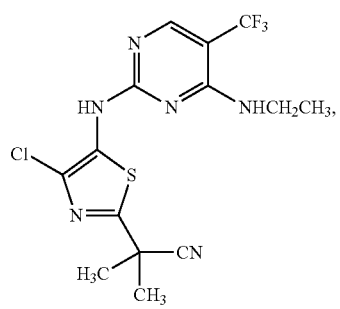
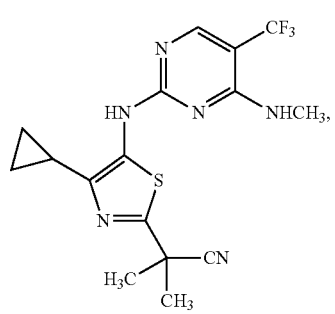
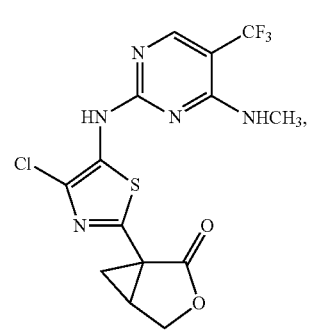
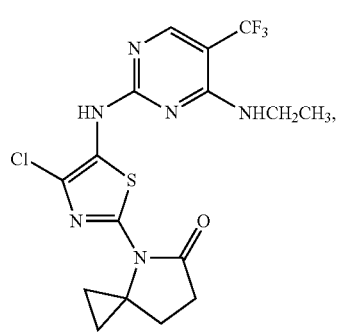
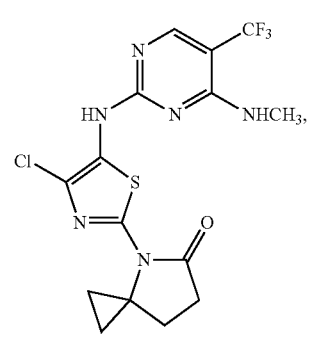
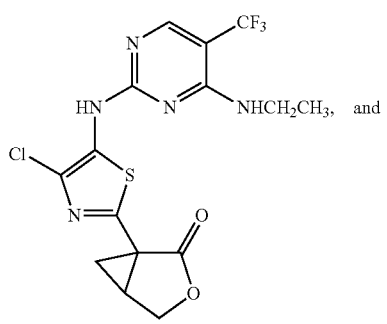
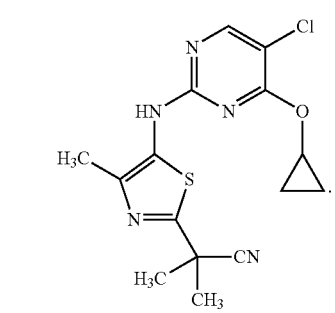
53. A compound, or a pharmaceutically acceptable salt thereof, selected from the group consisting of:
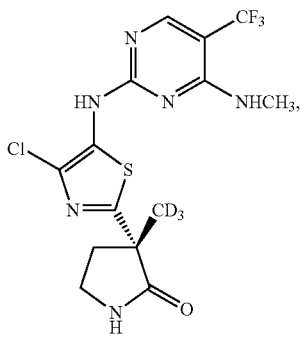
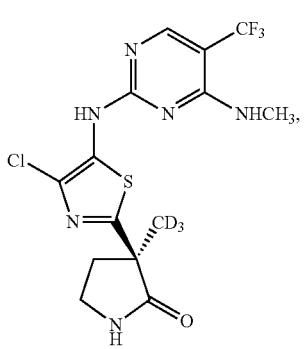

-continued
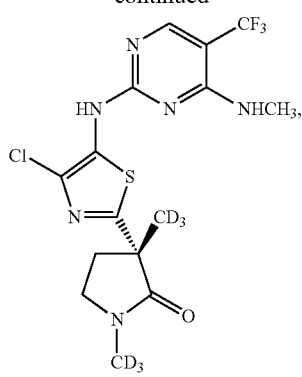
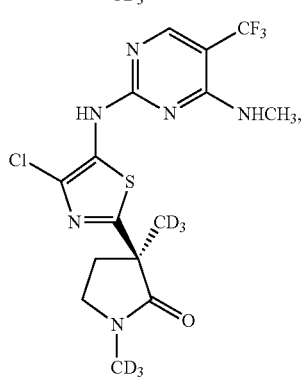
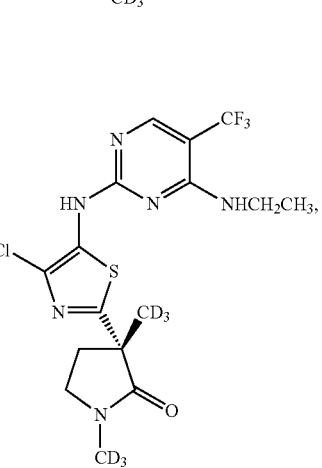
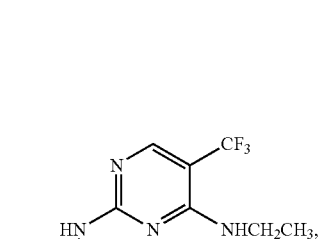
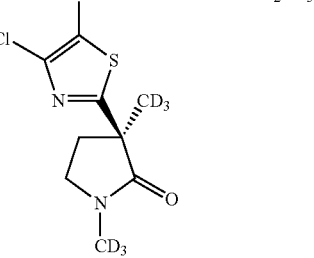
-continued
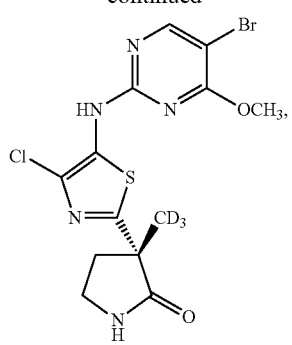
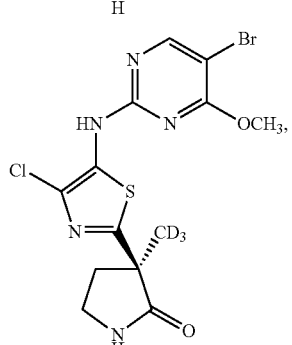
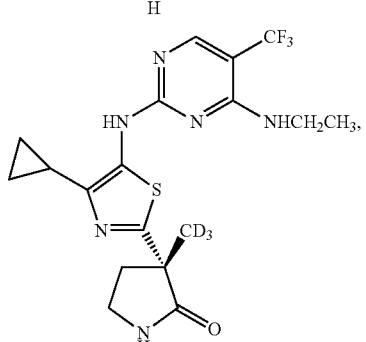
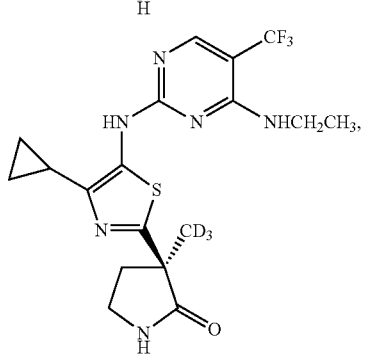
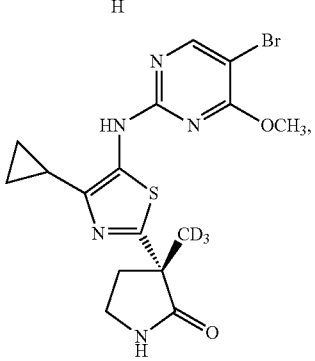

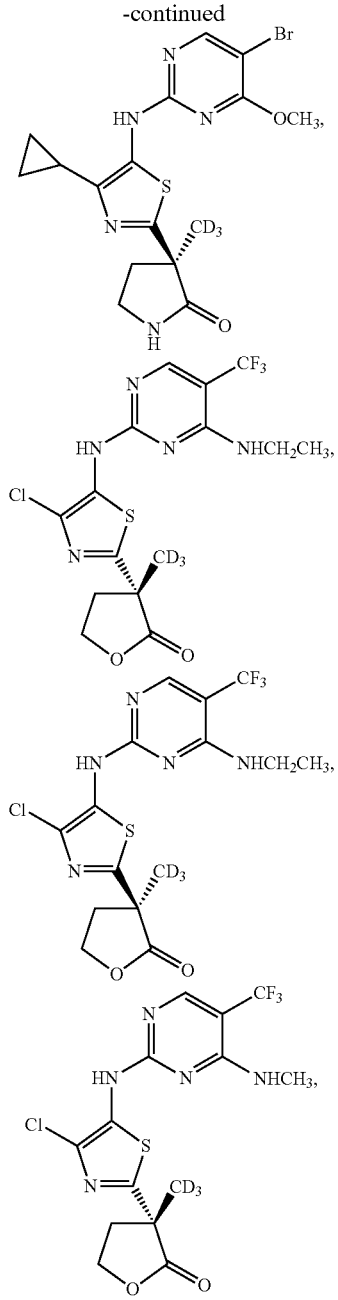
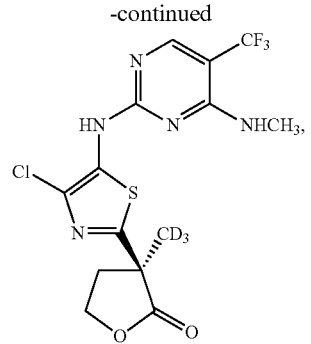
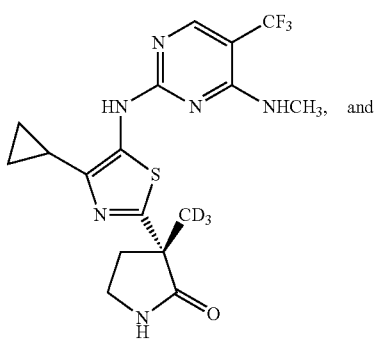
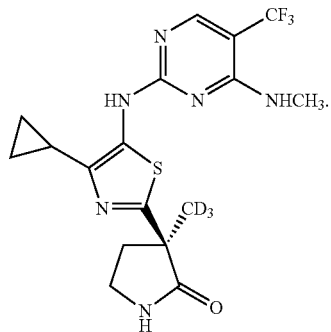
* * * * *